United States Patent
Zheng et al.

(10) Patent No.: US 10,688,082 B2
(45) Date of Patent: Jun. 23, 2020

(54) AMINOPYRAZINE COMPOUNDS WITH A2A ANTAGONIST PROPERTIES

(71) Applicant: Merck Sharp & Dohme Corp., Rahway, NJ (US)

(72) Inventors: Junying Zheng, New Providence, NJ (US); Walter Won, Alpine, NJ (US); Michael Berlin, Flemington, NJ (US); Pauline Ting, New Providence, NJ (US); Guoqing Li, Belle Mead, NJ (US); Dong Xiao, Somerset, NJ (US); Hongwu Wang, Westfield, NJ (US); Robert Aslanian, Rockaway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/815,212

(22) PCT Filed: Jun. 6, 2016

(86) PCT No.: PCT/US2016/035960
§ 371 (c)(1),
(2) Date: Nov. 16, 2017

(87) PCT Pub. No.: WO2016/200717
PCT Pub. Date: Dec. 15, 2016

(65) Prior Publication Data
US 2018/0193314 A1  Jul. 12, 2018

Related U.S. Application Data

(60) Provisional application No. 62/174,295, filed on Jun. 11, 2015.

(51) Int. Cl.
| | |
|---|---|
| *A61K 31/4162* | (2006.01) |
| *A61K 31/519* | (2006.01) |
| *A61K 31/497* | (2006.01) |
| *A61P 25/00* | (2006.01) |
| *A01N 43/80* | (2006.01) |
| *C07D 487/04* | (2006.01) |
| *C07D 487/10* | (2006.01) |

(52) U.S. Cl.
CPC ........ *A61K 31/4162* (2013.01); *A01N 43/80* (2013.01); *A61K 31/497* (2013.01); *A61K 31/519* (2013.01); *A61P 25/00* (2018.01); *C07D 487/04* (2013.01); *C07D 487/10* (2013.01)

(58) Field of Classification Search
CPC ...... A01N 43/80; A01N 25/04; C07D 487/10; C07D 487/04; A61K 31/497; A61K 31/59; A61K 31/4162; A61P 25/00
See application file for complete search history.

(56) References Cited

U.S. PATENT DOCUMENTS 3,531,482 A  *  9/1970  Ott .................. C07D 487/04
                                                   544/115

FOREIGN PATENT DOCUMENTS

| WO | WO2010030785 A2 | 3/2010 |
| WO | 2014018925 | * 1/2014 |
| WO | 2014101120 A1 | * 7/2014 |
| WO | WO2014101120 | 7/2014 |
| WO | WO2015031221 | 3/2015 |

OTHER PUBLICATIONS

Yang Xiaobo et al., Easy and efficient one-pot synthesis of pyrazole[1,5-c]quinazolines under mild copper-catalyzed conditions; Royal Society of chemistry journal (RSC Advances (2012), 2(29), 11061-11066.*

Catarzi, D et al, Pyrazolo[1,5-c]quinazoline derivatives and their simplified analogues as adenosine receptor antagonists: Synthesis, structure-affinity relatioships and molecular modeling studies, Biorganic & Medicinal Chemistry 2013, 283-294, 21 (1).

Yang, X et al, Easy and efficient one-pot synthesis of pyrazolo[1,5-c]quinazolines under mild copper-catalyzed conditions, RSC Advances, 2012, 11061, (11061).

CID 71508481 Compound—Jul. 28, 2016, p. 3.

(Continued)

*Primary Examiner* — Alexander R Pagano
*Assistant Examiner* — Ebeneezer O Sackey
(74) *Attorney, Agent, or Firm* — Janet E. Fair; Catherine D. Fitch

(57) ABSTRACT

Disclosed are compounds having the structure of Formula I, or a pharmaceutically acceptable salt of any thereof, wherein: "Z", $R^1$ and $R^2$ are defined herein, which compounds are believed suitable for use in selectively antagonizing the A2a receptors, for example, those found in high density in the basal ganglia. Such compounds and pharmaceutical formulations are believed to be useful in treatment or management of neurodegenerative diseases, for example, Parkinson's disease, or movement disorders arising from use of certain medications used in the treatment or management of Parkinson's disease.

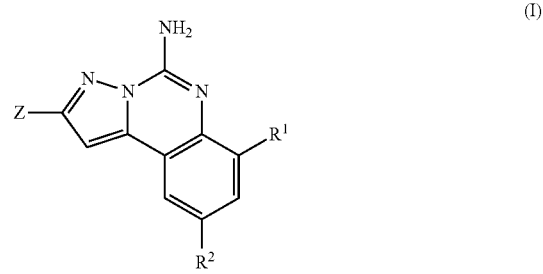

(I)

19 Claims, No Drawings

(56) References Cited

OTHER PUBLICATIONS

NPL—WrittenOpinion—PCTUS2016035960_dated Sep. 2, 2016.
Shook, Adenosine A2A Receptor Antagonists and Parkinson's Disease, ACS Chemical Neuroscience, 2011, 555-567; p. 562, figure 19, 2.

* cited by examiner

AMINOPYRAZINE COMPOUNDS WITH A2A ANTAGONIST PROPERTIES

CROSS-REFERENCE TO RELATED APPLICATIONS

This application is the national stage entry of International Patent Application Serial No. PCT/US2016/035960, filed Jun. 6, 2016, which in turn claims the priority of U.S. Provisional Application Ser. No. 62/174,295 filed Jun. 11, 2015, each of which applications are incorporated herein in their entirety by reference thereto.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication Nos. WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the post-synaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

Formula PI

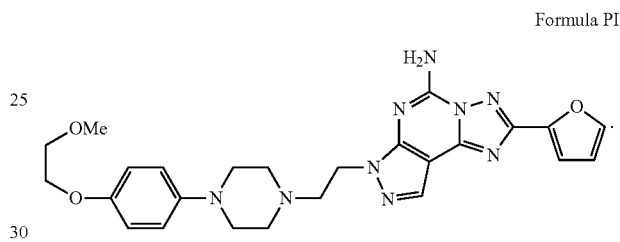

In the '475 patent example Schemes 1 to 5, along with preparative Schemes 1 to 4, show general methods of preparing compounds of Formula PI. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

SUMMARY OF THE INVENTION

In one aspect, the invention provides compounds, or pharmaceutically acceptable salts thereof, of Formula I:

Formula I

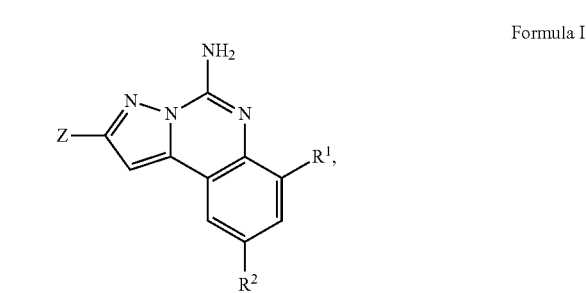

wherein:

$R^1$ and $R^2$ are independently: (a) —H; (b) halogen; or (c) linear, branched or cyclic alkoxy of up to 6 carbon atoms which is optionally substituted on an alkyl carbon thereof by one or more: (i) halogen; (ii) —OH (iii) alkoxy; or (iv) heterocyclyl moiety, preferably piperazine, which heterocyclyl moiety is optionally substituted by an aryl moiety, preferably phenyl, which is optionally substituted with a halogen, or linear-, branched- or cyclic-alkyl of up to 6 carbon atoms, which alkyl substituent is optionally substituted by one or more halogen, lower-alkoxy or —OH;

Z is:
  (I) a moiety of the Formula $R^3$—$CH_2$—, wherein $R^3$ is:
    (a) aryl, which may optionally be substituted with one or more:
      (i) halogen, and in some embodiments, when halogen-substituted, the halogen is preferably —F or —Cl;
      (ii) heterocyclyl, which may optionally be substituted by one or more: (iia) lower alkyl; (iib) ($R^{Ia}$)—O—(C═O)—, wherein $R^{Ia}$ is a linear-, branched-, or cyclic-alkyl of up to 6 carbon atoms; or (iic) —OH;
      (iii) ($R^{Ib}$)$_2$N—, wherein $R^{Ib}$ is independently: —H; or is a linear-, branched-, or cyclic-alkyl of up to 6 carbon atoms, or wherein both $R^{Ib}$ are taken together with the nitrogen to which they are attached form a $C_{3-6}$-cyclo-amine;
      (iv) lower alkyl, which is optionally substituted with one or more: (iva) halogen, and when halogen substituted, preferably the halogen is —F or —Cl; (ivb) aryl; or (ivc) lower alkoxy which is optionally substituted with one or more halogen, and in some embodiments, when halogen substituted, preferably the halogen is —F or —Cl;
      (v) —CN;
      (vi) heteroaryl; which may optionally be substituted with one or more: (via) alkyl wherein said alkyl is a linear-, branched-, or cyclic-alkyl of up to 6 carbon atoms; or (vib) heterocyclyl, which heterocyclyl may optionally be substituted by one or more linear-, branched-, or cyclic-alkyl of up to 6 carbon atoms; or
      (vii) $R^{Ic}$—O—, wherein $R^{Ic}$ is aryl or a linear, branched or cyclic-alkyl of up to 6 carbon atoms, which may optionally be substituted on any carbon atom thereof with one or more halogen, and in some embodiments when halogen substituted, preferably the halogen is —F or —Cl;
    (b) heteroaryl, optionally substituted with one or more: (i) linear, branched or cyclic-alkyl of up to 6 carbon atoms; or (ii) heterocyclyl which is optionally substituted with linear, branched or cyclic-alkyl of up to 6 carbon atoms;
    (c) heterocyclyl, optionally substituted with one or more: (i) —OH; or (ii) linear, branched or cyclic-alkyl of up to 6 carbon atoms;
    (d) arylheterocyclyl, optionally substituted with one or more of: (i) ═O; (ii) halogen, and in some embodiments, when halogen-substituted, preferably the halogen is —F; or
    (e) heteroarylheterocyclyl; or
  (II) a heteroaryl moiety bonded to the pyrazolo-quinazolinyl core through any available ring carbon therein, which heteroaryl moiety comprises 2, 3, or 4 carbon atoms and 1 to 3 heteroatoms which are independently N, S, or O, and wherein, said heteroaryl moiety may optionally be substituted with:
    (a) linear, branched or cyclic-alkyl of up to 6 carbon atoms, which may optionally be substituted with aryl or heteroaryl;
    (b) ($R^{Id}$)$_2$N—, wherein: $R^{Id}$ is —H or linear, branched or cyclic-alkyl of up to 6 carbon atoms, or wherein both $R^{Id}$ together with the nitrogen atom to which they are bonded form $C_{3-6}$-cyclo-amino, and wherein said alkyl may optionally be substituted on one or more carbon atoms thereof by phenyl which is optionally substituted by one or more halogens;
    (c) aryl, and when selected to be aryl, in some embodiments it is preferably phenyl;
    (d) heteroaryl; or
    (e) heterocyclyl, which may optionally be substituted with one or more:
      (i) linear, branched or cyclic-alkyl of up to 6 carbon atoms; (ii) aryl, which may optionally be substituted with one or more halogen, and when halogen-substituted, preferably the halogen is —F; or
  (III) a moiety of the Formula $R^4$—(C═O)—, wherein $R^4$ is:
    (a) heterocyclyl, which may optionally substituted by one or more: (i) ($R^{Ie}$)—O—(C═O)—, wherein $R^{Ie}$ is linear, branched or cyclic-alkyl of up to 6 carbon atoms; (ii) linear, branched or cyclic-alkyl of up to 6 carbon atoms, which alkyl may optionally be substituted with one or more aryl, which aryl may optionally be substituted with one or more halogens, and when a halogen-substituted aryl is selected, in some embodiments the halogen is preferably —F or —Br; (iii) aryl which may optionally be substituted with one or more halogens, and when halogen-substituted, in some embodiments the halogen is preferably —F or —Br; or (iv) heteroaryl, and in some embodiments when $R^4$— is selected to be heterocyclyle, it is preferably piperazinyl;
    (b) a spiroheterocyclyl comprising at least 1 heteroatom in each of the fused rings and up to 5 carbon atoms comprising each of the fused rings, and in some embodiments when said spiroheterocyclyl is selected, preferably each of the rings comprises one nitrogen as the heteroatom, which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) ($R^{If}$)—O—(C═O)—, wherein $R^{If}$ is -linear-, -branched-$C_{1-6}$-alkyl, or -cyclic-$C_{3-6}$-alkyl;
    (c) ($R^{Ig}$)$_2$N—, wherein $R^{Ig}$ is independently for each occurrence:
      (i) —H;
      (ii) aryl, which may optionally be substituted with one or more halogen, and in some embodiments, when halogen-substituted, preferably said halogen is —F;
      (iii) heteroaryl
      (iv) linear, branched or cyclic-alkyl of up to 6 carbon atoms, wherein said alkyl is optionally substituted on one or more carbon atoms thereof with one or more: (iva) aryl, which aryl may optionally be substituted with one or more halogens, and when halogen-substituted, in some embodiments the halogen is preferably —F or —Br; or (ivb) heteroaryl;

(v) both $R^{Ig}$ together with the nitrogen atom to which they are bonded form $C_{3-6}$-cyclo-amino, and wherein the alkyl portion of said cycloamino may optionally be substituted with one or more halogens; or (vi) one $R^{Ig}$ is a protecting group and the other is —H or linear, branched, or cyclic alkyl of up to 6 carbon atoms, and in some embodiments when one $R^{Ig}$ is a protecting group, it is preferably t-butoxy carbonyl.

In one aspect, the invention provides one or more compounds, or a pharmaceutically acceptable salt thereof, believed to have utility as an $A_{2A}$-receptor antagonist that have the structure of Formula IA:

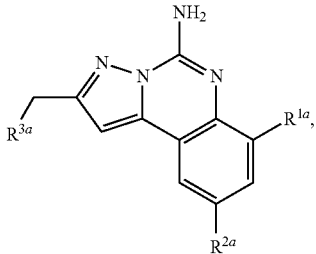

Formula IA

Formula IA, or a salt thereof,
wherein:
$R^{1a}$ is: (a)) —H; (b) halogen, and in some embodiments when selected to be halogen is preferably —F; or (c) linear, branched or cyclic alkoxy of up to 6 carbon atoms, which may optionally be substituted on one or more carbon atoms thereof with: (i) halogen; (ii) —OH; (iii) lower alkoxy; (iv) heterocyclyl which may optionally be substituted with aryl, wherein said aryl may optionally be substituted with: (iva) halogen or (ivb) linear, branched or cyclic-alkoxy of up to 4 carbon atoms which may optionally be substituted on a carbon atom thereof with lower alkoxy;

$R^{2a}$ is —H or, if $R^{1a}$ is selected to be —H, $R^{2a}$ is —H or halogen, and in some embodiments, when selected to be halogen, $R^{2a}$ is preferably —F; and $R^{3a}$ is:
(a) aryl, which may optionally be substituted with one or more:
  (i) halogen, and in some embodiments, when halogen-substituted, the halogen is preferably —F or —Cl;
  (ii) heterocyclyl, which may optionally be substituted by one or more: (iia) lower alkyl; (iib) ($R^{Ia}$)—O—(C=O)—, wherein $R^{Ia}$ is a linear-, branched-, or cyclic-alkyl of up to 6 carbon atoms; or (iic) —OH;
  (iii) ($R^{Ib}$)$_2$N—, wherein: $R^{Ib}$ is independently: —H; or is a linear-, branched-, or cyclic-alkyl of up to 6 carbon atoms, or wherein both $R^{Ib}$ are taken together with the nitrogen to which they are attached form a $C_{3-6}$-cyclo-amine;
  (iv) lower alkyl, which is optionally substituted with one or more: (iva) halogen, and when halogen substituted, preferably the halogen is —F or —Cl; (ivb) aryl; or (ivc) lower alkoxy which is optionally substituted with one or more halogen, and in some embodiments, when halogen substituted, preferably the halogen is —F or —Cl;
  (v) —CN;
  (vi) heteroaryl; which may optionally be substituted with one or more: (via) alkyl wherein said alkyl is a linear-, branched-, or cyclic-alkyl of up to 6 carbon atoms; or (vib) heterocyclyl, which heterocyclye may optionally be substituted by one or more linear-, branched-, or cyclic-alkyl of up to 6 carbon atoms; or
  (vii) $R^{Ic}$—O—, wherein $R^{Ic}$ is aryl or a linear, branched or cyclic-alkyl of up to 6 carbon atoms, which may optionally be substituted on any carbon atom thereof with one or more halogen, and in some embodiments when halogen substituted, preferably the halogen is —F or —Cl;

(b) heteroaryl, optionally substituted with one or more: (i) linear, branched or cyclic-alkyl of up to 6 carbon atoms; or (ii) heterocyclyl which is optionally substituted with linear, branched or cyclic-alkyl of up to 6 carbon atoms;

(c) heterocyclyl, optionally substituted with one or more:
  (i) —OH; or (ii) linear, branched or cyclic-alkyl of up to 6 carbon atoms;

(d) arylheterocyclyl, optionally substituted with one or more of: (i) =O; (ii) halogen, and in some embodiments, when halogen-substituted, preferably the halogen is —F; or (e) heteroarylheterocyclyl.

In some embodiments where $R^{3a}$ is selected to be aryl, $R^{3a}$ is preferably: (a) phenyl, which is optionally substituted with: (i) halogen; (ii) linear, branched or cyclic alkyl of up to 6 carbon atoms; (iii) alkoxy; (iv) cyano; or (v) —N($R^{3aa}$)$_2$, wherein $R^{3aa}$ is independently —H or linear, branched or cyclic alkyl of up to 6 carbon atoms; or (b) napthalenyl. In some embodiments where $R^{3a}$ is selected to be heteroaryl, $R^{3a}$ is preferably: (a) quinolinyl, optionally substituted with one or more linear, branched or cyclic alkyl substituents of up to 6 carbon atoms; (b) isoquinolinyl; (c) pyrimidinyl; (d) indazolyl; (e) pyrazolyl, optionally substituted with linear, branched or cyclic alkyl of up to 6 carbon atoms; (f) indolyl; (g) benzothiophenyl; (h) morpholinyl; (i) pyridinyl, optionally substituted with morphylinyl; or (j) thiazolyl, which is optionally substituted with piperazinyl; In some embodiments where $R^{3a}$ is selected to be heterocyclyl, $R^{3a}$ is preferably: (a) piperidinyl, optionally substituted with one or more linear, branched or cyclic alkyl substituents of up to 6 carbon atoms or hydroxyl substituents; (b) azetidinyl, optionally substituted with a hydroxyl substituent; (c) pyrrolidinyl; or (d) piperazinyl, which is optionally substituted with one or more aryl or phenyl substituents or linear, branched or cyclic alkyl substituent of up to 6 carbon atoms. In some embodiments where $R^{3a}$ is selected to be arylheterocyclyl, $R^{3a}$ is preferably pyrrolopyridinyl. In some embodiments where $R^{3a}$ is selected to be heteroarylheterocyclyl, $R^{3a}$ is preferably: (a) isoindolinyl, optionally substituted with fluorine; or (b) pyrrolopyridinyl.

In one aspect, the invention provides one or more compounds, or a pharmaceutically acceptable salt thereof, believed to have utility as an $A_{2A}$-receptor antagonist having the structure of Formula IB:

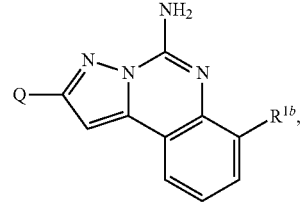

Formula IB

Formula IB, or a salt thereof,
wherein:
$R^{1b}$ is: (i) —H; (ii) halogen; or (iii) a linear, branched or cyclic alkoxy of up to 6 carbon atoms; and "Q" is a heteroaryl moiety comprising 2, 3, or 4 carbon atoms and one to 3 heteroatoms which are independently "N" or "O", and wherein Q may be bonded to the core of the compound through any available ring carbon therein or, if present, any available trivalent nitrogen therein, and wherein, said Q-moiety may optionally be substituted on any available ring carbon atom by:

(a) linear, branched or cyclic-alkyl of up to 6 carbon atoms, which may optionally be substituted with aryl or heteroaryl;

(b) $(R^{Id})_2N$—, wherein: $R^{Id}$ is —H or linear, branched or cyclic-alkyl of up to 6 carbon atoms, or wherein both $R^{Id}$ together with the nitrogen atom to which they are bonded form $C_{3-6}$-cyclo-amino, and wherein said alkyl may optionally be substituted on one or more carbon atoms thereof by phenyl which is optionally substituted by one or more halogens;

(c) aryl, and when selected to be aryl, in some embodiments it is preferably phenyl;

(d) heteroaryl; or (e) heterocyclyl, which may optionally be substituted with one or more:

(i) linear, branched or cyclic-alkyl of up to 6 carbon atoms; (ii) aryl, which may optionally be substituted with one or more halogen, and when halogen-substituted, preferably the halogen is —F In some embodiments when $R^{Ib}$ is selected to be a halogen, preferably it is —F. In some embodiments, when $R^{Ib}$ is selected to be alkoxy it is preferably methoxy or ethoxy, and when selected to be ethoxy, in some embodiments it is optionally substituted with a heterocyclyl, which is turn is optionally substituted by an aryl moiety or an aryl moiety which is in turn substituted by an alkoxy which may optionally be substituted by methoxy. In some embodiments when $R^{Ib}$ is selected to be a heterocyclyl-substituted alkoxy moiety, preferably said heterocyclyl substituent is piperazine. In some embodiments in which $R^{Ib}$ is selected to be a heterocyclyl-substituted alkoxy moiety, said heterocyclyl-moiety may be optionally be substituted with an aryl moiety, which in some embodiments is preferably phenyl, and which aryl moiety may be optionally substituted with a halogen or a linear, branched or cyclic alkyl moiety of up to 6 carbon atoms which is optionally substituted.

In some embodiments, preferably Q is a 1,2,4 oxadiazole or a 1,3,4 oxadiazole, bonded to the pyrazolo-quinzolinyl core via 1 ring carbon atom and optionally substituted on the other ring carbon atom with a moiety which is: (a) phenyl; (b) a linear, branched or cyclic alkyl moiety of up to 6 carbon atoms, optionally substituted by phenyl or quinolinyl; (c) morpholinyl; (d) piperazinyl, optionally substituted by aryl; or (e) amino of the formula —$N(R^{3b})_2$, wherein $R^{3b}$ is H or a linear, branched or cyclic alkyl moiety of up to 6 carbon atoms which is optionally substituted with phenyl, wherein said phenyl substituent may optionally be substituted with up to 3 fluorine atoms.

In one aspect, the invention provides one or more compounds, or a pharmaceutically acceptable salt thereof, believed to have utility as an $A_{2A}$-receptor antagonist that have the structure of Formula IC:

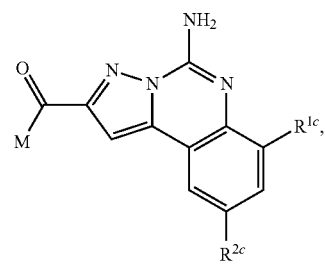

Formula IC

Formula IC, or a salt thereof,
wherein:
$R^{1c}$ is —H, —F, or a linear, branched or cyclic alkoxy moiety of up to 6 carbon atoms, and in some embodiments, when $R^{1c}$ is selected to be alkoxy, is preferably methoxy;
$R^{2c}$ is —H, or if $R^{1c}$ is selected to be —H, $R^{2c}$ may be —H or —F;
M is:

(a) heterocyclyl, which may optionally substituted by one or more: (i) $(R^{Ie})$—O—(C=O)—, wherein $R^{Ie}$ is linear, branched or cyclic-alkyl of up to 6 carbon atoms; (ii) linear, branched or cyclic-alkyl of up to 6 carbon atoms, which alkyl may optionally be substituted with one or more aryl, which aryl may optionally be substituted with one or more halogens, and when a halogen-substituted aryl is selected, in some embodiments the halogen is preferably —F or —Br; (iii) aryl which may optionally be substituted with one or more halogens, and when halogen-substituted, in some embodiments the halogen is preferably —F or —Br; or (iv) heteroaryl, and in some embodiments when $R^4$— is selected to be heterocyclyl, it is preferably piperazinyl;

(b) a spiroheterocyclyl comprising at least 1 heteroatom in each of the fused rings and up to 5 carbon atoms comprising each of the fused rings, and in some embodiments when said spiroheterocyclyl is selected, preferably each of the rings comprises one nitrogen as the heteroatom, and which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) $(R^{If})$—O—(C=O)—, wherein $R^{If}$ is -linear-, -branched-, or -cyclic-alkyl of up to 6 carbon atoms;

(c) $(R^{Ig})_2N$—, wherein: $R^{Ig}$ is independently for each occurrence:
(i) —H;
(ii) aryl, which may optionally be substituted with one or more halogen, and in some embodiments, when halogen-substituted, preferably said halogen is —F;
(iii) heteroaryl;
(iv) linear, branched or cyclic-alkyl of up to 6 carbon atoms, wherein said alkyl is optionally substituted on one or more carbon atoms thereof with one or more: (iva) aryl, which aryl may optionally be substituted with one or more halogens, and when halogen-substituted, in some embodiments the halogen is preferably —F or —Br; or (ivb) heteroaryl;
(v) both $R^{Ig}$ together with the nitrogen atom to which they are bonded form $C_{3-6}$-cyclo-amino, and wherein the alkyl portion of said cycloamino may optionally be substituted with one or more halogens; or
(vi) one $R^{Ig}$ is a protecting group and the other is —H or linear, branched, or cyclic alkyl of up to 6 carbon atoms, and in some embodiments when one $R^{Ig}$ is a protecting group, it is preferably t-butoxy carbonyl.

In another aspect, the invention is a pharmaceutical formulation comprising at least one compound, or a pharmaceutically acceptable salt thereof, of Formulae A, B or C. In another aspect the invention is directed to the use of compounds of Formulae A, B and C, the pharmaceutically acceptable salts thereof, and pharmaceutical formulations comprising these compounds or their salts, in the potential treatment of movement disorders in which $A_{2A}$ receptors are involved.

In some aspects the present invention is the provision of a method of treating central nervous system disorders by administering to a subject in need thereof a therapeutic amount of at least one compound of Formulae A, B, or C, or a pharmaceutically acceptable salt of such compounds.

DETAILED DESCRIPTION OF THE INVENTION

As mentioned above, the invention provides compounds having the structure of Formula I, or a pharmaceutically acceptable salt of any thereof:

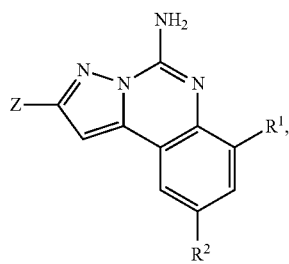

Formula I wherein:
"Z", $R^1$ and $R^2$ are defined herein.

Compounds of the invention and formulations comprising compounds of the invention are believed to be useful in providing potential treatment, management, alleviation or amelioration of conditions or disease states which can be treated, managed, alleviated or ameliorated by specific antagonism of A2a receptors. Conditions for which such therapy may be provided include, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential, or are believed to have the potential, for use in preventing or lessening the effect of drugs that cause movement disorders As used herein, unless otherwise specified, the term "A2a receptor antagonist" (equivalently, A2a antagonist) means a compound exhibiting a potency ($IC_{50}$) of less than about 1 µM when assayed in accordance with the procedure described herein. Preferred compounds exhibit at least 10-fold selectivity for antagonizing the A2a receptor over any other andenosine receptor (e.g., A1, A1b, or A3).

In some embodiments, compounds of Formula I are preferably:
7-methoxy-2-(oxazol-5-yl)pyrazolo[1,5-c]quinazolin-5-amine;
7-(2-(4-(2,4-difluorophenyl)piperazin-1-yl)ethoxy)-2-(furan-2-yl)pyrazolo[1,5-c]quinazolin-5-amine;
2-(furan-2-yl)-7-(2-(4-(4-(2-methoxyethoxy)phenyl)piperazin-1-yl)ethoxy)pyrazolo[1,5-c]quinazolin-5-amine;
2-benzyl-7-methoxypyrazolo[1,5-c]quinazolin-5-amine;
2-(4-fluorobenzyl)-7-methoxypyrazolo[1,5-c]quinazolin-5-amine;
2-(2,4-difluorobenzyl)-7-methoxypyrazolo[1,5-c]quinazolin-5-amine;
7-methoxy-2-(naphthalen-1-ylmethyl)pyrazolo[1,5-c]quinazolin-5-amine;
7-methoxy-2-(4-(piperidin-1-yl)benzyl)pyrazolo[1,5-c]quinazolin-5-amine;
7-methoxy-2-(quinolin-8-ylmethyl)pyrazolo[1,5-c]quinazolin-5-amine;
7-methoxy-2-(pyrimidin-5-ylmethyl)pyrazolo[1,5-c]quinazolin-5-amine;
2-(4-(dimethylamino)benzyl)-7-methoxypyrazolo[1,5-c]quinazolin-5-amine;
7-methoxy-2-(4-(4-methylpiperazin-1-yl)benzyl)pyrazolo[1,5-c]quinazolin-5-amine;
7-methoxy-2-((2-(4-methylpiperazin-1-yl)thiazol-4-yl)methyl)pyrazolo[1,5-c]quinazolin-5-amine;
7-methoxy-2-(quinolin-4-ylmethyl)pyrazolo[1,5-c]quinazolin-5-amine;
7-methoxy-2-(quinolin-5-ylmethyl)pyrazolo[1,5-c]quinazolin-5-amine;
2-(1H-indazol-5-yl)methyl)-7-methoxypyrazolo[1,5-c]quinazolin-5-amine;
7-methoxy-2-(2-(trifluoromethyl)benzyl)pyrazolo[1,5-c]quinazolin-5-amine;
7-methoxy-2-(2-morpholinobenzyl)pyrazolo[1,5-c]quinazolin-5-amine;
7-methoxy-2-(2-(piperazin-1-yl)benzyl)pyrazolo[1,5-c]quinazolin-5-amine;
7-methoxy-2-((2-morpholinopyridin-3-yl)methyl)pyrazolo[1,5-c]quinazolin-5-amine;
7-methoxy-2-(2-(morpholinomethyl)benzyl)pyrazolo[1,5-c]quinazolin-5-amine;
7-methoxy-2-(4-morpholinobenzyl)pyrazolo[1,5-c]quinazolin-5-amine;
7-methoxy-2-(3-morpholinobenzyl)pyrazolo[1,5-c]quinazolin-5-amine;
tert-butyl 4-(4-((5-amino-7-methoxypyrazolo[1,5-c]quinazolin-2-yl)methyl)phenyl)piperazine-1-carboxylate;
7-methoxy-2-(4-(piperazin-1-yl)benzyl)pyrazolo[1,5-c]quinazolin-5-amine;
2-(2-(4-ethylpiperazin-1-yl)benzyl)-7-methoxypyrazolo[1,5-c]quinazolin-5-amine;
1-(2-((5-amino-7-methoxypyrazolo[1,5-c]quinazolin-2-yl)methyl)benzyl)-4-methylpiperidin-4-ol;
1-(2-((5-amino-7-methoxypyrazolo[1,5-c]quinazolin-2-yl)methyl)benzyl)azetidin-3-ol;
7-methoxy-2-(2-(pyrrolidin-1-ylmethyl)benzyl)pyrazolo[1,5-c]quinazolin-5-amine;
2-(2-fluorobenzyl)-7-methoxypyrazolo[1,5-c]quinazolin-5-amine;
2-(3-fluorobenzyl)-7-methoxypyrazolo[1,5-c]quinazolin-5-amine;
7-methoxy-2-(2-methoxybenzyl)pyrazolo[1,5-c]quinazolin-5-amine;
7-methoxy-2-(4-methoxybenzyl)pyrazolo[1,5-c]quinazolin-5-amine;
7-methoxy-2-(3-methoxybenzyl)pyrazolo[1,5-c]quinazolin-5-amine;
7-methoxy-2-(4-(trifluoromethyl)benzyl)pyrazolo[1,5-c]quinazolin-5-amine;
7-methoxy-2-(3-(trifluoromethyl)benzyl)pyrazolo[1,5-c]quinazolin-5-amine;

7-methoxy-2-((1-methyl-1H-pyrazol-4-yl)methyl)pyrazolo[1,5-c]quinazolin-5-amine;
2-(2-chloro-6-fluorobenzyl)-7-methoxypyrazolo[1,5-c]quinazolin-5-amine;
7-methoxy-2-(2,3,4-trifluorobenzyl)pyrazolo[1,5-c]quinazolin-5-amine;
2-(2,3-difluorobenzyl)-7-methoxypyrazolo[1,5-c]quinazolin-5-amine;
2-(1H-indol-4-yl)methyl)-7-methoxypyrazolo[1,5-c]quinazolin-5-amine;
2-(2,6-difluorobenzyl)-7-methoxypyrazolo[1,5-c]quinazolin-5-amine;
2-(2,3-dichlorobenzyl)-7-methoxypyrazolo[1,5-c]quinazolin-5-amine;
2-(isoquinolin-5-ylmethyl)-7-methoxypyrazolo[1,5-c]quinazolin-5-amine;
2-(2-chlorobenzyl)-7-methoxypyrazolo[1,5-c]quinazolin-5-amine;
7-methoxy-2-(2-(trifluoromethoxy)benzyl)pyrazolo[1,5-c]quinazolin-5-amine;
2-(2-(dimethylamino)benzyl)-7-methoxypyrazolo[1,5-c]quinazolin-5-amine;
7-methoxy-2-(3-(methoxymethyl)benzyl)pyrazolo[1,5-c]quinazolin-5-amine;
2-(3-chlorobenzyl)-7-methoxypyrazolo[1,5-c]quinazolin-5-amine;
2-((5-amino-7-methoxypyrazolo[1,5-c]quinazolin-2-yl)methyl)benzonitrile;
2-(2-(benzyloxy)benzyl)-7-methoxypyrazolo[1,5-c]quinazolin-5-amine;
3-((5-amino-7-methoxypyrazolo[1,5-c]quinazolin-2-yl)methyl)benzonitrile;
2-(benzo[b]thiophen-7-ylmethyl)-7-methoxypyrazolo[1,5-c]quinazolin-5-amine;
2-(3-(3,5-dimethyl-1H-pyrazol-1-yl)benzyl)-7-methoxypyrazolo[1,5-c]quinazolin-5-amine;
2-(2-(difluoromethoxy)benzyl)-7-methoxypyrazolo[1,5-c]quinazolin-5-amine;
4-((5-amino-7-methoxypyrazolo[1,5-c]quinazolin-2-yl)methyl)isoindolin-1-one;
7-methoxy-2-((2-methyl quinolin-5-yl)methyl)pyrazolo[1,5-c]quinazolin-5-amine;
2-(3-(1H-pyrazol-1-yl)benzyl)-7-methoxypyrazolo[1,5-c]quinazolin-5-amine;
2-(3-fluoro-2-methylbenzyl)-7-methoxypyrazolo[1,5-c]quinazolin-5-amine;
7-methoxy-2-((2-methyl quinolin-8-yl)methyl)pyrazolo[1,5-c]quinazolin-5-amine;
3-((5-amino-7-methoxypyrazolo[1,5-c]quinazolin-2-yl)methyl)-2-fluorobenzonitrile;
3-((5-amino-7-methoxypyrazolo[1,5-c]quinazolin-2-yl)methyl)-5-chlorobenzonitrile;
2-(2-(1H-pyrazol-1-yl)benzyl)-7-methoxypyrazolo[1,5-c]quinazolin-5-amine;
2-(2,5-difluorobenzyl)-7-methoxypyrazolo[1,5-c]quinazolin-5-amine;
2-(3,5-difluorobenzyl)-7-methoxypyrazolo[1,5-c]quinazolin-5-amine;
7-methoxy-2-((4-phenylpiperazin-1-yl)methyl)pyrazolo[1,5-c]quinazolin-5-amine;
1-((5-amino-7-methoxypyrazolo[1,5-c]quinazolin-2-yl)methyl)azetidin-3-ol;
2-((5-fluoroisoindolin-2-yl)methyl)-7-methoxypyrazolo[1,5-c]quinazolin-5-amine;
2-((5,7-dihydro-6H-pyrrolo[3,4-b]pyridin-6-yl)methyl)-7-methoxypyrazolo[1,5-c]quinazolin-5-amine;
(5-amino-7-methoxypyrazolo[1,5-c]quinazolin-2-yl)(4-(pyridin-2-yl)piperazin-1-yl)methanone;
(5-amino-7-methoxypyrazolo[1,5-c]quinazolin-2-yl)(4-benzylpiperazin-1-yl)methanone;
(5-amino-7-methoxypyrazolo[1,5-c]quinazolin-2-yl)(piperidin-1-yl)methanone;
(5-amino-7-methoxypyrazolo[1,5-c]quinazolin-2-yl)(4-(4-fluorobenzyl)piperazin-1-yl)methanone;
(5-amino-7-methoxypyrazolo[1,5-c]quinazolin-2-yl)(pyrrolidin-1-yl)methanone;
tert-butyl 4-(5-amino-7-methoxypyrazolo[1,5-c]quinazoline-2-carbonyl)piperazine-1-carboxylate;
(5-amino-7-methoxypyrazolo[1,5-c]quinazolin-2-yl)(piperazin-1-yl)methanone;
5-amino-N-(2,4-difluorobenzyl)-7-methoxypyrazolo[1,5-c]quinazoline-2-carboxamide;
(5-amino-7-methoxypyrazolo[1,5-c]quinazolin-2-yl)(4-(2,4-difluorophenyl)piperazin-1-yl)methanone;
5-amino-N-(4-bromo-2-fluorobenzyl)-7-methoxypyrazolo[1,5-c]quinazoline-2-carboxamide;
5-amino-7-methoxy-N-phenylpyrazolo[1,5-c]quinazoline-2-carboxamide;
5-amino-N-benzyl-7-methoxy-N-methylpyrazolo[1,5-c]quinazoline-2-carboxamide;
5-amino-7-methoxy-N-methyl-N-(quinolin-8-ylmethyl)pyrazolo[1,5-c]quinazoline-2-carboxamide;
tert-butyl 8-(5-amino-7-methoxypyrazolo[1,5-c]quinazoline-2-carbonyl)-2,8-diazaspiro[4.5]decane-2-carboxylate;
(5-amino-7-methoxypyrazolo[1,5-c]quinazolin-2-yl)(2,8-diazaspiro[4.5]decan-8-yl)methanone;
tert-butyl 7-(5-amino-7-methoxypyrazolo[1,5-c]quinazoline-2-carbonyl)-2,7-diazaspiro[4.4]nonane-2-carboxylate;
(5-amino-7-methoxypyrazolo[1,5-c]quinazolin-2-yl)(2,7-diazaspiro[4.4]nonan-2-yl)methanone;
1-(7-(5-amino-7-methoxypyrazolo[1,5-c]quinazoline-2-carbonyl)-2,7-diazaspiro[4.4]nonan-2-yl)ethan-1-one;
methyl 7-(5-amino-7-methoxypyrazolo[1,5-c]quinazoline-2-carbonyl)-2,7-diazaspiro[4.4]nonane-2-carboxylate;
(5-amino-7-methoxypyrazolo[1,5-c]quinazolin-2-yl)(7-ethyl-2,7-diazaspiro[4.4]nonan-2-yl)methanone;
(5-amino-7-methoxypyrazolo[1,5-c]quinazolin-2-yl)(7-benzyl-2,7-diazaspiro[4.4]nonan-2-yl)methanone;
5-amino-7-methoxy-N-(quinolin-8-ylmethyl)pyrazolo[1,5-c]quinazoline-2-carboxamide;
7-methoxy-2-(3-phenyl-1,2,4-oxadiazol-5-yl)pyrazolo[1,5-c]quinazolin-5-amine;
2-(3-benzyl-1,2,4-oxadiazol-5-yl)-7-methoxypyrazolo[1,5-c]quinazolin-5-amine;
2-(quinolin-8-ylmethyl)pyrazolo[1,5-c]quinazolin-5-amine;
2-(quinolin-4-ylmethyl)pyrazolo[1,5-c]quinazolin-5-amine;
2-(2-morpholinobenzyl)pyrazolo[1,5-c]quinazolin-5-amine;
2-(2-(morpholinomethyl)benzyl)pyrazolo[1,5-c]quinazolin-5-amine;
2-(5-(quinolin-8-yl)-1,3,4-oxadiazol-2-yl)pyrazolo[1,5-c]quinazolin-5-amine;
7-methoxy-2-(5-(quinolin-7-ylmethyl)-1,3,4-oxadiazol-2-yl)pyrazolo[1,5-c]quinazolin-5-amine;
7-methoxy-2-(5-(quinolin-8-yl)-1,3,4-oxadiazol-2-yl)pyrazolo[1,5-c]quinazolin-5-amine;
7-methoxy-2-(5-morpholino-1,3,4-oxadiazol-2-yl)pyrazolo[1,5-c]quinazolin-5-amine;
7-methoxy-2-(5-(4-phenylpiperazin-1-yl)-1,3,4-oxadiazol-2-yl)pyrazolo[1,5-c]quinazolin-5-amine;
5-(5-amino-7-methoxypyrazolo[1,5-c]quinazolin-2-yl)-N-(2,4-difluorobenzyl)-1,3,4-oxadiazol-2-amine;

2-benzyl-9-fluoropyrazolo[1,5-c]quinazolin-5-amine;
9-fluoro-2-(quinolin-8-ylmethyl)pyrazolo[1,5-c]quinazolin-5-amine;
9-fluoro-2-(2-morpholinobenzyl)pyrazolo[1,5-c]quinazolin-5-amine;
9-fluoro-2-((2-morpholinopyridin-3-yl)methyl)pyrazolo[1,5-c]quinazolin-5-amine;
2-benzyl-7-fluoropyrazolo[1,5-c]quinazolin-5-amine;
7-fluoro-2-(quinolin-8-ylmethyl)pyrazolo[1,5-c]quinazolin-5-amine;
(5-amino-7-fluoropyrazolo[1,5-c]quinazolin-2-yl)(4-(pyridin-2-yl)piperazin-1-yl)methanone;
(5-amino-7-fluoropyrazolo[1,5-c]quinazolin-2-yl)(4-(2,4-difluorophenyl)piperazin-1-yl)methanone;
(5-amino-9-fluoropyrazolo[1,5-c]quinazolin-2-yl)(4-(2,4-difluorophenyl)piperazin-1-yl)methanone;
(5-amino-9-fluoropyrazolo[1,5-c]quinazolin-2-yl)(4-(pyridin-2-yl)piperazin-1-yl)methanone;
7-fluoro-2-(5-(quinolin-8-yl)-1,3,4-oxadiazol-2-yl)pyrazolo[1,5-c]quinazolin-5-amine; or
7-fluoro-2-(5-(quinolin-7-ylmethyl)-1,3,4-oxadiazol-2-yl)pyrazolo[1,5-c]quinazolin-5-amine,
or a pharmaceutically acceptable salt of any thereof.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

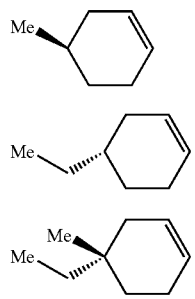

Illus-I

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula IA that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"moiety" is used herein to refer to a specific group of atoms that have a collective characteristic and in radical form constitute a substituent appended to a molecule, for example, conceptively abstracting a proton from a pyridine ring carbon atom yields a heteroaryl moiety (pyridinyl) which may be attached to another molecule as a substituent via a bond to the ring carbon atom from which the proton was conceptively abstracted.

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula IA to a compound of Formula IA, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the moieties enumerated as substituents (or, where a list of substituents are not specifically enumerated, the substituents specified elsewhere in this application) for the particular type of substrate to which said substituent is appended, provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution by a moiety is described (e.g. "optionally substituted") the term means that if substituents are present, one or more of the enumerated (or default) moieties listed as optional substituents for the specified substrate can be present on the substrate in a bonding position normally occupied by the default substituent, for example, a hydrogen atom on an alkyl chain can be substituted by one of the optional substiuents, in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

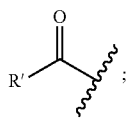

non-limiting examples of suitable acyl groups include formyl, acetyl, propanoyl, 2-methylpropanoyl, butanoyl and cyclohexanoyl;

"alkoxy" means a moiety of the structure: alkyl-O— (i.e., the bond to the substrate moiety is through the oxygen), wherein the alkyl portion of the moiety is a linear, branched or cyclic alkyl, as defined below; non-limiting examples of suitable alkoxy groups include methoxy, ethoxy, n-propoxy, isopropoxy, n-butoxy, cyclopentoxy, cyclohexoxy, n-hexoxy and n-heptoxy;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a cyclic aliphatic moiety comprising at least 3 carbon atoms (the minimum number necessary to provide a cyclic moiety) up to the maximum number of specified carbon atoms. Examples of cycloalkyl moieties include, but are not limited to, cyclopropyl, cyclobutyl, cyclopentyl or cyclohexyl. The term "cycl" cyclic-alkyl (equivalently "cycloalkyl") also includes non-aromatic, fused multicyclic ring system comprising up to about 20 carbon atoms which may optionally be substituted as defined herein for "alkyl" generally. Suitable multicyclic cycloalkyls are, for example, but are not limited to: 1-decalin; norbornyl; adamantly; and the like;

any of the afore-mentioned linear-, branched-, or cyclic-alkyl moieties which are defined to be "optionally substituted" means that one or more of the carbon atoms in the structure can have one or more of the C—H bonds associated therewith substituted with a moiety selected from the list of possible substituents called out in the definition of the moiety, and in like manner where the phrase "substituted" appears in the definition of the moiety, it means that at least 1 hydrogen atom has been replaced where a C—H bond would be with at least one of the enumerated substituents in the list of substituents called out in the definition of the alkyl moiety;

"lower alkyl" means a linear, branched, or cycloalkyl moiety comprising up to about 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"lower alkoxy" means [R—O-] where "R" is a linear, branched, or cycloalkyl moiety comprising up to about 6 carbon atoms; examples of suitable lower alkoxy groups include, but are not limited to, methoxy, ethoxy, n-propoxy, isopropoxy, cyclopropoxy, n-butoxy, t-butoxy, cyclobutoxy, n-pentoxy, isopentoxy, neopentoxy, cyclopentoxy, methoxy-cyclopentane, and the like "aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected substituents as called out where the moiety is defined. Non-limiting examples of suitable aryl groups include phenyl

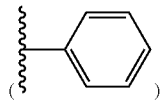 [SMILES: *c1ccccc1]

and naphthyl

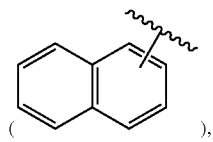

wherein bonding can be through any of the carbons in the aromatic ring, and wherein any ring carbon atoms not participating in a bond to the substrate may have bonded to it a substituent other than —H, independently selected in each instance from the list of substituents called out in an enumerated list of substituents presented in defining the moiety;

A substituent designated as "halogen" or "halogen atom" means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halogen, for example, where the alkyl is selected to be methyl, the term " . . . which is optionally substituted with —F . . . " means —CH$_3$, —CFH$_2$, —CF$_2$H and —CF$_3$ unless the number of halogen substituents is limited numerically;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; a "heteroaryl" moiety can be optionally substituted at chemically available ring atoms by one or more independently selected substituents as called out where the moiety is defined; wherein the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety. In some heteroaryl moietis, the hetero atom can be oxidized, for example, a nitrogen atom of a heteroaryl moiety can be optionally oxidized to the corresponding N-oxide; non-limiting examples of heteroaryl moieties where bonding to the substrate can be via any available ring carbon atom, include: pyridyl-,

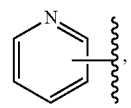

thiopenyl-

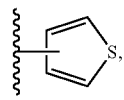

furanyl-,

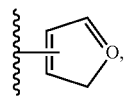

quionlinyl

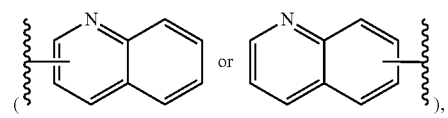

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

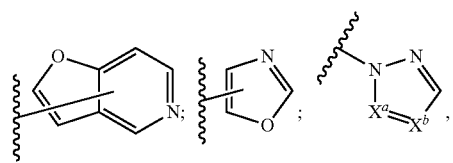

where one of $X^a$ or $X^b$ is —CH= or —N= and the other is —CH=;

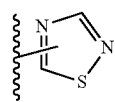

and the like (wherein, unless otherwise noted, bonded to the substrate through any available ring atom that results in a stable bonding arrangement);

"heteroarylcycloalkyl" means a moiety having a heteroaryl-portion fused to two carbon atoms of a cycloalkyl portion, wherein ring carbon atoms in either portion may be optionally substituted with one or more substituents called out in an enumerated list of substituents presented in defining the moiety, and wherein the heteroaryl portion comprises up to 8 carbon atoms and up to three hetero atoms which are independently nitrogen, oxygen or sulfur, and the cycloalkyl portion comprises up to 10 carbon atoms. In the same manner, "heteroarylheterocycloalkyl" means a moiety in which the fused cycloalkyl portion has, in addition to saturated carbon, one or more heteroatoms comprising the ring. In some embodiments it is preferred for the cycloalkyl portion to comprise up to 6 carbon atoms. Examples of heteroarylcycloalkyl moieties include, but are not limited to: 6,7-dihydro-5H-cyclopenta[b]pyrazine and 5,6,7,8-tetrahydroquinoline. When the term is used with "spiro", e.g. "heteroarylspirocycloalkyl" it means that the alkyl portion of the moiety contains one carbon in common with a substrate to which it is attached forming a spirocyloalkyl structure, for example, the structure:

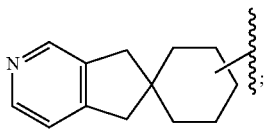

wherein the structure is bonded to a substrate through the cycloalkyl portion with which the heteroarylcycloalkyl moiety forms the spirocyloalkyl structure.

"arylheterocycl" "arylheterocyclyl" or "arylheterocycloalkyl" means a moiety having an aryl portion, as aryl is defined herein, wherein two adjacent carbon atoms in the ring are fused to a heterocycloalkyl portion comprising at least one carbon atom and up to 3 heteroatoms. Examples of arylheterocycloalkyl moieties include, but are not limited to, tetrahydroquinoxaline, tetrahydroquinoline, dihydrocyclopentapyridine, and the like. Unless specified otherwise, bonding of an arylheterocycloalkyl or heteroarylcycloalkyl moiety to a substrate may be through any aryl, heteroaryl, heterocycloalkyl or cycloalkyl ring atom present in the moiety.

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example, nitrogen, e.g. a piperidyl-(5-carbon, 1-nitrogen, 6-member saturated ring) moiety or a pyrrolidinyl-moiety (4-carbon, 1-nitrogen, 5-member saturated ring), a moiety containing a single oxygen atom in the ring (e.g. a furanyl moiety or a tetrahydropyranyl moiety), or sulfur (e.g. a tetrahydrothiophenyl moiety or a tetrahydrothiopyranyl moiety); and wherein the heteroatoms can be alone or in combination provided that the moiety does not contain adjacent oxygen and/or sulfur atoms present in the ring system; preferred heterocyclyl moieties contain up to 10 ring atoms and may be monocyclic, bicyclic, or spiro-configurations; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide (SO$_2$); non-limiting examples of suitable monocyclic heterocyclyl rings include piperidyl, pyrrolidinyl, piperazinyl, morpholinyl -

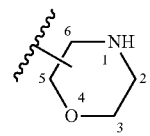

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

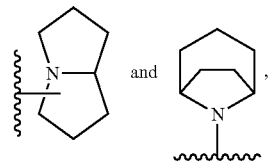

and the like.

"tetrahydropyranyl" moiety means a 6-member cyclic ether of the formula:

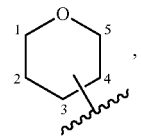

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" refers to a heterocyclyl moiety having the core structure:

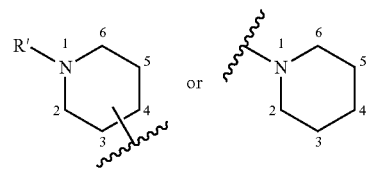

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

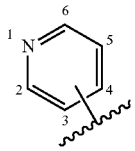

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinoline" refers to a heteroaryl moiety having the core structure:

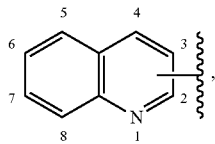

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

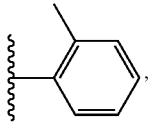

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula IA, and of the salts, solvates and prodrugs of the compounds of Formula IA, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

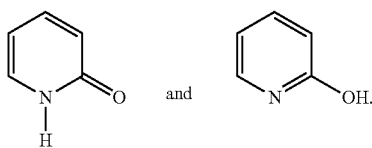 [SMILES: O=c1cccc[nH]1 ; Oc1ccccn1]

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the protected compound is subjected to particular reaction conditions aimed at modifying another region of the molecule. Suitable protecting groups are known, for example, as by reference to standard textbooks, for example, T. W. Greene et al, Protective Groups in organic Synthesis (1991), Wiley, New York.

When a variable (e.g., aryl, heterocyclyl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, and $^{36}$Cl, $^{123}$I and $^{125}$I. It will be appreciated that other isotopes may be incorporated by know means also.

Certain isotopically-labeled compounds of the invention (e.g., those labeled with $^3$H, $^{11}$C and $^{14}$C) are recognized as being particularly useful in compound and/or substrate tissue distribution assays using a variety of known techniques. Tritiated (i.e., $^3$H) and carbon-14 (i.e., $^{14}$C) isotopes are particularly preferred for their ease of preparation and detection. Further, substitution of a naturally abundant isotope with a heavier isotope, for example, substitution of protium with deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

In one aspect, as mentioned above, the present invention provides pharmaceutical compositions for use in antagonizing $A_{2A}$ receptors, believed to be useful in treating, amolerating, or managing central nervous system (CNS) disorders, for example, movement disorders associated with Parkinson's disease or the treatment or management thereof, wherein the compositions comprising at least one compound, or pharmaceutically acceptable salt thereof, of Formulae G, A, B or C, as defined herein and at least one other excipient (described below).

It will be appreciated that pharmaceutical formulations of the invention may comprise more than one compound of the invention, for example, the combination of two or three compounds of the invention, each present in such a composition by adding to the formulation the desired amount of the compound in a pharmaceutically acceptably pure form. It will be appreciated also that in formulating compositions of the invention, a composition may comprise, in addition to one or more of compounds of the invention, one or more other compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific antagonism of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, antagonism of adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, for example, a compound of Formula I, or a salt thereof, and at least one pharmaceutically acceptable carrier (described below). It will be appreciated that pharmaceutically formulations of the invention may comprise more than one compound of the invention, or a salt thereof, for example, the combination of two or three compounds of the invention, each present by adding to the formulation the desired amount of the compound or a salt thereof which has been isolated in a pharmaceutically acceptably pure form.

As mentioned above, administration of a compound of the invention to effect antagonism of A2a receptor sites, which is believed to be beneficial in the treatment of central nervous system diseases is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As mentioned above, administration of a compound of the invention is preferably accomplished by incorporating a pharmaceutical formulation comprising the compound into a dosage form, for example, one of the above-described dosage forms. In general a dosage form comprises an effective amount of at least one compound of the invention (for example, 1, 2 or 3, or 1 or 2, or 1, and usually 1 compound of the invention), or a pharmaceutically acceptable salt thereof along with other excipients and vehicles adapting it to administration via the intended route. Methods for determining safe and effective administration of compounds which are pharmaceutically active, for example, a compound of Formula I, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. The amount of composition desired to be administered in one daily period can be a single dose or can be divided into two to four doses per day.

In general, in what ever form administered, the dosage form administered will contain an amount of at least one compound of the invention, or a salt thereof, which will provide a therapeutically effective serum level of the compound in some form for a period of at least 2 hours, more preferably at least four hours or longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, i) L-DOPA; ii) DOPA decarboxylase inghibitors; and iii) COMT inhibitors.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

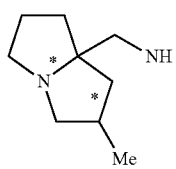

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

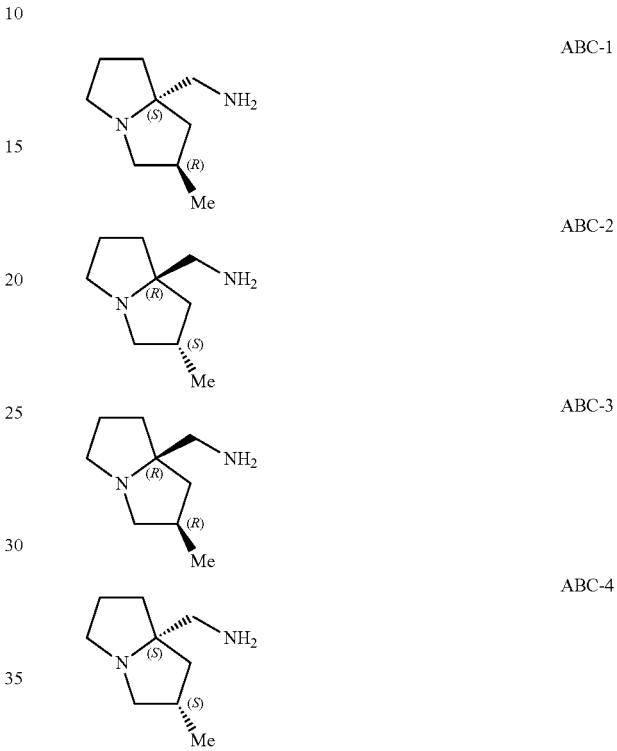

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine, In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, astrisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as a limitation of the invention to these specifically exemplified compounds.

EXAMPLES

Example 1: Preparation of 7-(2-(4-(2,4-difluorophenyl)piperazin-1-yl)ethoxy)-2-(furan-2-yl)pyrazolo[1,5-c]quinazolin-5-amine (Exp 1)

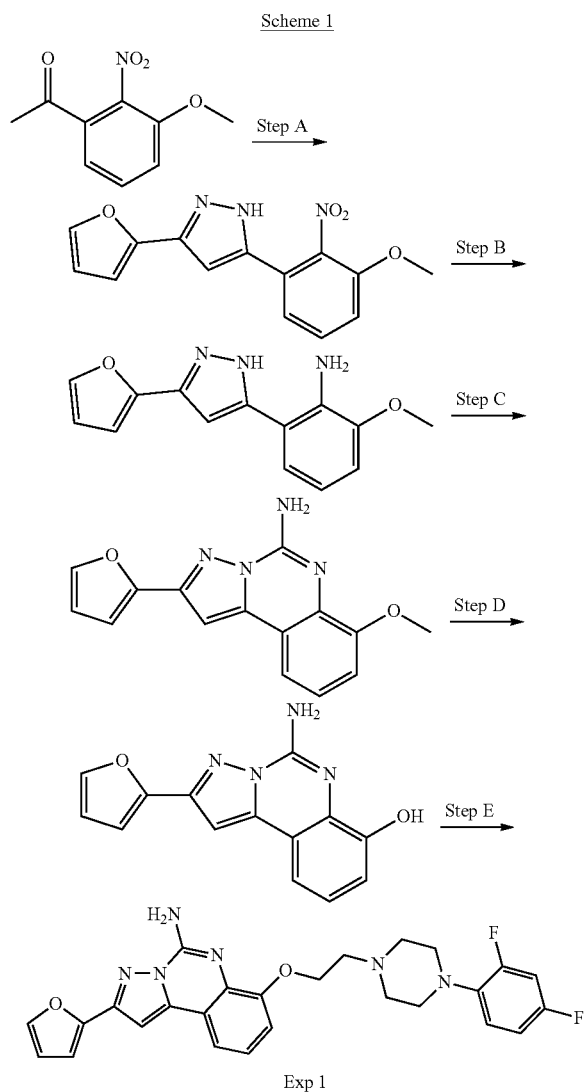

Exp 1

Step A: 3-(furan-2-yl)-5-(3-methoxy-2-nitrophenyl)-1H-pyrazole

To a solution of 1-(3-methoxy-2-nitrophenyl)ethanone (2.0 g, 10.0 mmol) in toluene (50 ml) was added 1M sol. of LiHMDS in THF (10.8 ml, 10.8 mmol) at 0° C. Then 2-furoyl chloride (670 mg, 5.0 mmol) was added at 0° C. The reaction mixture was stirred at room temperature for 5 min. AcOH (1.0 ml) was added to the reaction mixture followed by EtOH (10.0 ml) and THF (2.5 ml). Once the reaction mixture was back into solution, hydrazine hydrate (5.0 g, 0.1 mol) was added with stirring causing the mixture to warm up. After stirring for 2 h at 85° C., the reaction mixture was poured into 1N NaOH. The organic phase was extracted with EtOAc, dried over $MgSO_4$, filtered, and then concentrated in vacuo. The resulting residue was purified by flash chromatography (2:1 Hex:EtOAc) to yield the desired product.

Step B: 2-(3-(furan-2-yl)-1H-pyrazol-5-yl)-6-methoxyaniline

To a solution of 3-(furan-2-yl)-5-(3-methoxy-2-nitrophenyl)-1H-pyrazole (0.4 g, 1.4 mmol) in MeOH (40 ml) was added a catalytic amount of Pd/C. The reaction mixture was degassed then stirred under $H_2$ atmosphere for 2 hours, then diluted with $CH_2Cl_2$. The mixture was filtered through a pad of celite, concentrated in vacuo and the resulting residue was purified by flash chromatography (3:1 Hex:EtOAc) to yield the desired product.

Step C: 2-(furan-2-yl)-7-methoxypyrazolo[1,5-c]quinazolin-5-amine

To a solution of 2-(3-(furan-2-yl)-1H-pyrazol-5-yl)-6-methoxyaniline (100 mg, 0.4 mmol) in EtOH (5 ml) was added a 3M sol. of BrCN in DCM (0.2 ml, 66.7 mmol). Reaction mixture was stirred at room temperature for 4 h and the concentrated in vacuo. The resulting residue was purified by Prep TLC (10:1 $CH_2Cl_2$:MeOH) to yield the desired product.

Step D: 5-amino-2-(furan-2-yl)pyrazolo[1,5-c]quinazolin-7-ol

To a solution of 2-(furan-2-yl)-7-methoxypyrazolo[1,5-c]quinazolin-5-amine (100 mg, 0.4 mmol) was added 1M sol. of $BBr_3$ in DCM (1.4 ml, 1.4 mmol). Reaction mixture was stirred in a sealed tube at 60° C. for 12 h. The reaction mixture was cooled to room temperature and diluted with $CH_2Cl_2$ and $H_2O$. The organic layer was separated and dried over $MgSO_4$, filtered, and then concentrated in vacuo. The resulting residue was purified by Prep TLC (10:1 $CH_2Cl_2$:MeOH) to yield the desired product.

Step E: 7-(2-(4-(2,4-difluorophenyl)piperazin-1-yl)ethoxy)-2-(furan-2-yl)pyrazolo[1,5-c]quinazolin-5-amine (Exp 1)

To a solution of 5-amino-2-(furan-2-yl)pyrazolo[1,5-c]quinazolin-7-ol (28 mg, 0.1 mmol) in DMF (2 ml) was added 1-(2-chloroethyl)-4-(2,4-difluorophenyl)piperazine (55 mg, 0.2 mmol) and $K_2CO_3$ (44 mg, 0.3 mmol). This reaction mixture was stirred at 80° C. for 1 hour, then purified by reverse phase HPLC to yield the desired product as a TFA salt. LC/MS=491 [M+1].

The compounds presented in Table I were prepared by using methods described in Example 1.

TABLE I

| Ex No. | Structure | Name | LC-MS |
|---|---|---|---|
| EX-2 | 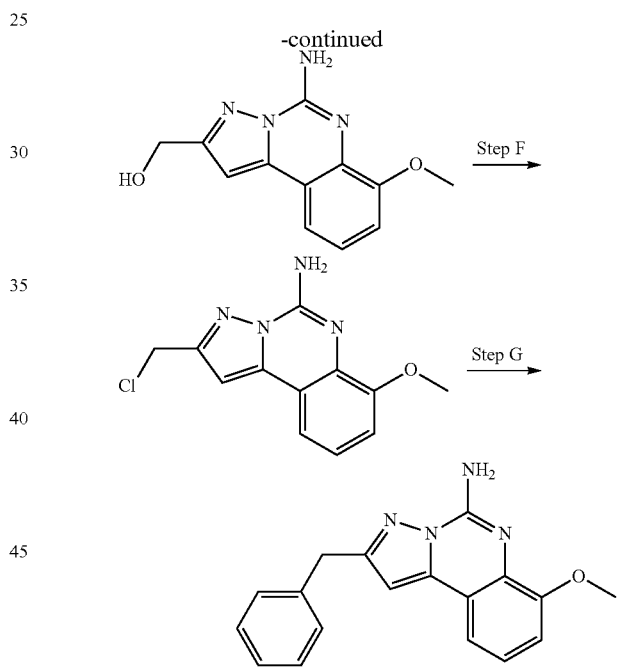 | 7-methoxy-2-(oxazol-5-yl)pyrazolo[1,5-c]quinazolin-5-amine | 282 [M + 1]. |
| EX-3 | 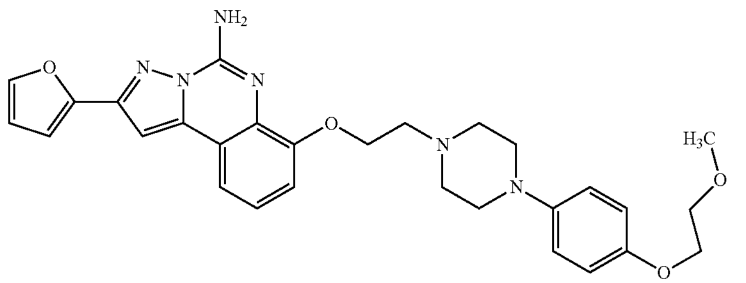 [SMILES: COCCOc1ccc(N2CCN(CCOc3cccc4c3nc(N)n3nc(-c5ccco5)cc43)CC2)cc1] | 2-(furan-2-yl)-7-(2-(4-(4-(2-methoxyethoxy)phenyl)piperazin-1-yl)ethoxy)pyrazolo[1,5-c]quinazolin-5-amine | 529 [M + 1]. |

Example 2: Preparation of 2-benzyl-7-methoxy-pyrazolo[1,5-c]quinazolin-5-amine (Ex-4)

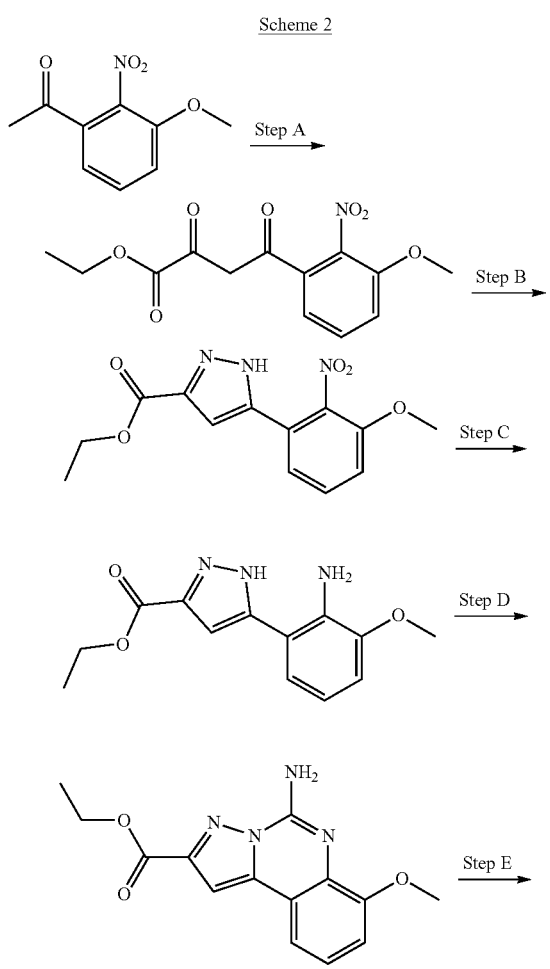

Step A: ethyl 4-(3-methoxy-2-nitrophenyl)-2,4-dioxobutanoate

To a solution of 1M sol. of LiHMDS in THF (86.0 ml, 86.0 mmol) and THF (100 ml) was added a solution of 1-(3-methoxy-2-nitrophenyl)ethanone (15.3 g, 78.4 mmol) in THF (50 ml). The reaction mixture was stirred at −78° C. for 15 min and then diethyl oxalate (12.7 ml, 94.0 mmol) was added slowly to the mixture. The resulting mixture was warmed up to room temperature and stirred for 1 hour, then acidified with 1N HCl and diluted with EtOAc. The organic layer was separated, dried over $MgSO_4$, filtered, and concentrated in vacuo. The residue was purified by flash chromatography (1:1 Hex:EtOAc) to yield the desired product.

Step B: ethyl 5-(3-methoxy-2-nitrophenyl)-1H-pyrazole-3-carboxylate

To a solution of ethyl 4-(3-methoxy-2-nitrophenyl)-2,4-dioxobutanoate (42.5 g, 0.14 mol) in AcOH (300 ml) was added slowly the hydrazine hydrate (5.1 g, 0.16 mol). The reaction mixture was stirred at 80° C. for 2 hours, cooled to room temperature, then concentrated in vacuo and used as prepared in the next step without further purification.

Step C: ethyl 5-(2-amino-3-methoxyphenyl)-1H-pyrazole-3-carboxylate

To a solution of crude ethyl 5-(3-methoxy-2-nitrophenyl)-1H-pyrazole-3-carboxylate prepared in the previous step (45.0 g, 0.17 mol) in MeOH (400 ml) was added a catalytic amount of Pd/C. The reaction mixture was degassed and then stirred under $H_2$ atmosphere for 12 h. The resulting mixture was diluted with $CH_2Cl_2$ and filtered through a pad of celite. The filtrate was concentrated in vacuo and used as prepared in the next step without further purification.

Step D: ethyl 5-amino-7-methoxypyrazolo[1,5-c]quinazoline-2-carboxylate

To a solution of crude 2-(3-(furan-2-yl)-1H-pyrazol-5-yl)-6-methoxyaniline prepared in the previous step (13 g, 50.0 mmol) in EtOH (100 ml) was added 3M sol. of BrCN in DCM (50 ml, 0.15 mol). Reaction mixture was stirred at room temperature over 2d. The resulting precipitate was filtered and dried in vacuo and used as prepared in the next step without further purification.

Step E: (5-amino-7-methoxypyrazolo[1,5-c]quinazolin-2-yl)methanol

To a solution of ethyl 5-amino-7-methoxypyrazolo[1,5-c]quinazoline-2-carboxylate (5.5 g, 19.2 mmol) in THF (300 ml) was added 2M sol. of $LiBH_4$ in THF (19.2 ml, 38.0 mmol). The reaction mixture was stirred at room temperature for 3 days, then quenched slowly with $H_2O$. The resulting mixture was acidified with 1N HCl and concentrated in vacuo to remove most of the THF. The resulting aqueous mixture was basified with 1N NaOH. The resulting precipitate was filtered and dried and used as prepared in the next step without further purification.

Step F: 2-(chloromethyl)-7-methoxypyrazolo[1,5-c]quinazolin-5-amine

To a solution of (5-amino-7-methoxypyrazolo[1,5-c]quinazolin-2-yl)methanol (2.4 g, 10.0 mmol) in $CH_2Cl_2$ (25 ml) was added thionyl chloride (25.0 ml, 0.34 mol). The reaction mixture was stirred at room temperature for 1 hour, concentrated in vacuo with a boiling water bath and used as prepared in the next step without further purification.

Step G: 2-benzyl-7-methoxypyrazolo[1,5-c]quinazolin-5-amine (Ex-4)

To a solution of 2-(chloromethyl)-7-methoxypyrazolo[1,5-c]quinazolin-5-amine prepared in the previous step (25 mg, 0.1 mmol) in dimethoxyethane (2.5 ml) and $H_2O$ (1.0 ml) was added phenyl boronic acid (35.0 ml, 0.3 mmol), dppf (19.0 mg, 0.02 mmol), and $Na_2CO_3$ (61.0 mg, 0.6 mmol). The resulting mixture was stirred in a sealed tube at 80° C. for 12 hours, cooled to room temperature, then diluted with $CH_2Cl_2$. The resulting mixture was washed with $NaHCO_3$ (sat.). The organic layer was separated, dried over $MgSO_4$, filtered, and then concentrated in vacuo. The resulting residue was purified by reverse phase HPLC to yield the desired product as the TFA salt. The identity of the product was confirmed by LC/MS=305 [M+1]. Activity was determined via the protocol described herein: A2a Ki=9 nm.

The compounds presented in Table II were prepared using the procedure described in Example 2 with appropriate precursor reagents.

TABLE II

| Expl. No. | Structure | Name | LC-MS |
|---|---|---|---|
| Ex-5 | 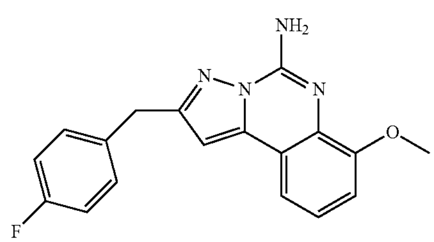 [SMILES: COc1cccc2c1nc(N)n1nc(Cc3ccc(F)cc3)cc21] | 2-(4-fluorobenzyl)-7-methoxypyrazolo[1,5-c]quinazolin-5-amine | 323 [M + 1]. |
| Ex-6 | 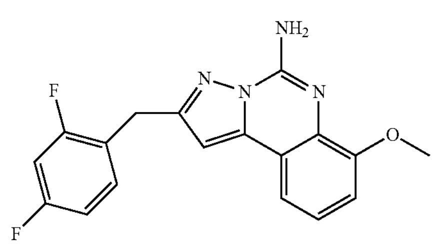 [SMILES: COc1cccc2c1nc(N)n1nc(Cc3ccc(F)cc3F)cc21] | 2-(2,4-difluorobenzyl)-7-methoxypyrazolo[1,5-c]quinazolin-5-amine | 341 [M + 1]. |

TABLE II-continued

| Expl. No. | Structure | Name | LC-MS |
|---|---|---|---|
| Ex-7 | 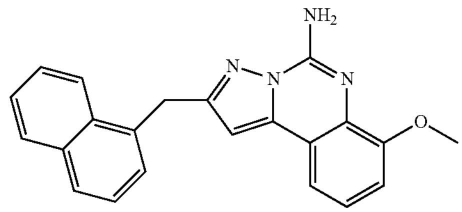 [SMILES: COc1cccc2c1nc(N)n1nc(Cc3cccc4ccccc34)cc21] | 7-methoxy-2-(naphthalen-1-ylmethyl)pyrazolo[1,5-c]quinazolin-5-amine | 355 [M + 1]. |
| Ex-8 | 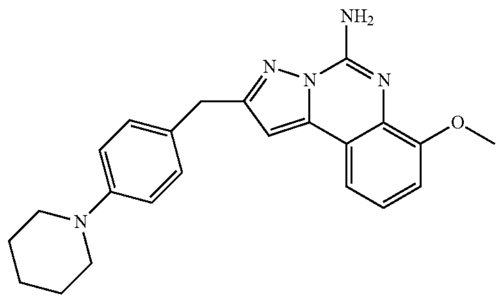 [SMILES: COc1cccc2c1nc(N)n1nc(Cc3ccc(N4CCCCC4)cc3)cc21] | 7-methoxy-2-(4-(piperidin-1-yl)benzyl)pyrazolo[1,5-c]quinazolin-5-amine | 388 [M + 1]. |
| Ex-9 | 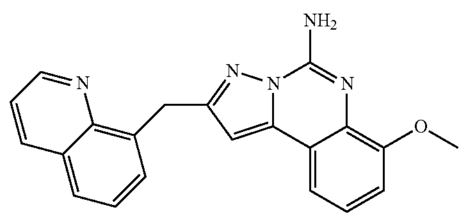 [SMILES: COc1cccc2c1nc(N)n1nc(Cc3cccc4cccnc34)cc21] | 7-methoxy-2-(quinolin-8-ylmethyl)pyrazolo[1,5-c]quinazolin-5-amine | 356 [M + 1]. |
| Ex-10 | 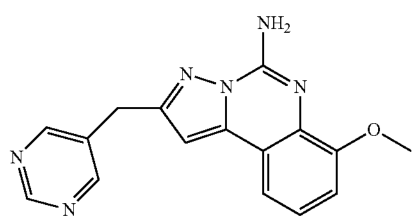 [SMILES: COc1cccc2c1nc(N)n1nc(Cc3cncnc3)cc21] | 7-methoxy-2-(pyrimidin-5-ylmethyl)pyrazolo[1,5-c]quinazolin-5-amine | 307 [M + 1]. |
| Ex-11 | 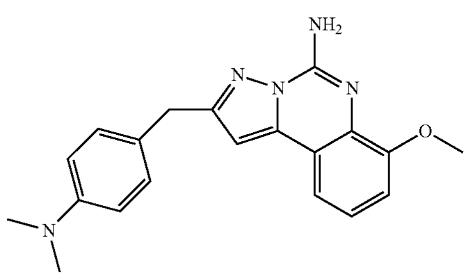 | 2-(4-(dimethylamino)benzyl)-7-methoxypyrazolo[1,5-c]quinazolin-5-amine | 348 [M + 1]. |
| Ex-12 | 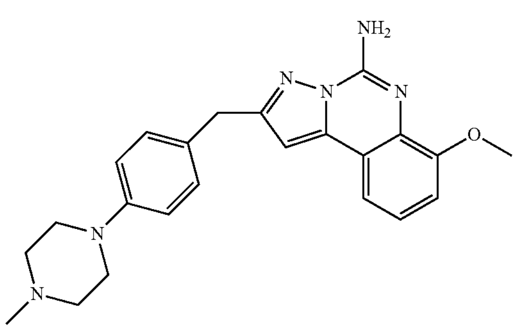 | 7-methoxy-2-(4-(4-methylpiperazin-1-yl)benzyl)pyrazolo[1,5-c]quinazolin-5-amine | 403 [M + 1]. |

TABLE II-continued

| Expl. No. | Structure | Name | LC-MS |
|---|---|---|---|
| Ex-13 | 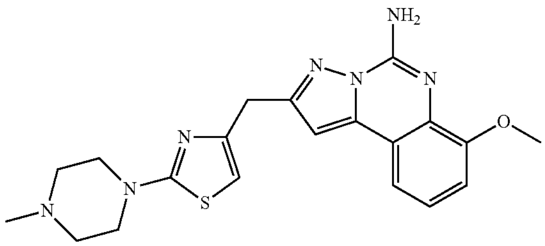 | 7-methoxy-2-((2-(4-methylpiperazin-1-yl)thiazol-4-yl)methyl)pyrazolo[1,5-c]quinazolin-5-amine | 410 [M + 1]. |
| Ex-14 | 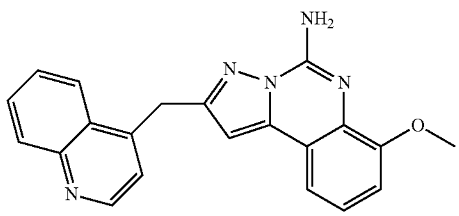 | 7-methoxy-2-(quinolin-4-ylmethyl)pyrazolo[1,5-c]quinazolin-5-amine | 356 [M + 1]. |
| Ex-15 | 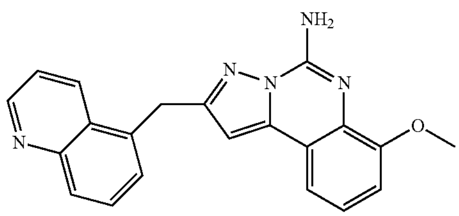 | 7-methoxy-2-(quinolin-5-ylmethyl)pyrazolo[1,5-c]quinazolin-5-amine | 356 [M + 1]. |
| Ex-16 | 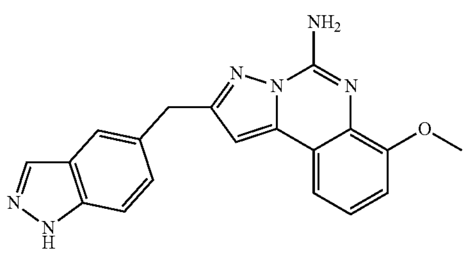 [SMILES: COc1cccc2c1nc(N)n1nc(Cc3ccc4[nH]ncc4c3)cc21] | 2-((1H-indazol-5-yl)methyl)-7-methoxypyrazolo[1,5-c]quinazolin-5-amine | 345 [M + 1]. |
| Ex-17 | 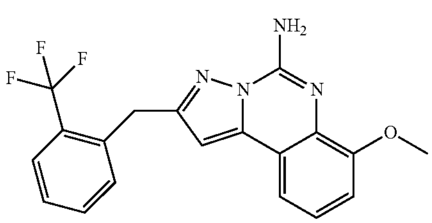 [SMILES: COc1cccc2c1nc(N)n1nc(Cc3ccccc3C(F)(F)F)cc21] | 7-methoxy-2-(2-(trifluoromethyl)benzyl)pyrazolo[1,5-c]quinazolin-5-amine | 373 [M + 1]. |
| Ex-18 | 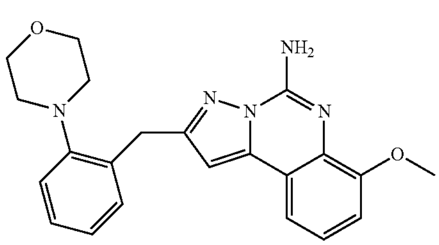 [SMILES: COc1cccc2c1nc(N)n1nc(Cc3ccccc3N3CCOCC3)cc21] | 7-methoxy-2-(2-morpholinobenzyl)pyrazolo[1,5-c]quinazolin-5-amine | 390 [M + 1]. |

TABLE II-continued

| Expl. No. | Structure | Name | LC-MS |
|---|---|---|---|
| Ex-19 | 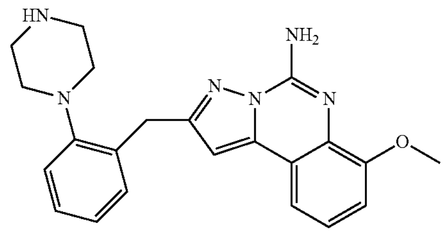 [SMILES: COc1cccc2c1nc(N)n1nc(Cc3ccccc3N3CCNCC3)cc21] | 7-methoxy-2-(2-(piperazin-1-yl)benzyl)pyrazolo[1,5-c]quinazolin-5-amine | 389 [M + 1]. |
| Ex-20 | 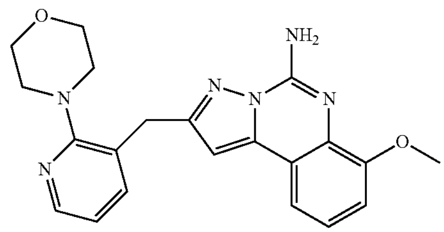 [SMILES: COc1cccc2c1nc(N)n1nc(Cc3cccnc3N3CCOCC3)cc21] | 7-methoxy-2-((2-morpholinopyridin-3-yl)methyl)pyrazolo[1,5-c]quinazolin-5-amine | 391 [M + 1]. |
| Ex-21 | 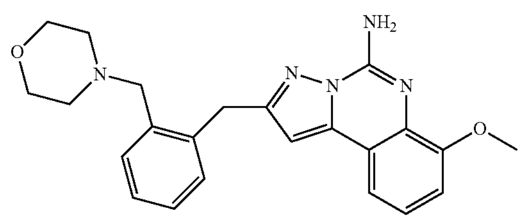 [SMILES: COc1cccc2c1nc(N)n1nc(Cc3ccccc3CN3CCOCC3)cc21] | 7-methoxy-2-(2-(morpholinomethyl)benzyl)pyrazolo[1,5-c]quinazolin-5-amine | 404 [M + 1]. |
| Ex-22 | 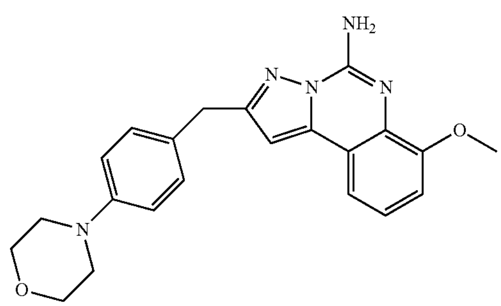 [SMILES: COc1cccc2c1nc(N)n1nc(Cc3ccc(N4CCOCC4)cc3)cc21] | 7-methoxy-2-(4-morpholinobenzyl)pyrazolo[1,5-c]quinazolin-5-amine | 390 [M + 1]. |
| Ex-23 | 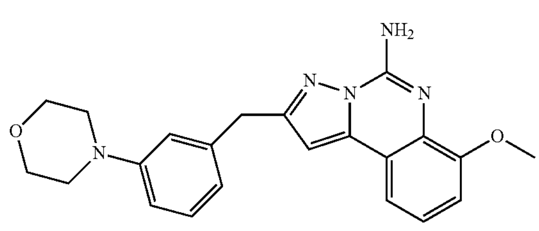 [SMILES: COc1cccc2c1nc(N)n1nc(Cc3cccc(N4CCOCC4)c3)cc21] | 7-methoxy-2-(3-morpholinobenzyl)pyrazolo[1,5-c]quinazolin-5-amine | 390 [M + 1]. |

TABLE II-continued

| Expl. No. | Structure | Name | LC-MS |
|---|---|---|---|
| Ex-24 | 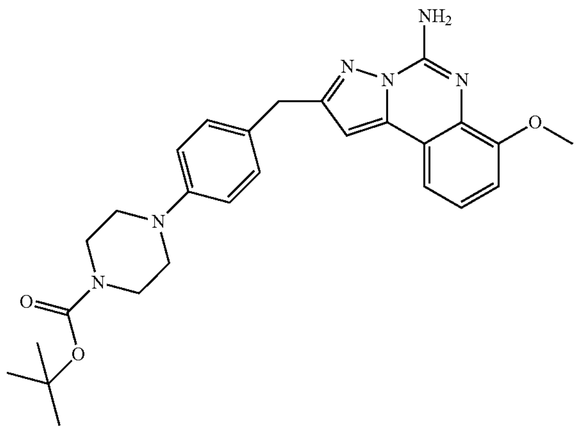 [SMILES: COc1cccc2c1nc(N)n1nc(Cc3ccc(N4CCN(C(=O)OC(C)(C)C)CC4)cc3)cc21] | tert-butyl 4-(4-((5-amino-7-methoxypyrazolo[1,5-c]quinazolin-2-yl)methyl)phenyl)piperazine-1-carboxylate | 489 [M + 1]. |
| Ex-25 | 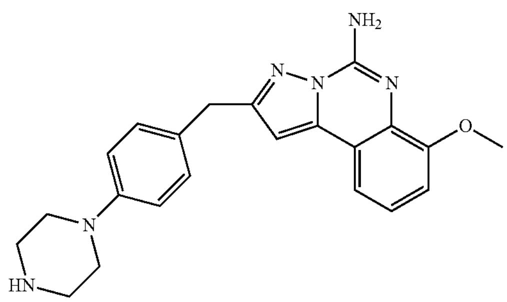 [SMILES: COc1cccc2c1nc(N)n1nc(Cc3ccc(N4CCNCC4)cc3)cc21] | 7-methoxy-2-(4-(piperazin-1-yl)benzyl)pyrazolo[1,5-c]quinazolin-5-amine | 389 [M + 1]. |
| Ex-26 | 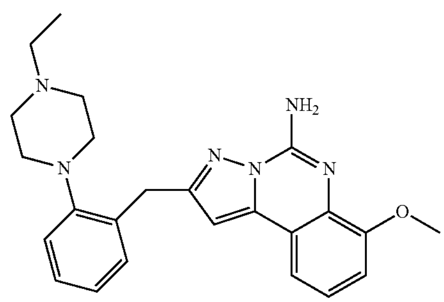 [SMILES: CCN1CCN(c2ccccc2Cc2cc3c4cccc(OC)c4nc(N)n3n2)CC1] | 2-(2-(4-ethylpiperazin-1-yl)benzyl)-7-methoxypyrazolo[1,5-c]quinazolin-5-amine | 417 [M + 1]. |
| Ex-27 | 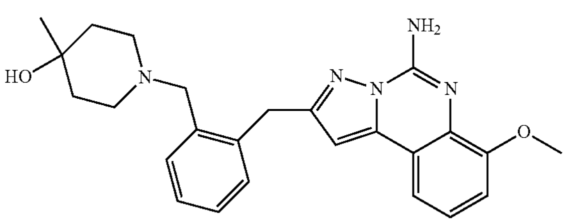 [SMILES: COc1cccc2c1nc(N)n1nc(Cc3ccccc3CN3CCC(C)(O)CC3)cc21] | 1-(2-((5-amino-7-methoxypyrazolo[1,5-c]quinazolin-2-yl)methyl)benzyl)-4-methylpiperidin-4-ol | 432 [M + 1]. |
| Ex-28 | 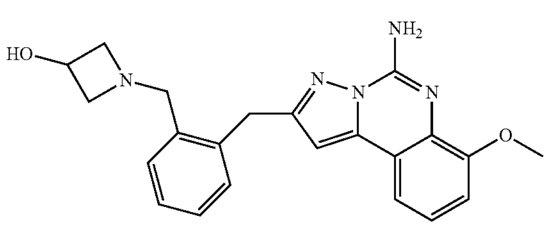 [SMILES: COc1cccc2c1nc(N)n1nc(Cc3ccccc3CN3CC(O)C3)cc21] | 1-(2-((5-amino-7-methoxypyrazolo[1,5-c]quinazolin-2-yl)methyl)benzyl)azetidin-3-ol | 390 [M + 1] |

TABLE II-continued

| Expl. No. | Structure | Name | LC-MS |
|---|---|---|---|
| Ex-29 | 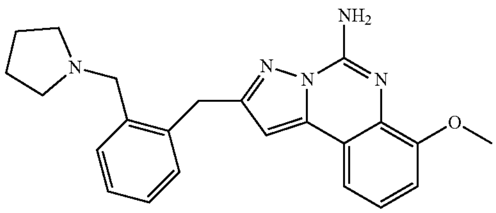 [SMILES: COc1cccc2c1nc(N)n1nc(Cc3ccccc3CN3CCCC3)cc21] | 7-methoxy-2-(2-(pyrrolidin-1-ylmethyl)benzyl)pyrazolo[1,5-c]quinazolin-5-amine | 388 [M + 1] |
| Ex-30 | | 2-(2-fluorobenzyl)-7-methoxypyrazolo[1,5-c]quinazolin-5-amine | 323 [M + 1] |
| Ex-30 | | 2-(2-fluorobenzyl)-7-methoxypyrazolo[1,5-c]quinazolin-5-amine | 323 |
| Ex-31 | 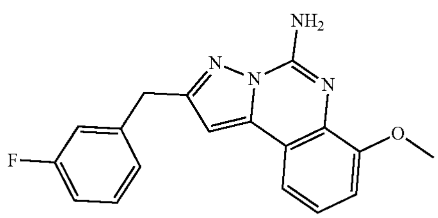 [SMILES: COc1cccc2c1nc(N)n1nc(Cc3cccc(F)c3)cc21] | 2-(3-fluorobenzyl)-7-methoxypyrazolo[1,5-c]quinazolin-5-amine | 323 [M + 1] |
| Ex-32 | 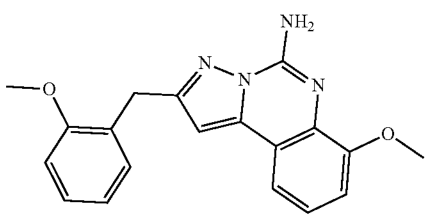 | 7-methoxy-2-(2-methoxybenzyl)pyrazolo[1,5-c]quinazolin-5-amine | 335 [M + 1] |
| Ex-33 | 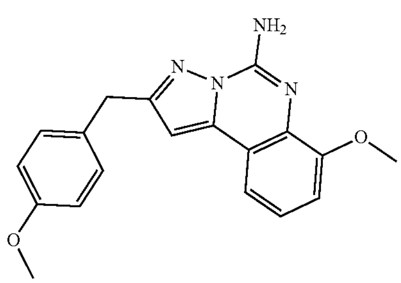 [SMILES: COc1ccc(Cc2cc3c4cccc(OC)c4nc(N)n3n2)cc1] | 7-methoxy-2-(4-methoxybenzyl)pyrazolo[1,5-c]quinazolin-5-amine | 335 [M + 1] |
| Ex-34 | 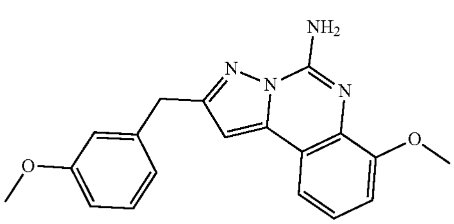 | 7-methoxy-2-(3-methoxybenzyl)pyrazolo[1,5-c]quinazolin-5-amine | 335 [M + 1] |

TABLE II-continued

| Expl. No. | Structure | Name | LC-MS |
|---|---|---|---|
| Ex-35 | 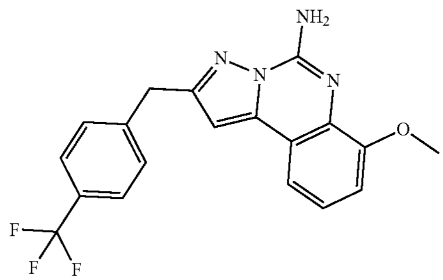 [SMILES: COc1cccc2c1nc(N)n1nc(Cc3ccc(C(F)(F)F)cc3)cc21] | 7-methoxy-2-(4-(trifluoromethyl)benzyl)pyrazolo[1,5-c]quinazolin-5-amine | 373 [M + 1] |
| Ex-36 | 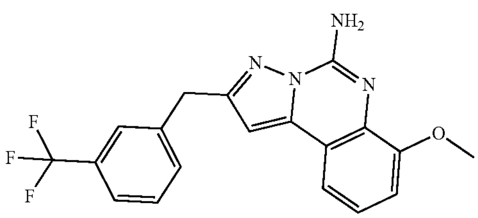 [SMILES: COc1cccc2c1nc(N)n1nc(Cc3cccc(C(F)(F)F)c3)cc21] | 7-methoxy-2-(3-(trifluoromethyl)benzyl)pyrazolo[1,5-c]quinazolin-5-amine | 373 [M + 1] |
| Ex-37 | 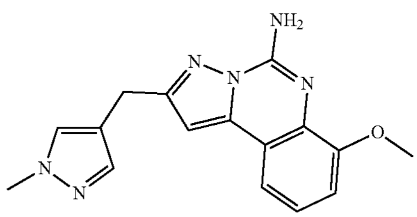 | 7-methoxy-2-((1-methyl-1H-pyrazol-4-yl)methyl)pyrazolo[1,5-c]quinazolin-5-amine | 309 [M + 1] |
| Ex-38 | 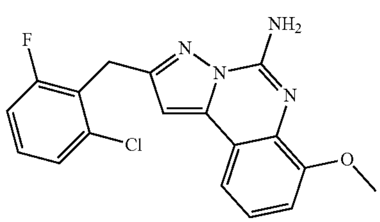 [SMILES: COc1cccc2c1nc(N)n1nc(Cc3c(F)cccc3Cl)cc21] | 2-(2-chloro-6-fluorobenzyl)-7-methoxypyrazolo[1,5-c]quinazolin-5-amine | 357 [M + 1] |
| Ex-39 | 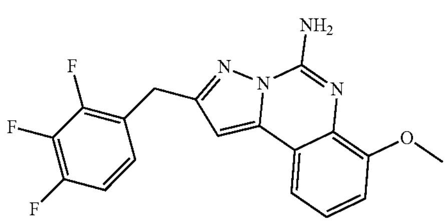 [SMILES: COc1cccc2c1nc(N)n1nc(Cc3ccc(F)c(F)c3F)cc21] | 7-methoxy-2-(2,3,4-trifluorobenzyl)pyrazolo[1,5-c]quinazolin-5-amine | 359 [M + 1] |
| Ex-40 | 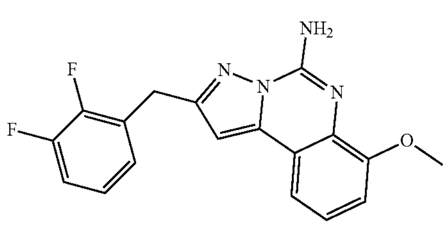 [SMILES: COc1cccc2c1nc(N)n1nc(Cc3cccc(F)c3F)cc21] | 2-(2,3-difluorobenzyl)-7-methoxypyrazolo[1,5-c]quinazolin-5-amine | 341 [M + 1] |

TABLE II-continued

| Expl. No. | Structure | Name | LC-MS |
|---|---|---|---|
| Ex-41 | 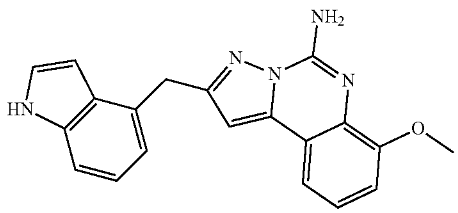 [SMILES: COc1cccc2c1nc(N)n1nc(Cc3cccc4[nH]ccc34)cc21] | 2-((1H-indol-4-yl)methyl)-7-methoxypyrazolo[1,5-c]quinazolin-5-amine | 344 [M + 1] |
| Ex-42 | 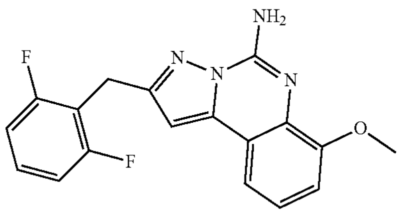 [SMILES: COc1cccc2c1nc(N)n1nc(Cc3c(F)cccc3F)cc21] | 2-(2,6-difluorobenzyl)-7-methoxypyrazolo[1,5-c]quinazolin-5-amine | 341 [M + 1] |
| Ex-43 | 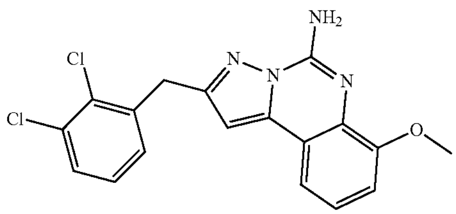 [SMILES: COc1cccc2c1nc(N)n1nc(Cc3cccc(Cl)c3Cl)cc21] | 2-(2,3-dichlorobenzyl)-7-methoxypyrazolo[1,5-c]quinazolin-5-amine | 373 [M + 1] |
| Ex-44 | 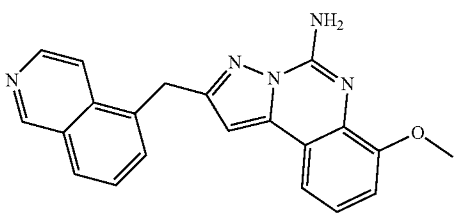 [SMILES: COc1cccc2c1nc(N)n1nc(Cc3cccc4cnccc34)cc21] | 2-(isoquinolin-5-ylmethyl)-7-methoxypyrazolo[1,5-c]quinazolin-5-amine | 356 [M + 1] |
| Ex-45 | 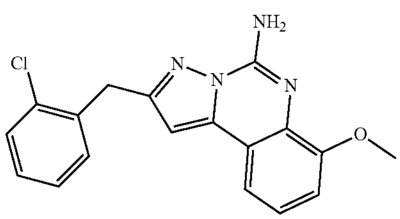 [SMILES: COc1cccc2c1nc(N)n1nc(Cc3ccccc3Cl)cc21] | 2-(2-chlorobenzyl)-7-methoxypyrazolo[1,5-c]quinazolin-5-amine | 339 [M + 1] |
| Ex-46 | 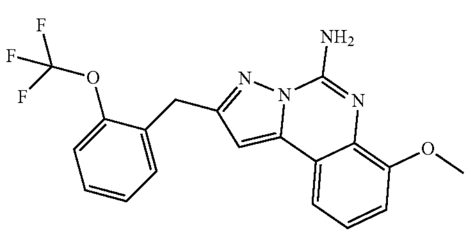 [SMILES: COc1cccc2c1nc(N)n1nc(Cc3ccccc3OC(F)(F)F)cc21] | 7-methoxy-2-(2-(trifluoromethoxy)benzyl)pyrazolo[1,5-c]quinazolin-5-amine | 389 [M + 1] |
| Ex-47 | 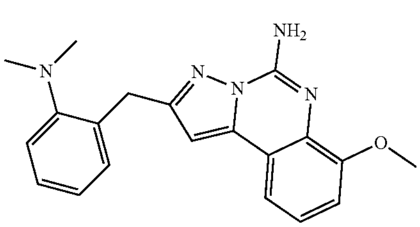 | 2-(2-(dimethylamino)benzyl)-7-methoxypyrazolo[1,5-c]quinazolin-5-amine | 348 [M + 1] |

TABLE II-continued

| Expl. No. | Structure | Name | LC-MS |
|---|---|---|---|
| Ex-48 | 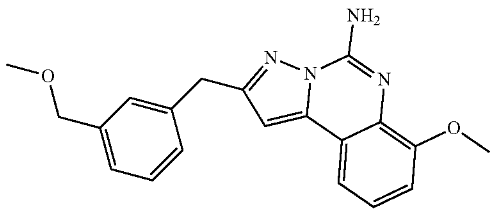 | 7-methoxy-2-(3-(methoxymethyl)benzyl)pyrazolo[1,5-c]quinazolin-5-amine | 349 [M + 1] |
| Ex-49 | 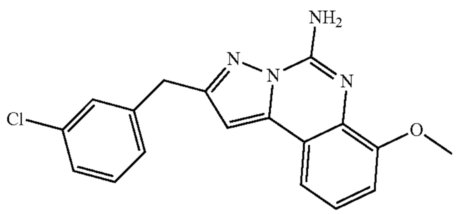 [SMILES: COc1cccc2c1nc(N)n1nc(Cc3cccc(Cl)c3)cc21] | 2-(3-chlorobenzyl)-7-methoxypyrazolo[1,5-c]quinazolin-5-amine | 339 [M + 1] |
| Ex-50 | 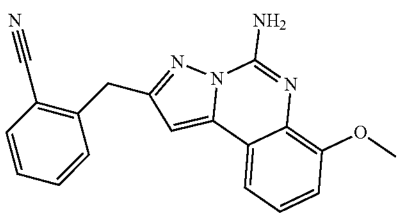 [SMILES: COc1cccc2c1nc(N)n1nc(Cc3ccccc3C#N)cc21] | 2-((5-amino-7-methoxypyrazolo[1,5-c]quinazolin-2-yl)methyl)benzonitrile | 330 [M + 1] |
| Ex-51 | 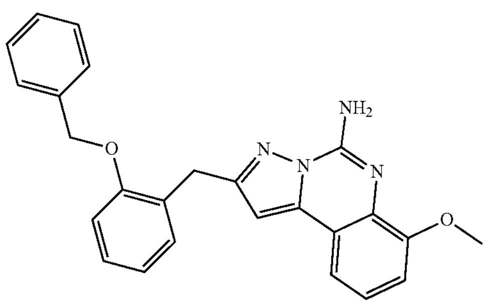 [SMILES: COc1cccc2c1nc(N)n1nc(Cc3ccccc3OCc3ccccc3)cc21] | 2-(2-(benzyloxy)benzyl)-7-methoxypyrazolo[1,5-c]quinazolin-5-amine | 411 [M + 1] |
| Ex-52 | 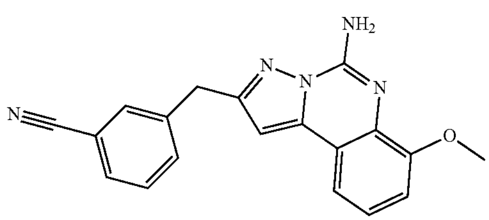 [SMILES: COc1cccc2c1nc(N)n1nc(Cc3cccc(C#N)c3)cc21] | 3-((5-amino-7-methoxypyrazolo[1,5-c]quinazolin-2-yl)methyl)benzonitrile | 330 [M + 1] |
| Ex-53 | 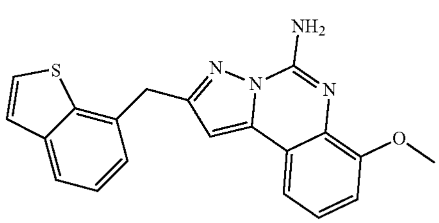 [SMILES: COc1cccc2c1nc(N)n1nc(Cc3cccc4ccsc34)cc21] | 2-(benzo[b]thiophen-7-ylmethyl)-7-methoxypyrazolo[1,5-c]quinazolin-5-amine | 361 [M + 1] |

TABLE II-continued

| Expl. No. | Structure | Name | LC-MS |
|---|---|---|---|
| Ex-54 | 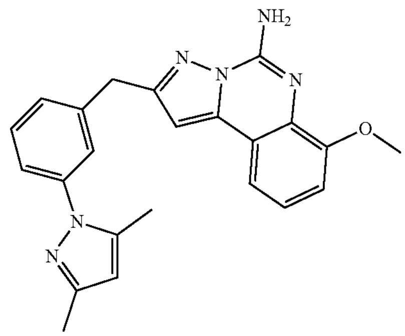 [SMILES: COc1cccc2c1nc(N)n1nc(Cc3cccc(-n4nc(C)cc4C)c3)cc21] | 2-(3-(3,5-dimethyl-1H-pyrazol-1-yl)benzyl)-7-methoxypyrazolo[1,5-c]quinazolin-5-amine | 399 [M + 1] |
| Ex-55 | 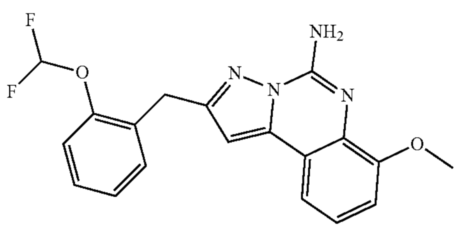 [SMILES: COc1cccc2c1nc(N)n1nc(Cc3ccccc3OC(F)F)cc21] | 2-(2-(difluoromethoxy)benzyl)-7-methoxypyrazolo[1,5-c]quinazolin-5-amine | 371 [M + 1] |
| Ex-56 | 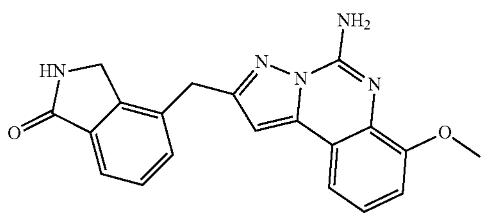 [SMILES: COc1cccc2c1nc(N)n1nc(Cc3cccc4c3CNC4=O)cc21] | 4-((5-amino-7-methoxypyrazolo[1,5-c]quinazolin-2-yl)methyl)isoindolin-1-one | 360 [M + 1] |
| Ex-57 | 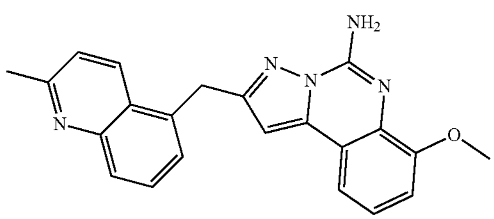 | 7-methoxy-2-((2-methylquinolin-5-yl)methyl)pyrazolo[1,5-c]quinazolin-5-amine | 370 [M + 1] |
| Ex-58 | 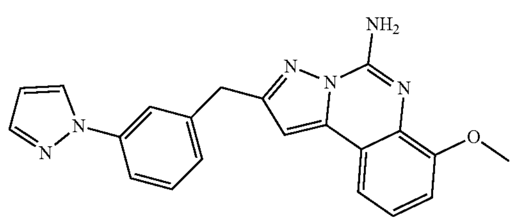 [SMILES: COc1cccc2c1nc(N)n1nc(Cc3cccc(-n4cccn4)c3)cc21] | 2-(3-(1H-pyrazol-1-yl)benzyl)-7-methoxypyrazolo[1,5-c]quinazolin-5-amine | 371 [M + 1] |
| Ex-59 | 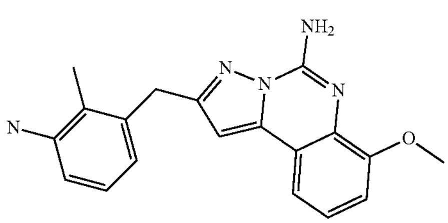 | 2-(3-fluoro-2-methylbenzyl)-7-methoxypyrazolo[1,5-c]quinazolin-5-amine | 337 [M + 1] |

TABLE II-continued

| Expl. No. | Structure | Name | LC-MS |
|---|---|---|---|
| Ex-60 | 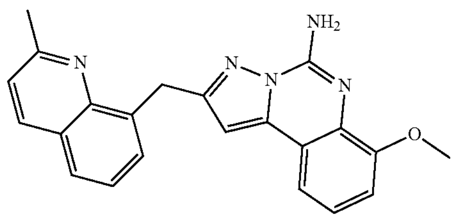 [SMILES: COc1cccc2c1nc(N)n1nc(Cc3cccc4ccc(C)nc34)cc21] | 7-methoxy-2-((2-methylquinolin-8-yl)methyl)pyrazolo[1,5-c]quinazolin-5-amine | 370 [M + 1] |
| Ex-61 | 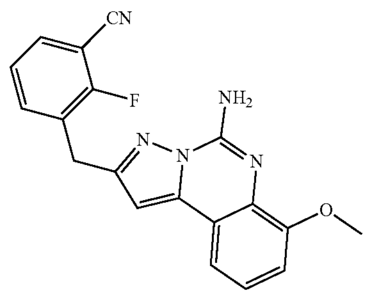 [SMILES: COc1cccc2c1nc(N)n1nc(Cc3cccc(C#N)c3F)cc21] | 3-((5-amino-7-methoxypyrazolo[1,5-c]quinazolin-2-yl)methyl)-2-fluorobenzonitrile | 348 [M + 1] |
| Ex-62 | 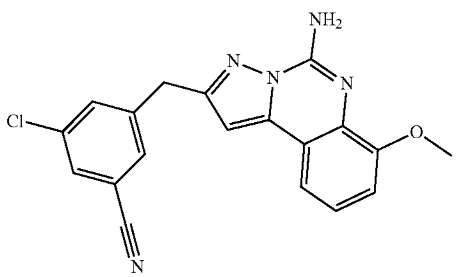 [SMILES: COc1cccc2c1nc(N)n1nc(Cc3cc(Cl)cc(C#N)c3)cc21] | 3-((5-amino-7-methoxypyrazolo[1,5-c]quinazolin-2-yl)methyl)-5-chlorobenzonitrile | 364 [M + 1] |
| Ex-63 | 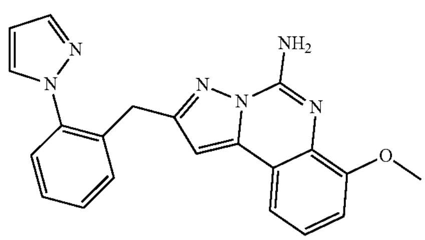 [SMILES: COc1cccc2c1nc(N)n1nc(Cc3ccccc3-n3cccn3)cc21] | 2-(2-(1H-pyrazol-1-yl)benzyl)-7-methoxypyrazolo[1,5-c]quinazolin-5-amine | 371 [M + 1] |
| Ex-64 | 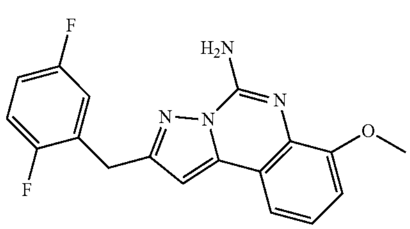 [SMILES: COc1cccc2c1nc(N)n1nc(Cc3cc(F)ccc3F)cc21] | 2-(2,5-difluorobenzyl)-7-methoxypyrazolo[1,5-c]quinazolin-5-amine | 341 [M + 1] |
| Ex-65 | 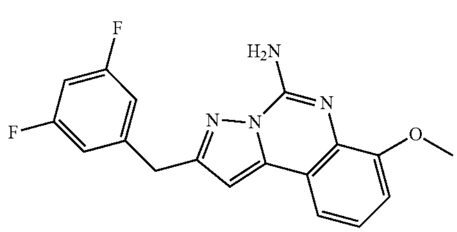 [SMILES: COc1cccc2c1nc(N)n1nc(Cc3cc(F)cc(F)c3)cc21] | 2-(3,5-difluorobenzyl)-7-methoxypyrazolo[1,5-c]quinazolin-5-amine | 341 [M + 1] |

Example 3: Preparation of 7-methoxy-2-((4-phenylpiperazin-1-yl)methyl)pyrazolo [1,5-c]quinazolin-5-amine (Ex-66)

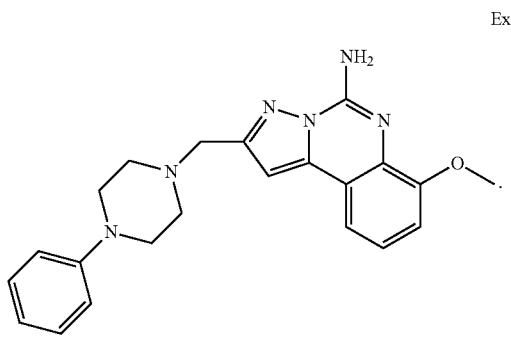

To a solution of 2-(chloromethyl)-7-methoxypyrazolo[1,5-c]quinazolin-5-amine (25 mg, 0.1 mmol) in DMF (2 ml) was added phenylpiperazine (19 mg, 0.11 mmol). The reaction mixture was stirred at 80° C. for 2 h. The resulting mixture was purified by reverse phase HPLC yielding Ex-66 as the TFA salt, the identity of which was confirmed by LC/MS=389 [M+1]. The activity was determined by the protocol described herein to be: A2a Ki=145 nM.

The compounds presented in Table III were prepared by using methods described in Example 3 and an appropriate cycloamine precursor.

Example 4: Preparation of (5-amino-7-methoxy-pyrazolo[1,5-c]quinazolin-2-yl)(4-(pyridin-2-yl)piperazin-1-yl)methanone (Ex-70)

Scheme 3

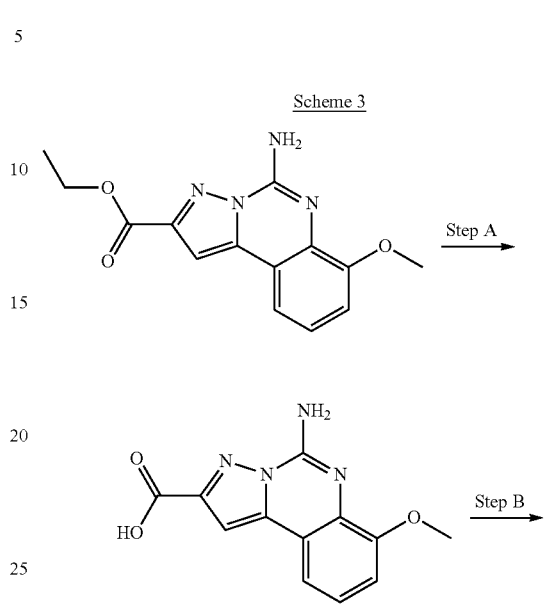

TABLE III

| Exp. No. | Structure | Name | LC-MS |
|---|---|---|---|
| Ex-67 | 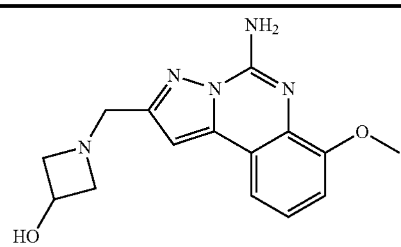 | 1-((5-amino-7-methoxypyrazolo[1,5-c]quinazolin-2-yl)methyl)azetidin-3-ol | 300 [M + 1]. |
| Ex-68 | 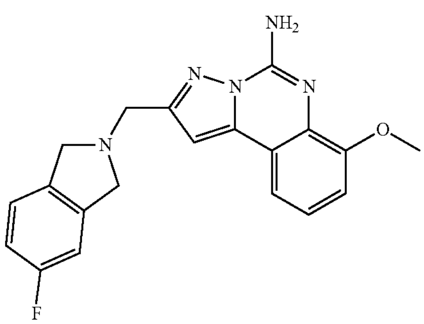 [SMILES: COc1cccc2c1nc(N)n1nc(CN3Cc4ccc(F)cc4C3)cc21] | 2-((5-fluoroisoindolin-2-yl)methyl)-7-methoxypyrazolo[1,5-c]quinazolin-5-amine | 364 [M + 1] |
| Ex-69 | 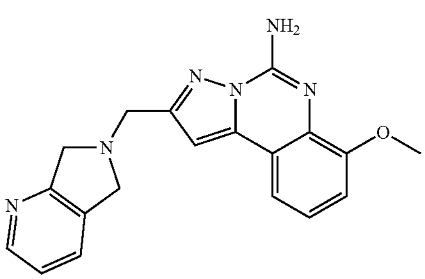 [SMILES: COc1cccc2c1nc(N)n1nc(CN3Cc4cccnc4C3)cc21] | 2-((5,7-dihydro-6H-pyrrolo[3,4-b]pyridin-6-yl)methyl)-7-methoxypyrazolo[1,5-c]quinazolin-5-amine | 347 [M + 1] |

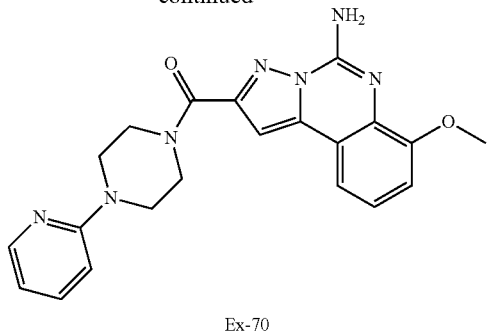

Ex-70

Step A: 5-amino-7-methoxypyrazolo[1,5-c]quinazoline-2-carboxylic acid

To a solution of ethyl-5-amino-7-methoxypyrazolo[1,5-c]quinazoline-2-carboxylate (3.0 g, 11.7 mmol) in EtOH (20 ml) and H$_2$O (20 ml) was added 10N sodium hydroxide (3.51 ml, 35.1 mmol). The reaction mixture was stirred at 65° C. for 1 hr., then cooled to room temperature and acidified with 2N HCl to a pH 3~4. The precipitate thus yielded was filtered and dried in vacuo overnight, and the residue used in the next step without any further purification.

Step B: (5-amino-7-methoxypyrazolo[1,5-c]quinazolin-2-yl)(4-(pyridin-2-yl)piperazin-1-yl)methanone (Ex-70)

To a solution of 5-amino-7-methoxypyrazolo[1,5-c]quinazoline-2-carboxylic acid prepared in the previous step (100 mg, 0.4 mmol) was added 1-(2-pyridyl)piperazine (76 mg, 0.5 mmol), HATU (177 mg, 0.5 mmol), and DIPEA (0.10 ml, 0.6 mmol). The reaction mixture was stirred at 70° C. for 1 hour, then diluted with H$_2$O and the resulting precipitate was filtered and washed with H$_2$O. The filtered solid was dried in vacuo to yield the desired product without any further purification necessary. LC/MS=404 [M+1]. The activity was determined by the protocol described herein to be: A2a Ki=7 nm.

The compounds presented in Table IV were prepared by using the methods described in the preparation of Example 4 with an appropriate precursor.

TABLE IV

| Exp No. | Structure | Name | LC-MS |
|---|---|---|---|
| Ex-71 | 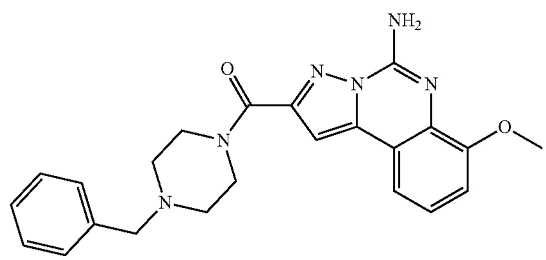 [SMILES: COc1cccc2c1nc(N)n1nc(C(=O)N3CCN(Cc4ccccc4)CC3)cc21] | (5-amino-7-methoxypyrazolo[1,5-c]quinazolin-2-yl)(4-benzylpiperazin-1-yl)methanone | 417 [M + 1]. |
| Ex-72 | 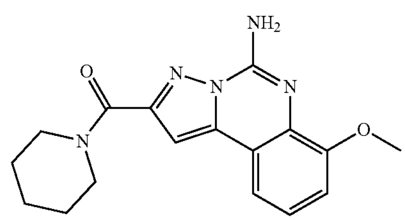 [SMILES: COc1cccc2c1nc(N)n1nc(C(=O)N3CCCCC3)cc21] | (5-amino-7-methoxypyrazolo[1,5-c]quinazolin-2-yl)(piperidin-1-yl)methanone | 326 [M + 1]. |
| Ex-73 | 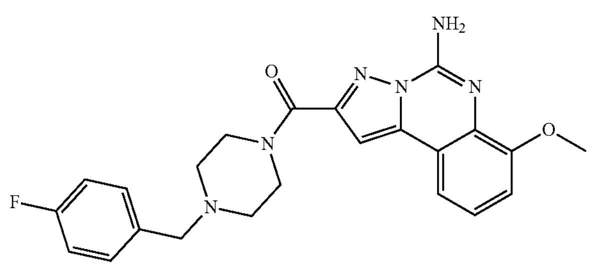 [SMILES: COc1cccc2c1nc(N)n1nc(C(=O)N3CCN(Cc4ccc(F)cc4)CC3)cc21] | (5-amino-7-methoxypyrazolo[1,5c]-quinazolin-2-yl)(4-(4-fluorobenzyl)-piperazin-1-yl)methanone | 435 [M + 1]. |
| Ex-74 | 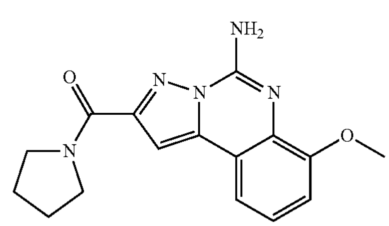 [SMILES: COc1cccc2c1nc(N)n1nc(C(=O)N3CCCC3)cc21] | (5-amino-7-methoxypyrazolo[1,5-c]quinazolin-2-yl)(pyrrolidin-1-yl)methanone | 312 [M + 1]. |

TABLE IV-continued

| Exp No. | Structure | Name | LC-MS |
|---|---|---|---|
| Ex-75 | 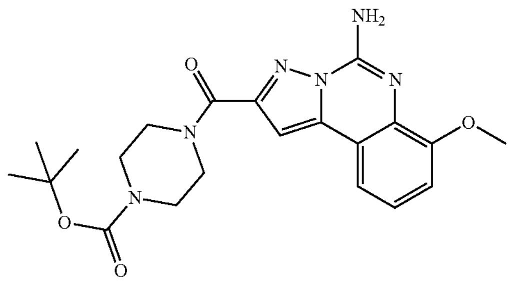 [SMILES: COc1cccc2c1nc(N)n1nc(C(=O)N3CCN(C(=O)OC(C)(C)C)CC3)cc21] | tert-butyl 4-(5-amino-7-methoxypyrazolo[1,5-c]quinazoline-2-carbonyl)piperazine-1-carboxylate | 427 [M + 1]. |
| Ex-76 | 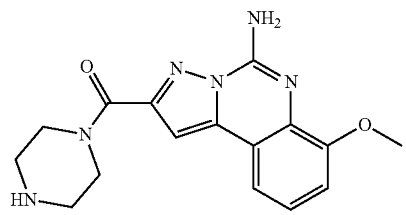 [SMILES: COc1cccc2c1nc(N)n1nc(C(=O)N3CCNCC3)cc21] | (5-amino-7-methoxypyrazolo[1,5-c]quinazolin-2-yl)(piperazin-1-yl)methanone | 327 [M + 1]. |
| Ex-77 | 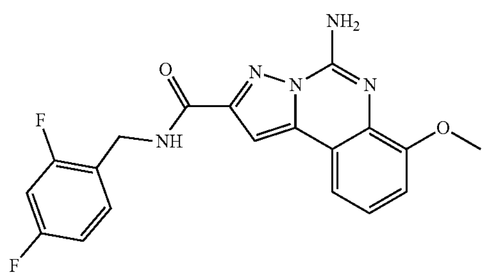 [SMILES: COc1cccc2c1nc(N)n1nc(C(=O)NCc3ccc(F)cc3F)cc21] | 5-amino-N-(2,4-difluorobenzyl)-7-methoxypyrazolo[1,5-c]quinazoline-2-carboxamide | 384 [M + 1]. |
| Ex-78 | 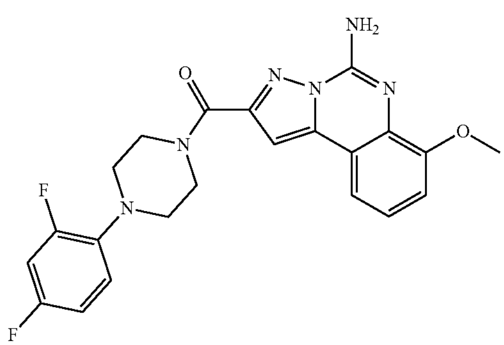 [SMILES: COc1cccc2c1nc(N)n1nc(C(=O)N3CCN(c4ccc(F)cc4F)CC3)cc21] | (5-amino-7-methoxypyrazolo[1,5-c]quinazolin-2-yl)(4-(2,4-difluorophenyl)piperazin-1-yl)methanone | 439 [M + 1]. |
| Ex-79 | 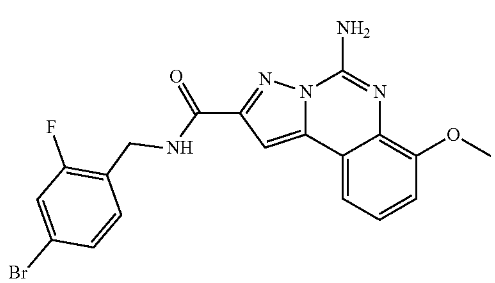 [SMILES: COc1cccc2c1nc(N)n1nc(C(=O)NCc3ccc(Br)cc3F)cc21] | 5-amino-N-(4-bromo-2-fluorobenzyl)-7-methoxypyrazolo[1,5-c]quinazoline-2-carboxamide | 445 [M + 1]. |

TABLE IV-continued

| Exp No. | Structure | Name | LC-MS |
|---|---|---|---|
| Ex-80 | 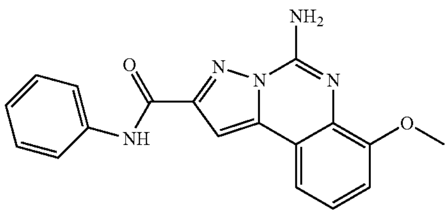 [SMILES: COc1cccc2c1nc(N)n1nc(C(=O)Nc3ccccc3)cc21] | 5-amino-7-methoxy-N-phenylpyrazolo[1,5-c]quinazoline-2-carboxamide | 334 [M + 1]. |
| Ex-81 | 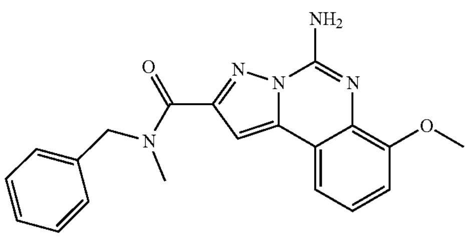 [SMILES: COc1cccc2c1nc(N)n1nc(C(=O)N(C)Cc3ccccc3)cc21] | 5-amino-N-benzyl-7-methoxy-N-methylpyrazolo[1,5-c]quinazoline-2-carboxamide | 362 [M + 1]. |
| Ex-82 | 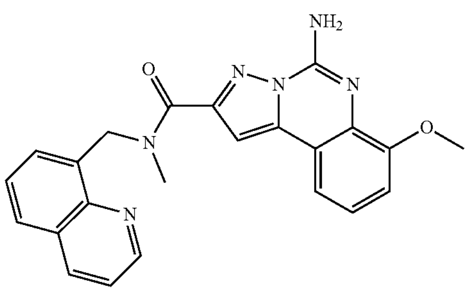 [SMILES: COc1cccc2c1nc(N)n1nc(C(=O)N(C)Cc3cccc4cccnc34)cc21] | 5-amino-7-methoxy-N-methyl-N-(quinolin-8-ylmethyl)pyrazolo[1,5-c]quinazoline-2-carboxamide | 413 [M + 1]. |
| Ex-83 | 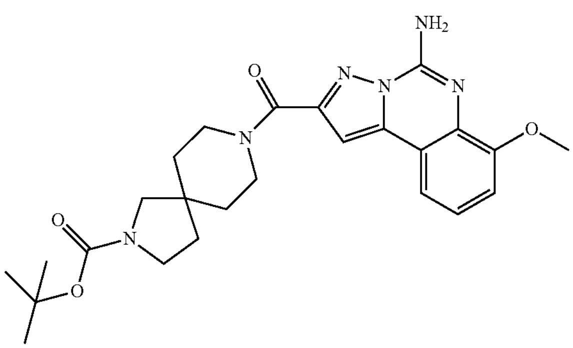 [SMILES: COc1cccc2c1nc(N)n1nc(C(=O)N3CCC4(CCN(C(=O)OC(C)(C)C)C4)CC3)cc21] | tert-butyl 8-(5-amino-7-methoxy-pyrazolo[1,5-c]quinazoline-2-carbonyl)-2,8-diazaspiro[4.5]decane-2-carboxylate | 481 [M + 1]. |
| Ex-84 | 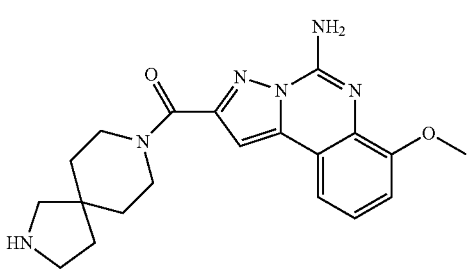 [SMILES: COc1cccc2c1nc(N)n1nc(C(=O)N3CCC4(CCNC4)CC3)cc21] | (5-amino-7-methoxypyrazolo[1,5-c]quinazolin-2-yl)(2,8-diazaspiro[4.5]decan-8-yl)methanone | 381 [M + 1]. |

TABLE IV-continued

| Exp No. | Structure | Name | LC-MS |
|---|---|---|---|
| Ex-85 | 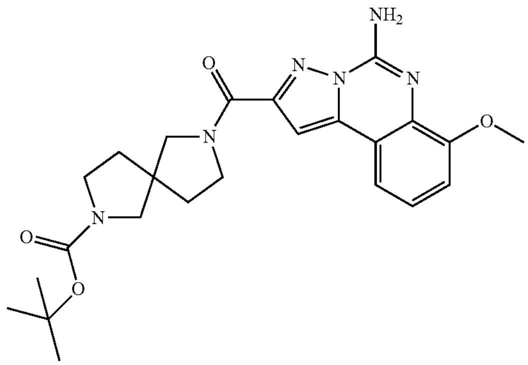 [SMILES: COc1cccc2c1nc(N)n1nc(C(=O)N3CCC4(CCN(C(=O)OC(C)(C)C)C4)C3)cc21] | tert-butyl 7-(5-amino-7-methoxypyrazolo[1,5-c]quinazoline-2-carbonyl)-2,7-diazaspiro[4.4]nonane-2-carboxylate | 467 [M + 1]. |
| Ex-86 | 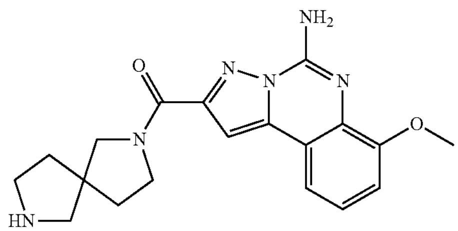 [SMILES: COc1cccc2c1nc(N)n1nc(C(=O)N3CCC4(CCNC4)C3)cc21] | (5-amino-7-methoxypyrazolo[1,5-c]quinazolin-2-yl)(2,7-diazaspiro[4.4]nonan-2-yl)methanone | 367 [M + 1]. |
| Ex-87 | 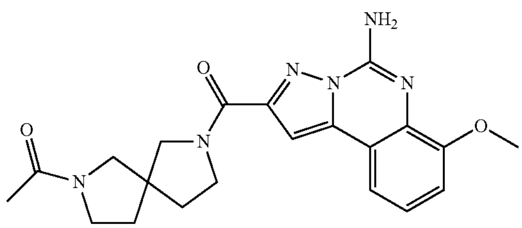 [SMILES: COc1cccc2c1nc(N)n1nc(C(=O)N3CCC4(CCN(C(C)=O)C4)C3)cc21] | 1-(7-(5-amino-7-methoxypyrazolo[1,5-c]quinazoline-2-carbonyl)-2,7-diazaspiro[4.4]nonan-2-yl)ethan-1-one | 409 [M + 1]. |
| Ex-88 | 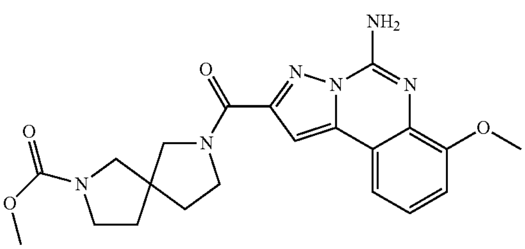 [SMILES: COC(=O)N1CCC2(CCN(C(=O)c3cc4c5cccc(OC)c5nc(N)n4n3)C2)C1] | methyl 7-(5-amino-7-methoxypyrazolo[1,5-c]quinazoline-2-carbonyl)-2,7-diazaspiro[4.4]nonane-2-carboxylate | 425 [M + 1]. |
| Ex-89 | 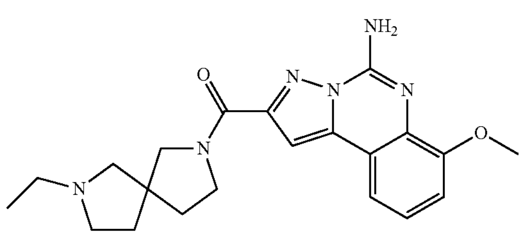 [SMILES: CCN1CCC2(CCN(C(=O)c3cc4c5cccc(OC)c5nc(N)n4n3)C2)C1] | (5-amino-7-methoxypyrazolo[1,5-c]quinazolin-2-yl)(7-ethyl-2,7-diazaspiro[4.4]nonan-2-yl)methanone | 395 [M + 1]. |
| Ex-90 | 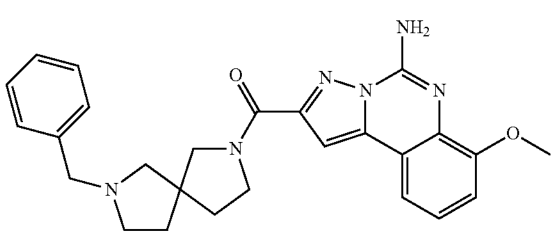 [SMILES: COc1cccc2c1nc(N)n1nc(C(=O)N3CCC4(CCN(Cc5ccccc5)C4)C3)cc21] | (5-amino-7-methoxypyrazolo[1,5-c]quinazolin-2-yl)(7-benzyl-2,7-diazaspiro[4.4]nonan-2-yl)methanone | 457 [M + 1]. |

TABLE IV-continued

| Exp No. | Structure | Name | LC-MS |
|---|---|---|---|
| Ex-91 | 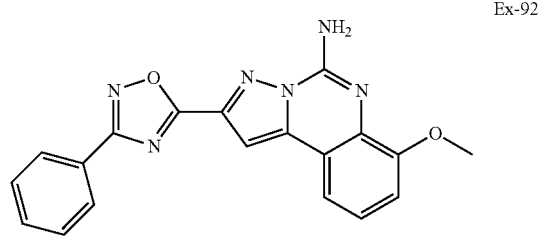 | 5-amino-7-methoxy-N-(quinolin-8-ylmethyl)pyrazolo[1,5-c]quinazoline-2-carboxamide | 399 [M + 1]. |

Example 5: Preparation of 7-methoxy-2-(3-phenyl-1,2,4-oxadiazol-5-yl)pyrazolo[1,5-c]quinazolin-5-amine (Ex-92), 2-(3-benzyl-1,2,4-oxadiazol-5-yl)-7-methoxypyrazolo[1,5-c]quinazolin-5-amine (Ex-93), and 7-methoxy-2-(quinolin-8-ylmethyl)pyrazolo[1,5-c]quinazolin-5-amine (Ex-94)

Ex-92

Preparation of: 7-methoxy-2-(3-phenyl-1,2,4-oxadiazol-5-yl)pyrazolo[1,5-c]quinazolin-5-amine (Ex-92)

To a solution of 5-amino-7-methoxypyrazolo[1,5-c]quinazoline-2-carboxylic acid (100 mg, 0.4 mmol) in DMF (3 ml) was added HOBt (52 mg, 0.4 mmol) and EDCI (52 mg, 0.4 mmol). The reaction mixture was stirred at room temperature for 15 min then the benzenecarboximidamide (53 mg, 0.4 mmol) was added to the reaction mixture and stirred at 120° C. for 12 h. The resulting mixture was diluted with EtOAc and then washed with $H_2O$ three times. The separated organic layer was dried over $MgSO_4$, filtered, and concentrated in vacuo. The resulting residue was purified by reverse phase HPLC to yield the desired product as the TFA salt (1 mg, 1%). LC/MS=359 [M+1]. The activity was determined by the protocol described herein to be: A2a Ki=101 nM.

Preparation of: 2-(3-benzyl-1,2,4-oxadiazol-5-yl)-7-methoxypyrazolo[1,5-c]quinazolin-5-amine (Ex-93)

Ex-93

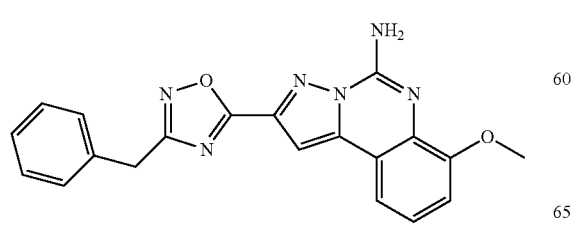

The compound Ex-93 was prepared by using method described for preparation of Ex-92, above. LC/MS=373 [M+1]. The activity was determined by the protocol described herein to be: A2a Ki=45 nM.

Preparation of: 2-(quinolin-8-ylmethyl)pyrazolo[1,5-c]quinazolin-5-amine (Ex-94)

Scheme 4

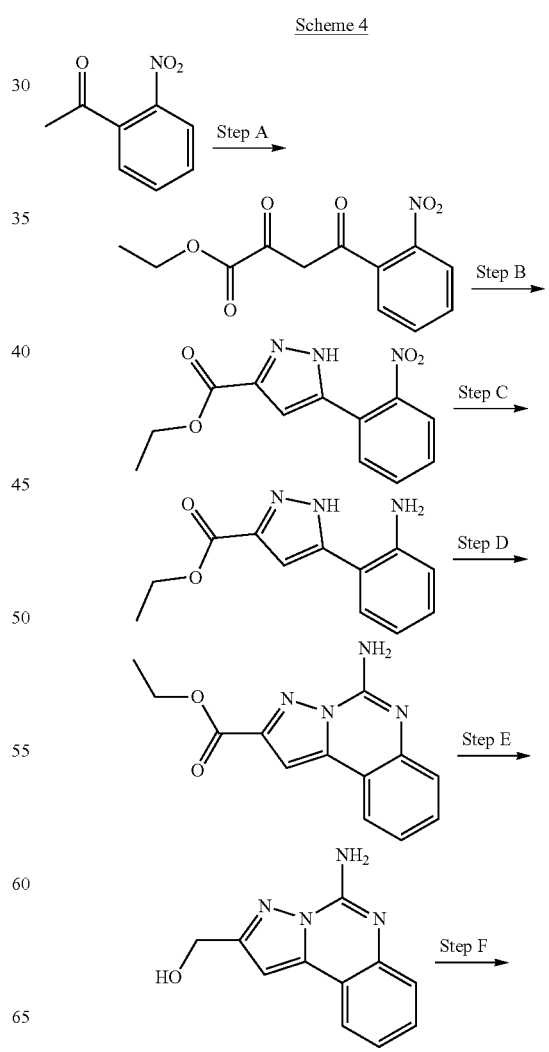

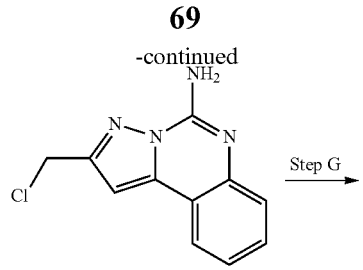

Step G →

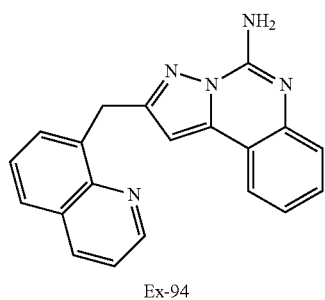

Ex-94

Step A: ethyl 4-(2-nitrophenyl)-2,4-dioxobutanoate

To 100 mL of a 1M solution of LiHMDS in THF (66.6 ml, 66.6 mmol) was added a solution of 1-(2-nitrophenyl)ethanone (10.0 g, 60.6 mmol) in THF (50 ml). The reaction mixture was stirred at −78° C. for 15 min and then diethyl oxalate (9.85 ml, 72.7 mmol) was added slowly to the mixture. The resulting mixture was warmed up to room temperature and stirred for 1 hour then acidified with 1N HCl. The resulting mixture was diluted with EtOAc, and the organic layer was separated, dried over MgSO$_4$, filtered, and concentrated in vacuo. The resulting residue was carried to Step B without any purification.

Step B: ethyl 5-(2-nitrophenyl)-1H-pyrazole-3-carboxylate

To a solution of the crude ethyl 4-(2-nitrophenyl)-2,4-dioxobutanoate (17.8 g, 67.1 mmol) in AcOH (150 ml) was added slowly the hydrazine hydrate (3.7 g, 73.8 mmol). The reaction mixture was stirred at 80° C. for 2 h. The mixture was cooled to room temperature and concentrated in vacuo. The resulting residue was employed in the next step without further purification.

Step C: ethyl 5-(2-aminophenyl)-1H-pyrazole-3-carboxylate

To a solution of crude ethyl 5-(2-nitrophenyl)-1H-pyrazole-3-carboxylate prepared in the previous step (9.3 g, 35.6 mmol) in MeOH (100 ml) was added a catalytic amount of Pd/C. The reaction mixture was degassed and then stirred under H$_2$ atmosphere for 12 hours, following which it was diluted with CH$_2$Cl$_2$ and filtered through a pad of celite. The filtrate was concentrated in vacuo and the residue thus obtained was purified by column chromatography on silica gel (ISCO 120 g), eluting with 20:1 CH$_2$Cl$_2$/MeOH to give the desired product.

Step D: ethyl 5-aminopyrazolo[1,5-c]quinazoline-2-carboxylate

To a solution of ethyl 5-(2-aminophenyl)-1H-pyrazole-3-carboxylate (5.5 g, 23.8 mmol) in EtOH (60 ml) was added 3M sol. of BrCN in DCM (5.3 ml, 71.4 mmol). The reaction mixture was stirred at room temperature over 2 days. The resulting precipitate was filtered and dried in vacuo to yield the desired product without any purification necessary (4.8 g, 18.4 mmol).

Step E: (5-aminopyrazolo[1,5-c]quinazolin-2-yl)methanol

To a solution of ethyl 5-aminopyrazolo[1,5-c]quinazoline-2-carboxylate (4.8 g, 18.5 mmol) in THF (50 ml) was added 2M sol. of LiBH$_4$ in THF (18.5 ml, 37.1 mmol). The reaction mixture was stirred at room temperature for three days, then quenched slowly with H$_2$O. The resulting mixture was acidified with 1N HCl and concentrated in vacuo to remove most of the THF. The resulting aqueous mixture was basified with 1N NaOH, and the resulting precipitate was filtered and dried in vacuo to yield the desired product with any purification necessary.

Step F: 2-(chloromethyl)pyrazolo[1,5-c]quinazolin-5-amine

To a solution of (5-aminopyrazolo[1,5-c]quinazolin-2-yl)methanol (2.2 g, 10.3 mmol) in CH$_2$Cl$_2$ (10 ml) was added thionyl chloride (10.0 ml, 0.13 mol). Reaction mixture was stirred at room temperature for 1 hour then concentrated in vacuo with a boiling water bath. The solid thus obtained was used in the subsequent step without any further purification.

Step G: 2-(quinolin-8-ylmethyl)pyrazolo[1,5-c]quinazolin-5-amine

To a solution of 2-(chloromethyl)pyrazolo[1,5-c]quinazolin-5-amine (100 mg, 0.4 mmol) in 1,4 dioxane (6.0 ml) and H$_2$O (2.0 ml) was added quinoline-8-boronic acid (149.0 mg, 0.9 mmol), dppf (70.2 mg, 0.09 mmol), and K$_2$CO$_3$ (178.0 mg, 1.3 mmol). The resulting mixture was stirred in a sealed tube at 80° C. for 12 hours then cooled to room temperature and diluted with CH$_2$Cl$_2$. This mixture was washed with NaHCO$_3$ (sat.), the organic layer was separated, dried over MgSO$_4$, filtered, and concentrated in vacuo. The resulting residue was purified by reverse phase HPLC to yield the product as the TFA salt (4.0 mg, 2%). LC/MS=326 [M+1]. The activity was determined by the protocol described herein to be: A2a Ki=10 nM.

The compounds presented in Table V were prepared using the method described above for the preparation of compound Ex-94.

TABLE V
| Exp. No. | Structure | Name | LC-MS |
|---|---|---|---|
| EX-95 | 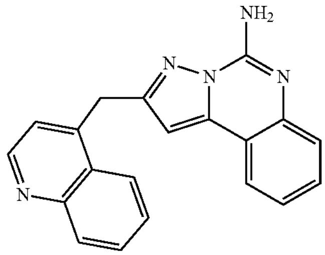 [SMILES: Nc1nc2ccccc2c2cc(Cc3ccnc4ccccc34)nn12] | 2-(quinolin-4-ylmethyl)pyrazolo[1,5-c]quinazolin-5-amine | 326 [M + 1]. |
| Ex-96 | 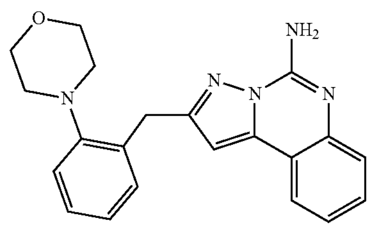 [SMILES: Nc1nc2ccccc2c2cc(Cc3ccccc3N3CCOCC3)nn12] | 2-(2-morpholinobenzyl)pyrazolo[1,5c]quinazolin-5-amine | 360 [M + 1]. |
| Ex-97 | 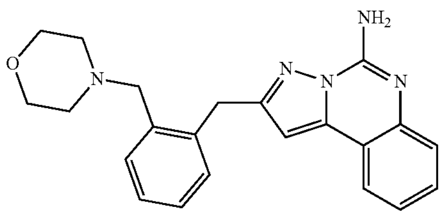 [SMILES: Nc1nc2ccccc2c2cc(Cc3ccccc3CN3CCOCC3)nn12] | 2-(2-(morpholinomethyl)-benzyl)pyrazolo[1,5-c]-quinazolin-5-amine | 374 [M + 1]. |
Example 6: Preparation of 2-(5-(quinolin-8-yl)-1,3,4-oxadiazol-2-yl)pyrazolo[1,5-c]quinazolin-5-amine (Ex-98)
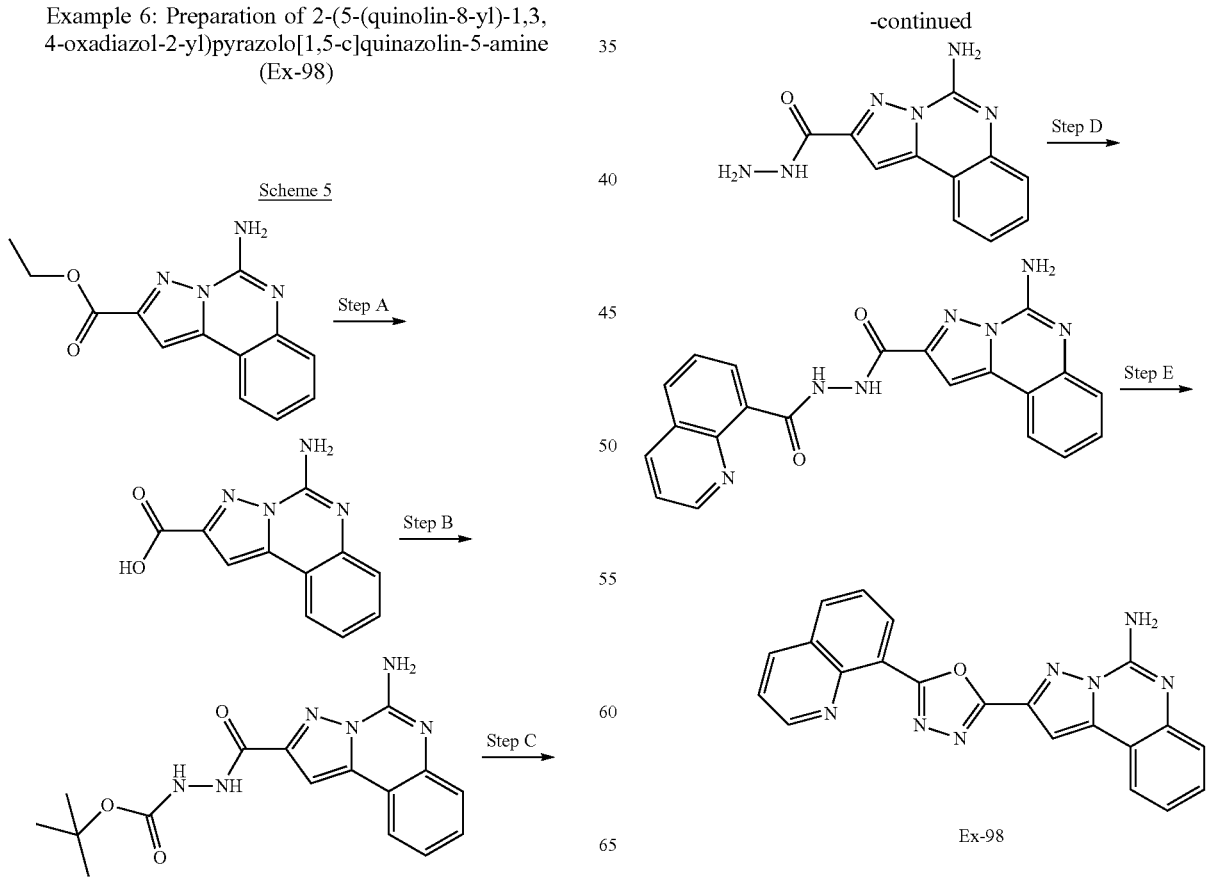

Step A: 5-aminopyrazolo[1,5-c]quinazoline-2-carboxylic acid

To a solution of the ethyl 5-aminopyrazolo[1,5-c]quinazoline-2-carboxylate (3.0 g, 11.7 mmol) in EtOH (20 ml) and water (20 ml) was added 10N sodium hydroxide (3.51 ml, 35.1 mmol). The reaction mixture was stirred at 65° C. for 1 hour, then cooled to room temperature and acidified with 2N HCl until pH 3~4. The precipitate thus obtained was filtered and dried in vacuo overnight and the residue thus obtained was employed in the next step without any further purification.

Step B: tert-butyl 2-(5-aminopyrazolo[1,5-c]quinazoline-2-carbonyl)hydrazinecarboxylate To a solution of the 5-aminopyrazolo[1,5-c]quinazoline-2-carboxylic acid prepared in the previous step (1.1 g, 4.8 mmol) in DMF (15 ml) was added tert-butyl carbazate (0.70 g, 5.30 mmol), HATU (2.75 g, 7.2 mmol), and DIPEA (2.52 ml, 14.5 mmol). The reaction mixture was stirred at room temperature for 2 hours, diluted with water and the resulting precipitate was filtered, washed with water followed by a 1:1 V/V mixture of $CH_2Cl_2$: Hexanes. The resulting crude product was carried onto the deprotection step without any further purification.

Step C: 5-aminopyrazolo[1,5-c]quinazoline-2-carbohydrazide

A suspension of the crude tert-butyl 2-(5-aminopyrazolo[1,5-c]quinazoline-2-carbonyl)hydrazinecarboxylate prepared in the last step (1.6 g, 4.7 mmol) in 4M dioxane/hydrochloric acid (10 ml, 40.0 mmol), was stirred at room temperature for 2 hours, then concentrated in vacuo to yield the desired product as an HCl salt which was used in the subsequent step without any further purification.

Step D: 5-amino-N'-(quinoline-8-carbonyl)pyrazolo[1,5-c]quinazoline-2-carbohydrazide Into a solution of the 5-aminopyrazolo[1,5-c]quinazoline-2-carbohydrazide prepared in the previous step (300 mg, 1.08 mmol) in DMF (9 ml), was added quinoline-8-carboxylic acid (205 mg, 1.18 mmol), HATU (389 mg, 1.62 mmol), and DIPEA (0.937 ml, 5.38 mmol). Reaction mixture was stirred at room temperature for 2 hours, diluted with water and the resulting precipitate was isolated by filtration and washed with water then 1:1, V/V, $CH_2Cl_2$: Hexanes and dried in vacuo. The product thus provided was used in the subsequent step without further purification.

Step E: 2-(5-(quinolin-8-yl)-1,3,4-oxadiazol-2-yl)pyrazolo[1,5-c]quinazolin-5-amine (Ex-98)

Into a solution of the 5-amino-N'-(quinoline-8-carbonyl)pyrazolo[1,5-c]quinazoline-2-carbohydrazide prepared in the previous step (150 mg, 0.38 mmol) in acetonitrile (5 ml) was added triphenylphosphine (178 mg, 0.68 mmol) and DIPEA (0.34 ml, 1.89 mmol). This reaction mixture was stirred at room temperature for 5 min then hexachloroethane (0.15 ml, 0.49 mmol) was added to the reaction mixture. The resulting mixture was stirred at room temperature for 1.5 hours. Water was then added to the reaction mixture and it was diluted with $CH_2Cl_2$. The organic layer was extracted with $CH_2Cl_2$, dried over $MgSO_4$, and filtered, then concentrated in vacuo. The resulting residue was purified by Prep TLC 10:1 $CH_2Cl_2$:MeOH to yield the compound Ex-98.

Example 7: Preparation of 7-methoxy-2-(5-(quinolin-7-ylmethyl)-1,3,4-oxadiazol-2-yl)pyrazolo[1,5-c]quinazolin-5-amine (Ex-99) and related compounds of Table VI

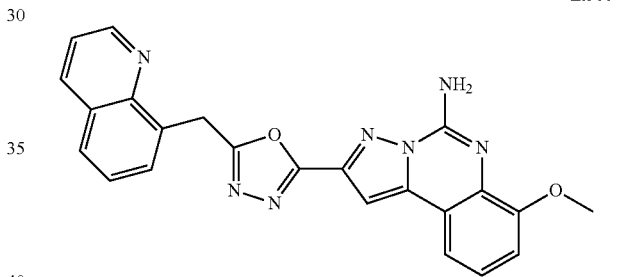

Ex-99

The compounds presented in Table VI (below) were prepared using the methodology presented in Example 6 and an appropriate carboxylic acid precursor.

TABLE VI

| Exp. No. | Structure | Name | LC-MS |
| --- | --- | --- | --- |
| Ex-99 | 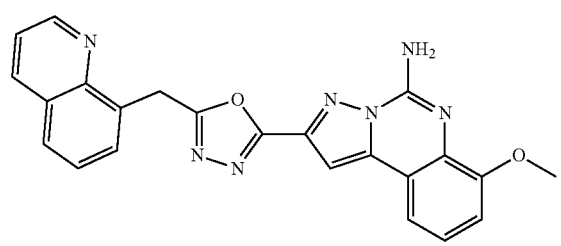 [SMILES: COc1cccc2c1nc(N)n1nc(-c3nnc(Cc4cccc5cccnc45)o3)cc21] | 7-methoxy-2-(5-(quinolin-7-ylmethyl)-1,3,4-oxadiazol-2-yl)pyrazolo[1,5-c]quinazolin-5-amine | 424 [M + 1] |

TABLE VI-continued

| Exp. No. | Structure | Name | LC-MS |
| --- | --- | --- | --- |
| Ex-100 | 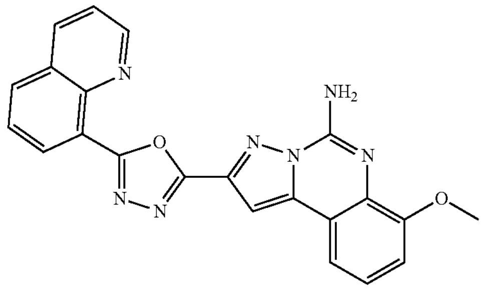 | 7-methoxy-2-(5-(quinolin-8-yl)-1,3,4-oxadiazol-2-yl)pyrazolo[1,5-c]quinazolin-5-amine | 424 [M + 1] |
| Ex-101 | 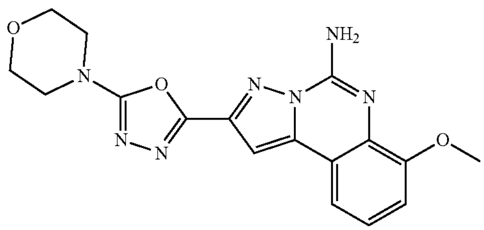 [SMILES: COc1cccc2c1nc(N)n1nc(-c3nnc(N4CCOCC4)o3)cc21] | 7-methoxy-2-(5-morpholino-1,3,4-oxadiazol-2-yl)pyrazolo[1,5-c]quinazolin-5-amine | 368 [M + 1]. |
| Ex-102 | 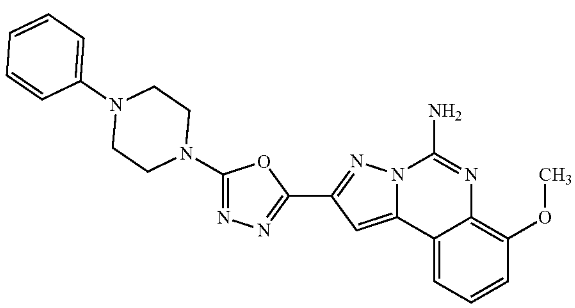 [SMILES: COc1cccc2c1nc(N)n1nc(-c3nnc(N4CCN(c5ccccc5)CC4)o3)cc21] | 7-methoxy-2-(5-(4-phenylpiperazin-1-yl)-1,3,4-oxadiazol-2-yl)pyrazolo[1,5-c]quinazolin-5-amine | 443 [M + 1]. |
| Ex-103 | 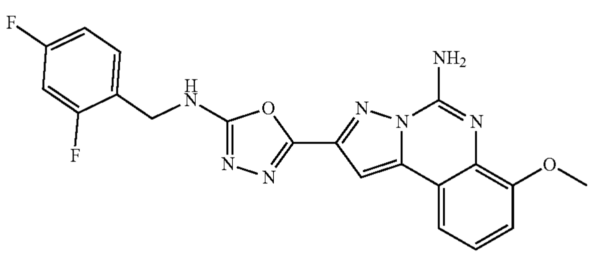 [SMILES: COc1cccc2c1nc(N)n1nc(-c3nnc(NCc4ccc(F)cc4F)o3)cc21] | 5-(5-amino-7-methoxypyrazolo[1,5-c]quinazolin-2-yl)-N-(2,4-difluorobenzyl)-1,3,4-oxadiazol-2-amine | 424 [M + 1]. |

Example 8: Preparation of fluorine-substituted pyrazolo[1,5-c]quinazolin-5-amine compounds (compounds Ex-104 to Ex-114)

The compounds presented in Table VII were prepared using the procedures detailed in Example 2 with an appropriate fluorine-substituted pyrazolo[1,5-c]quinazolin-5-amine precursor.

TABLE VII

| Ex No. | Structure | Name | LC-MS |
|---|---|---|---|
| Ex-104 | 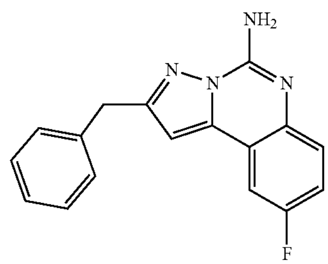 [SMILES: Nc1nc2ccc(F)cc2c2cc(Cc3ccccc3)nn12] | 2-benzyl-9-fluoropyrazolo[1,5-c]quinazolin-5-amine | 293 [M + 1] |
| Ex-105 | 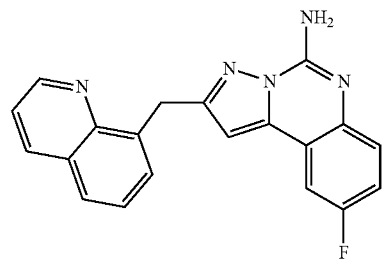 [SMILES: Nc1nc2ccc(F)cc2c2cc(Cc3cccc4cccnc34)nn12] | 9-fluoro-2-(quinolin-8-ylmethyl)pyrazolo[1,5-c]quinazolin-5-amine | 344 [M + 1]. |
| Ex-106 | 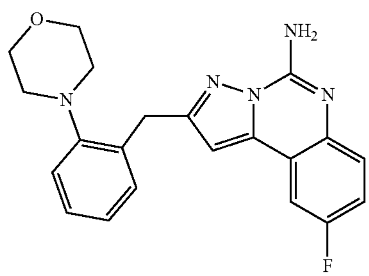 [SMILES: Nc1nc2ccc(F)cc2c2cc(Cc3ccccc3N3CCOCC3)nn12] | 9-fluoro-2-(2-morpholinobenzyl)pyrazolo[1,5-c]quinazolin-5-amine | 378 [M + 1]. |
| Ex-107 | 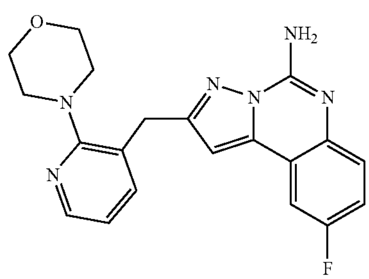 [SMILES: Nc1nc2ccc(F)cc2c2cc(Cc3cccnc3N3CCOCC3)nn12] | 9-fluoro-2-((2-morpholinopyridin-3-yl)methyl)pyrazolo[1,5-c]quinazolin-5-amine | 379 [M + 1]. |
| Ex-108 | 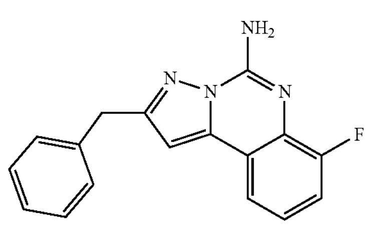 [SMILES: Nc1nc2c(F)cccc2c2cc(Cc3ccccc3)nn12] | 2-benzyl-7-fluoropyrazolo[1,5-c]quinazolin-5-amine | 293 [M + 1] |
| Ex-109 | 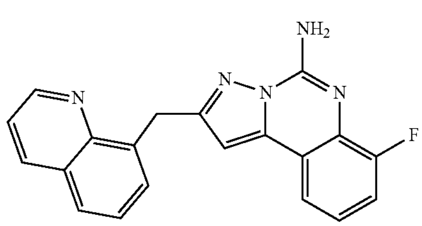 [SMILES: Nc1nc2c(F)cccc2c2cc(Cc3cccc4cccnc34)nn12] | 7-fluoro-2-(quinolin-8-ylmethyl)pyrazolo[1,5-c]quinazolin-5-amine | 344 [M + 1] |

TABLE VII-continued

| Ex No. | Structure | Name | LC-MS |
|---|---|---|---|
| Ex-110 | 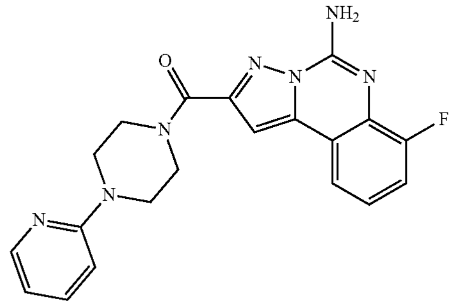 [SMILES: Nc1nc2c(F)cccc2c2cc(C(=O)N3CCN(c4ccccn4)CC3)nn12] | (5-amino-7-fluoropyrazolo[1,5-c]quinazolin-2-yl)(4-(pyridin-2-yl)piperazin-1-yl)methanone | 392 [M + 1] |
| Ex-111 | 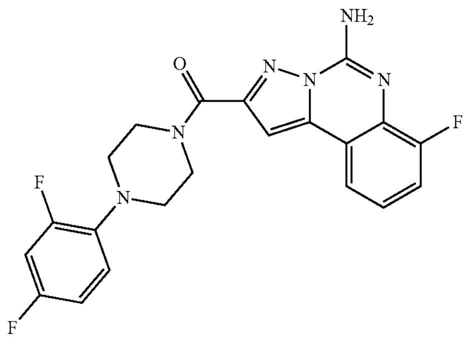 [SMILES: Nc1nc2c(F)cccc2c2cc(C(=O)N3CCN(c4ccc(F)cc4F)CC3)nn12] | (5-amino-7-fluoropyrazolo[1,5-c]quinazolin-2-yl)(4-(2,4-difluorophenyl)piperazin-1-yl)methanone | 427 [M + 1]. |
| Ex-112 | 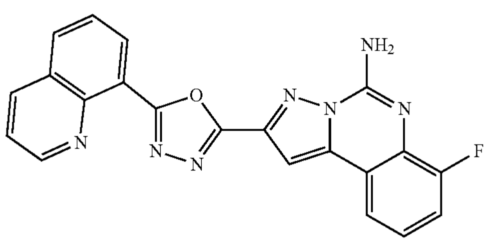 [SMILES: Nc1nc2c(F)cccc2c2cc(-c3nnc(-c4cccc5cccnc45)o3)nn12] | 7-fluoro-2-(5-(quinolin-8-yl)-1,3,4-oxadiazol-2-yl)pyrazolo[1,5-c]quinazolin-5-amine | 392 [M + 1] |
| Ex-113 | 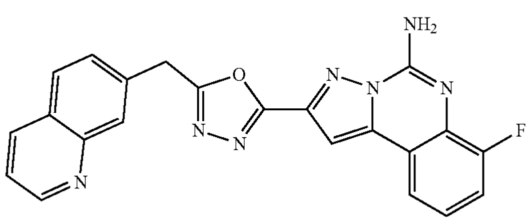 [SMILES: Nc1nc2c(F)cccc2c2cc(-c3nnc(Cc4ccc5cccnc5c4)o3)nn12] | 7-fluoro-2-(5-(quinolin-7-ylmethyl)-1,3,4-oxadiazol-2-yl)pyrazolo[1,5-c]quinazolin-5-amine | 412 [M + 1]. |

Example 9: Preparation of the compounds of Table VIII

The compounds presented in Table VIII (below) were prepared using the procedures detailed in Example 3 with an appropriate fluorine-substituted pyrazolo[1,5-c]quinazolin-5-amine precursor.

TABLE VIII

| Exp. No. | Structure | Name | LC-MS |
|---|---|---|---|
| Ex-114 | 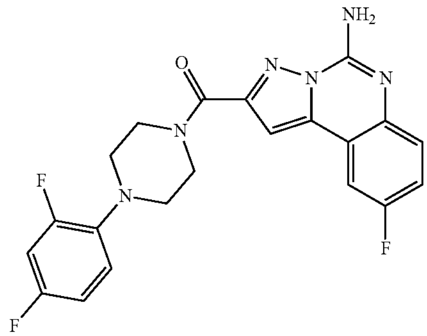 [SMILES: Nc1nc2ccc(F)cc2c2cc(C(=O)N3CCN(c4ccc(F)cc4F)CC3)nn12] | (5-amino-9-fluoropyrazolo[1,5-c]-quinazolin-2-yl)(4-(2,4-difluorophenyl)piperazin-1-yl)methanone | 427 [M + 1] |
| Ex-115 | 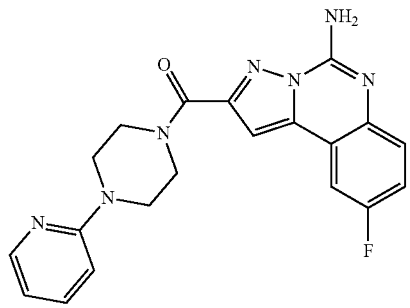 [SMILES: Nc1nc2ccc(F)cc2c2cc(C(=O)N3CCN(c4ccccn4)CC3)nn12] | (5-amino-9-fluoropyrazolo[1,5-c]-quinazolin-2-yl)(4-(pyridin-2-yl)-piperazin-1-yl)methanone | 392 [M + 1]. |

A2a Activity of Compounds of the Invention

Binding affinities of compounds of the invention for the human A2a receptor were determined in a competition binding assay using Scintillation Proximity technology. Thus, 0.3 of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 100 μg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:

Materials

HEK293 cells expressing the human, rat, dog or monkey adenosine 2a receptor (Purchased from Perkin-Elmer # RBHA2AM400UA).

The Tritiated compound was prepared according to published methods.

Wheat germ agglutinin-coated yttrium silicate SPA beads (GE Healthcare # RPNQ0023). Dilute to 25 mg/ml in assay buffer.

Assay Buffer was prepared using Dulbecco's calcium and magnesium free phosphate buffered saline+10 mM $MgCl_2$ Adenosine deaminase from calf intestine, 10 mg/2 ml (Roche #10 102 105 001).

DMSO

A2a antagonist standard (9-chloro-1-(2-furanyl)-[1,2,4]triazolo1,5-c]quinazolin-5-amine from Tocris Bioscience)

Compound Dilution

Make eight 1:3 serial dilutions in 100% DMSO from a 3 mM compound stock

Transfer 50 nl of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This is a 2.5× solution. The final concentration in the assay is 0.5 nM. Calculate the concentration by counting two 5 μl aliquots.

Membrane Preparation

Use 0.25 ug of membrane/well. Dilute membranes to 9.7 μg/ml in assay buffer. Treat with 20 ug/ml adenosine deaminase (ADA) for 15 minutes at room temperature to degrade endogenous adenosine.

Membrane-Bead Mixture

Use 100 μg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 μl of 2.5× solution of the Tritiated compound and 30 μl of the membrane-bead mixture. Incubate for one hour at room temperature with agitation.

Include total binding (assay buffer+1% DMSO) and non-specific binding (CGS15943, 1 μM) wells.

Counting

Allow the beads to settle for one hour.

Count in TopCount.

Calculations

A curve fitting program (i.e., Prism, Activity Base, Chemcart) is used to determine the EC50. The Ki value is calculated using the Cheng-Prusoff equation.

$K\ i = EC50/(1+(\text{radioligand concentration}/Kd))$

Using the foregoing assay method, the following results were obtained using various of the compounds of the invention described herein. Each example compound tested is reported in the following format: Ex-No.: A2a (EC50 value reported in nM). Thus, for example, the compound Ex-2 from Example 1 was determined to have an EC50 using the above-described assay, of 20 nM, and is accordingly reported as "Ex-2: A2a Ki=20":

Ex-2: A2a Ki=20; Ex-3: A2a Ki=677; Ex-4: A2a Ki=9; Ex-5: A2a Ki=12; Ex-6: A2a Ki=10; Ex-7: A2a Ki=16; Ex-8: A2a Ki=136; Ex-9: A2a Ki=3; Ex-10: A2a Ki=36; Ex-11: A2a Ki=61; Ex-12: A2a Ki=316; Ex-13: A2a Ki=373; Ex-14: A2a Ki=2; Ex-15: A2a Ki=85; Ex-16: A2a Ki=131; Ex-17: A2a Ki=17; Ex-18: A2a Ki=3; Ex-19: A2a Ki=67; Ex-20: A2a Ki=15; Ex-21: A2a Ki=51; Ex-22: A2a Ki=128; Ex-23: A2a Ki=26; Ex-24: A2a Ki=224; Ex-25: A2a Ki=333; Ex-26: A2a Ki=120; Ex-27: A2a Ki=18; Ex-28: A2a Ki=9; Ex-29: A2a Ki=17; Ex-30: A2a Ki=1; Ex-31: 2a Ki=2; Ex-32: A2a Ki=1; Ex-33: A2a Ki=32; Ex-34: A2a Ki=7; Ex-35: A2a Ki=130; Ex-36: A2a Ki=12; Ex-37: A2a Ki=15; Ex-38: A2a Ki=25; Ex-39: A2a Ki=27; Ex-40: A2a Ki=6; Ex-41: A2a Ki=5; Ex-42: A2a Ki=3; Ex-43: A2a Ki=80; Ex-44: A2a Ki=18; Ex-45: A2a Ki=10; Ex-46: A2a Ki=34; Ex-47: A2a Ki=1; Ex-48: A2a Ki=40; Ex-49: A2a Ki=35; Ex-50: A2a Ki=2; Ex-51: A2a Ki=128; Ex-52: A2a Ki=33; Ex-53: A2a Ki=48; Ex-54: A2a Ki=139; Ex-55: A2a Ki=10; Ex-56: A2a Ki=49; Ex-57: A2a Ki=165; Ex-58: A2a Ki=69; Ex-59: A2a Ki=21; Ex-60: A2a Ki=22; Ex-61: A2a Ki=21; Ex-62: A2a Ki=134; Ex-63: A2a Ki=7; Ex-64: A2a Ki=2; Ex-65: A2a Ki=5; Ex-66: A2a Ki=145; Ex-67: A2a Ki=473; Ex-68: A2a Ki=24; Ex-69: A2a Ki=14; Ex-70: A2a Ki=7; Ex-71: A2a Ki=11; Ex-72: A2a Ki=37; Ex-73: A2a Ki=11; Ex-74: A2a Ki=5; Ex-75: A2a Ki=20; Ex-76: A2a Ki=300; Ex-77: A2a Ki=2; Ex-78: A2a Ki=0.3; Ex-79: A2a Ki=1; Ex-80: A2a Ki=3; Ex-81: A2a Ki=4; Ex-82: A2a Ki=7; Ex-83: A2a Ki=80; Ex-84: A2a Ki=245; Ex-85: A2a Ki=11; Ex-86: A2a Ki=77; Ex-87: A2a Ki=9; Ex-88: A2a Ki=7; Ex-89: A2a Ki=43; Ex-90: A2a Ki=50; Ex-91: A2a Ki=0.4; Ex-92: A2a Ki=101; Ex-93: A2a Ki=45; Ex-94: A2a Ki=10; Ex-95: A2a Ki=68; Ex-96: A2a Ki=53; Ex-97: A2a Ki=51; Ex-99: A2a Ki=18; Ex-100: A2a Ki=19; Ex-101: A2a Ki=39; Ex-102: A2a Ki=33; Ex-103: A2a Ki=23; Ex-104: A2a Ki=67; Ex-105: A2a Ki=45; Ex-106: A2a Ki=65; Ex-107: A2a Ki=123; Ex-108: A2a Ki=14; Ex-109: A2a Ki=6; Ex-110: A2a Ki=32; Ex-111: A2a Ki=94; Ex-112: A2a Ki=131; Ex-113: A2a Ki=7; Ex-114: A2a Ki=8; Ex-115: A2a Ki=41.

The invention claimed is:

1. A compound, or a pharmaceutically acceptable salt thereof, of Formula (I):

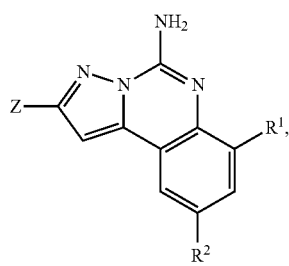

(I)

wherein:

$R^1$ is: halogen; or linear, branched or cyclic alkoxy of up to 6 carbon atoms which is optionally substituted on an alkyl carbon thereof by one or more: (i) halogen; (ii) —OH (iii) alkoxy, or (iv) heterocyclyl moiety, which heterocyclyl moiety is optionally substituted by an aryl moiety, which aryl moiety is optionally substituted with a halogen, or linear-, branched- or cyclic-alkyl of up to 6 carbon atoms, which alkyl substituent is optionally substituted by one or more halogen, lower-alkoxy or —OH;

$R^2$ is: (a) —H; (b) halogen; or (c) linear, branched or cyclic alkoxy of up to 6 carbon atoms which is optionally substituted on an alkyl carbon thereof by one or more: (i) halogen; (ii) —OH (iii) alkoxy; or (iv) heterocyclyl moiety, which heterocyclyl moiety is optionally substituted by an aryl moiety, which aryl moiety is optionally substituted with a halogen, or liner-, branched- or cyclic-alkyl of up to 6 carbon atoms, which alkyl substituent is optionally substituted by one or more halogen, lower-alkoxy or —OH; and Z is:

(I) a moiety of the Formula $R^3$—$CH_2$—, wherein $R^3$ is:

(a) aryl, which may optionally be substituted with one or more:

(i) halogen;

(ii) heterocyclyl, which may optionally be substituted by one or more: (iia) a linear, branched, or cycloalkyl moiety comprising up to about 6 carbon atoms; (iib) ($R^{Ia}$)—O—(C=O)—, wherein: $R^{Ia}$ is a linear-, branched-, or cyclic-alkyl of up to 6 carbon atoms; or (iic) —OH;

(iii) ($R^{Ib}$)$_2$N—, wherein: $R^{Ib}$ is independently: —H; or is a linear-, branched-, or cyclic-alkyl of up to 6 carbon atoms, or wherein both $R^{Ib}$ are taken together with the nitrogen to which they are attached form a $C_{3-6}$-cyclo-amine;

(iv) linear, branched, or cycloalkyl moiety comprising up to about 6 carbon atoms, which is optionally substituted with one or more: (iva) halogen: (ivb) aryl; or (ivc) lower alkoxy which is optionally substituted with one or more halogen;

(v) —CN;

(vi) heteroaryl: which may optionally be substituted with one or more: (via) alkyl wherein said alkyl is a linear-, branched-, or cyclic-alkyl of up to 6 carbon atoms: or (vib) heterocyclyl, which heterocyclyl may optionally be substituted by one or more linear-, branched-, or cyclic-alkyl of up to 6 carbon atoms; or (vii) $R^{Ic}$—O—, wherein: $R^{Ic}$ is aryl or a linear, branched or cyclic-alkyl of up to 6 carbon atoms, which may optionally be substituted on any carbon atom thereof with one or more halogen;

(b) heteroaryl, optionally substituted with one or more: (i) linear, branched or cyclic-alkyl of up to 6 carbon atoms; or (ii) heterocyclyl which is optionally substituted with linear, branched or cyclic-alkyl of up to 6 carbon atoms:

(c) heterocyclyl, optionally substituted with one or more: (i) —OH; or (ii) linear, branched or cyclic-alkyl of up to 6 carbon atoms;

(d) arylheterocyclyl, optionally substituted with one or more of: (i) =O; (ii) halogen; or
(e) heteroarylheterocyclyl; or
(II) a heteroaryl moiety bonded to the pyrazolo-quinazolinyl core through any available ring carbon therein, which heteroaryl moiety comprises 2, 3, or 4 carbon atoms and 1 to 3 heteroatoms which are independently N, S, or O, and wherein, said heteroaryl moiety may optionally be substituted with:
(a) linear, branched or cyclic-alkyl of up to 6 carbon atoms, which may optionally be substituted with aryl or heteroaryl;
(b) $(R^{Id})_2N—$, wherein: $R^{Id}$ is —H or linear, branched or cyclic-alkyl of up to 6 carbon atoms, or wherein both $R^{Id}$ together with the nitrogen atom to which they are bonded form $C_{3-6}$-cyclo-amino, and wherein said alkyl may optionally be substituted on one or more carbon atoms thereof by phenyl which is optionally substituted by one or more halogens;
(c) aryl;
(d) heteroaryl; or
(e) heterocycle, which may optionally be substituted with one or more:
(i) linear, branched or cyclic-alkyl of up to 6 carbon atoms; (ii) aryl, which may optionally be substituted with one or more halogen; or
(III) a moiety of the Formula $R^4—(C=O)—$, wherein $R^4$ is:
(a) heterocyclyl, which may optionally be substituted by one or more: (i) $(R^{Ie})—O—(C=O)—$, wherein $R^{Ie}$ is linear, branched or cyclic-alkyl of up to 6 carbon atoms; (ii) linear, branched or cyclic-alkyl of up to 6 carbon atoms, which alkyl may optionally be substituted with one or more aryl, which aryl may optionally be substituted with one or more halogens: (iii) aryl which may optionally be substituted with one or more halogens; or (iv) heteroaryl;
(b) a spiroheterocyclyl comprising at least 1 heteroatom in each of the fused rings and up to 5 carbon atoms comprising each of the fused rings, which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) $(R^{If})—O—(C=O)—$, wherein $R^{If}$ is -linear-, -branched-$C_{1-6}$-alkyl, or -cyclic-$C_{3-6}$-alkyl; or
(c) $(R^{Ig})_2N—$, wherein: $R^{Ig}$ is independently for each occurrence:
(i) —H;
(ii) aryl, which may optionally be substituted with one or more halogen;
(iii) heteroaryl
(iv) linear, branched or cyclic-alkyl of up to 6 carbon atoms, wherein said alkyl is optionally substituted on one or more carbon atoms thereof with one or more: (iva) aryl, which aryl may optionally be substituted with one or more halogens; or (ivb) heteroaryl;
(v) both R together with the nitrogen atom to which they are bonded form $C_{3-6}$-cyclo-amino, wherein the alkyl portion of said cyclo-amino may optionally be substituted with one or more halogens; or
(vi) one $R^{Ig}$ is a protecting group and the other is —H or linear, branched, or cyclic alkyl of up to 6 carbon atoms.

2. The compound of claim 1, or a pharmaceutically acceptable salt thereof, wherein Z is:
(I) a moiety of the Formula $R^3—CH_2—$, wherein $R^3$ is:
(a) aryl, which is substituted with one or more:
(i) halogen which is —F or —Cl;
(ii) a linear, branched, or cycloalkyl moiety comprising up to about 6 carbon atoms, which is substituted with one or more: (iia) halogen, which is —F or —Cl; or (iib) lower alkoxy which is substituted with —F or —Cl; or
(iii) $R^{Ic}—O—$, wherein $R^{Ic}$ is aryl or a linear, branched or cyclic-alkyl of up to 6 carbon atoms, each of which is substituted, independently for each occurrence, with one or more —F or —Cl; or
(b) arylheterocyclyl, which is substituted with one or more —F;
(II) a heteroaryl moiety bonded to the pyrazolo-quinazolinyl core through any available ring carbon therein, which heteroaryl moiety comprises 2, 3, or 4 carbon atoms and 1 to 3 heteroatoms which are independently N, S, or O, and wherein, said heteroaryl moiety is substituted with: (a) phenyl; or (b) heterocyclyl which is substituted with one or more aryl which is substituted with one or more —F; or
(III) a moiety of the Formula $R^4—(C=O)—$, wherein $R^4$ is:
(a) heterocyclyl, which is substituted by one or more:
(i) linear, branched or cyclic-alkyl of up to 6 carbon atoms, which alkyl is substituted with one or more aryl, said aryl substituted with one or more halogens which are, independently —F or —Br, or (ii) aryl which is substituted with one or more halogens which are independently for each occurrence —F or —Br; or
(b) a spiroheterocyclyl comprising at least 1 nitrogen atom and up to 5 carbon atoms in each of the fused rings, which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) $(R^{If})—O—(C=O)—$, wherein $R^{If}$ is -linear-, -branched-$C_{1-6}$-alkyl, or -cyclic-$C_{3-6}$-alkyl;
(c) $(R^{Ig})_2N—$, wherein: $R^{Ig}$ is independently for each occurrence:
(i) aryl, which is substituted with one or more —F;
(ii) linear, branched or cyclic-alkyl of up to 6 carbon atoms, wherein said alkyl is substituted on one or more carbon atoms thereof with, independently, at least one aryl which is substituted with one or more halogens which are —F or —Br; or
(vi) one $R^{Ig}$ is a t-butoxy carbonyl protecting group and the other is —H or linear, branched, or cyclic alkyl of up to 6 carbon atoms.

3. The compound of claim 1, or a pharmaceutically acceptable salt thereof, wherein $R^1$ is $R^{1a}$, $R^2$ is $R^{2a}$ and Z is $R^{3a}—CH_2$, yielding the structure of Formula IA:

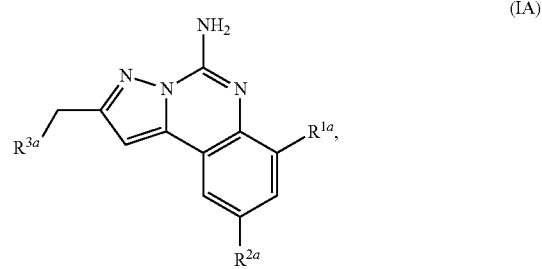

wherein:
R$^{1a}$ is: halogen; or linear, branched or cyclic alkoxy of up to 6 carbon atoms, which may optionally be substituted on one or more carbon atoms thereof with: (i) halogen; (ii) —OH; (iii) lower alkoxy; (iv) heterocyclyl which may optionally be substituted with aryl, wherein said aryl may optionally be substituted with: (iva) halogen or (ivb) linear, branched or cyclic-alkoxy of up to 4 carbon atoms which may optionally be substituted on a carbon atom thereof with lower alkoxy;

R$^{2a}$ is —H or halogen; and

R$^{3a}$ is:
(a) aryl, which may optionally be substituted with one or more:
  (i) halogen;
  (ii) heterocyclyl, which may optionally be substituted by one or mote: (iia) linear, branched, or cycloalkyl moiety comprising up to about 6 carbon atoms; (iib) (R$^{Ia}$)—O—(C=O)—, wherein R$^{Ia}$ is a linear-, branched-, or cyclic-alkyl of up to 6 carbon atoms; or (iic) —OH;
  (iii) (R$^{Ib}$)$_2$N—, wherein: R$^{Ib}$ is independently: —H; or is a linear-, branched-, or cyclic-alkyl of up to 6 carbon atoms, or wherein both R$^{Ib}$ are taken together with the nitrogen to which they are attached form a C$_{3-6}$-cyclo-amine;
  (iv) a linear, branched, or cycloalkyl moiety comprising up to about 6 carbon atoms, which is optionally substituted with one or more: (iva) halogen; (ivb) aryl; or (ivc) lower alkoxy which is optionally substituted with one or more halogen;
  (v) —CN;
  (vi) heteroaryl: which may optionally be substituted with one or more: (via) alkyl wherein said alkyl is a linear-, branched-, or cyclic-alkyl of up to 6 carbon atoms; or (vib) heterocyclyl, which heterocyclyl may optionally be substituted by one or more linear-, branched-, or cyclic-alkyl of up to 6 carbon atoms: or
  (vii) R$^{Ic}$—O—, wherein R$^{Ic}$ is aryl or a linear, branched or cyclic-alkyl of up to 6 carbon atoms, which may optionally be substituted on any carbon atom thereof with one or more halogen;
(b) heteroaryl, optionally substituted with one or more:
  (i) linear, branched or cyclic-alkyl of up to 6 carbon atoms: or (ii) heterocyclyl which is optionally substituted with linear, branched or cyclic-alkyl of up to 6 carbon atoms;
(c) heterocyclyl, optionally substituted with one or more: (i) —OH; or (ii) linear, branched or cyclic-alkyl of up to 6 carbon atoms;
(d) arylheterocyclyl, optionally substituted with one or more of: (i) =O; (ii) halogen: or
(e) heteroarylheterocyclyl.

4. The compound of claim 3, or a pharmaceutically acceptable salt thereof, wherein R$^{3a}$ is:
(a) phenyl, which is optionally substituted with: (i) halogen; (ii) linear, branched or cyclic alkyl of up to 6 carbon atoms; (iii) linear, branched or cyclic alkoxy of up to 6 carbon atoms; (iv) cyano; or (v) amino of the Formula —N(R$^{3aa}$)$_2$, wherein R$^{3aa}$ is independently —H or linear, branched or cyclic alkyl of up to 6 carbon atoms; or
(b) napthalenyl.

5. The compound of claim 3, or a pharmaceutically acceptable salt thereof, wherein R$^{3a}$ is:

(a) quinolinyl, optionally substituted with one or more linear, branched or cyclic alkyl substituents of up to 6 carbon atoms;
(b) isoquinolinyl:
(c) pyrimidinyl;
(d) indazolyl;
(e) pyrazolyl, optionally substituted with linear, branched or cyclic alkyl of up to 6 carbon atoms;
(f) indolyl;
(g) benzothiophenyl;
(h) morpholinyl;
(i) pyridinyl, optionally substituted with morphylinyl; or
(j) thiazolyl, which is optionally substituted with piperazinyl.

6. The compound of claim 3, or a pharmaceutically acceptable salt thereof, wherein R$^3$ is:
(a) piperidinyl, optionally substituted with one or more linear, branched or cyclic alkyl substituents of up to 6 carbon atoms or a hydroxyl;
(b) azetidinyl, optionally substituted with a hydroxyl;
(c) pyrrolidinyl; or
(d) piperazinyl, which is optionally substituted with one or more aryl or phenyl substituents or linear, branched or cyclic alkyl substituent of up to 6 carbon atoms.

7. The compound of claim 3, or a pharmaceutically acceptable salt thereof, wherein R$^{3a}$ is pyrollopyridinylyl.

8. The compound of claim 3, or a pharmaceutically acceptable salt thereof, wherein R$^{3a}$ is:
(a) isoindolinyl, optionally substituted with fluorine; or
(b) pyrrolopyridinyl.

9. The compound of claim 1, or a pharmaceutically acceptable salt thereof, having the formula of Formula IB, or a pharmaceutically acceptable salt thereof:

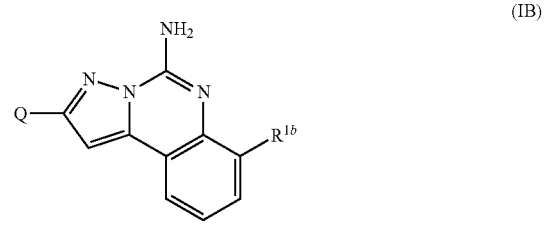

(IB)

wherein:
R$^{Ib}$ is: halogen; or a linear, branched or cyclic alkoxy of up to 6 carbon atoms; and
"Q" is a heteroaryl moiety comprising 2, 3, or 4 carbon atoms and one to 3 heteroatoms which are independently "N" or "O", and wherein Q may be bonded to the core of the compound through any available ring carbon therein or, if present, any available trivalent nitrogen therein, and wherein, said Q-moiety may optionally be substituted on any available ring carbon atom by:
(a) linear, branched or cyclic-alkyl of up to 6 carbon atoms, which may optionally be substituted with aryl or heteroaryl;
(b) (R$^{Id}$)$_2$N—, wherein: R$^{Id}$ is —H or linear, branched or cyclic-alkyl of up to 6 carbon atoms, or wherein both R$^{Id}$ together with the nitrogen atom to which they are bonded form C$_{3-6}$-cycloamino, and wherein said alkyl may optionally be substituted on one or more carbon atoms thereof by phenyl which is optionally substituted by one or more halogens:

(c) aryl;
(d) heteroaryl; or
(e) heterocyclyl, which may optionally be substituted with one or more:
(i) linear, branched or cyclic-alkyl of up to 6 carbon atoms; (ii) aryl, which may optionally be substituted with one or more halogen.

10. The compound of claim 9, or a pharmaceutically acceptable salt thereof, wherein $R^{1b}$ is: (a) —F; (b) methoxy; (c) ethoxy; or (d) a moiety of the formula:

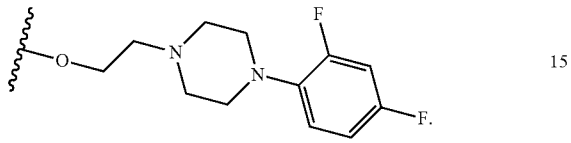

11. The compound of claim 9, or a pharmaceutically acceptable salt thereof, wherein Q is 1,2,4 oxadiazole or a 1,3,4 oxadiazole, bonded to the pyrazolo-quinzolinyl core via 1 ring carbon atom and optionally substituted on the other ring carbon atom with a moiety which is: (a) phenyl; (b) a linear, branched or cyclic alkyl moiety of up to 6 carbon atoms, optionally substituted by phenyl or quinolinyl; (c) morpholinyl; (d) piperazinyl, optionally substituted by aryl; or (e) amino of the formula —N($R^{3b}$)$_2$, wherein $R^{3b}$ is H or a linear, branched or cyclic alkyl moiety of up to 6 carbon atoms which is optionally substituted with phenyl, wherein said phenyl substituent may optionally be substituted with up to 3 fluorine atoms.

12. The compound of claim 1, or a pharmaceutically acceptable salt thereof, having the formula of Formula IC:

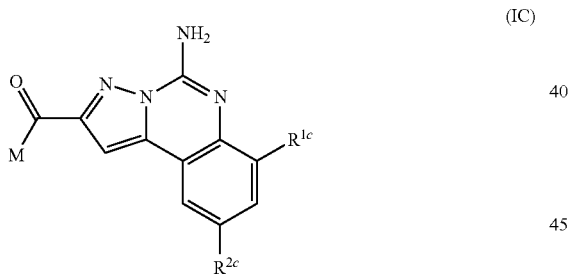

wherein:
$R^{1c}$ is —F, or a linear, branched or cyclic alkoxy moiety of up to 6 carbon atoms;
$R^{2c}$ is —H, or if $R^{2c}$ is selected to be —H, $R^{2c}$ may be —H or —F;
M is:
(a) heterocyclyl, which may optionally be substituted by one or more: (i) ($R^{1e}$)—O—(C=O)—, wherein $R^{1e}$ is linear, branched or cyclic-alkyl of up to 6 carbon atoms; (ii) linear, branched or cyclic-alkyl of up to 6 carbon atoms, which alkyl may optionally be substituted with one or more aryl, which aryl may optionally be substituted with one or more halogen,
(b) a spiroheterocyclyl comprising at least 1 heteroatom in each of the fused rings and up to 5 carbon atoms comprising each of the fused rings, and which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) ($R^{1f}$)—O—(C=O)—, wherein $R^{1f}$ is -linear-, -branched-, or -cyclic-alkyl of up to 6 carbon atoms;
(c) ($R^{1g}$)$_2$N—, wherein: $R^{1g}$ is independently for each occurrence:
(i) —H;
(ii) aryl, which may optionally be substituted with one or more halogen —F;
(iii) heteroaryl;
(iv) linear, branched or cyclic-alkyl of up to 6 carbon atoms, wherein said alkyl is optionally substituted on one or more carbon atoms thereof with one or more: (iva) aryl, which aryl may optionally be substituted with one or more halogens: or (ivb) heteroaryl;
(v) both $R^{1g}$ together with the nitrogen atom to which they are bonded form $C_{3-6}$-cyclo-amino, and wherein the alkyl portion of said cycloamino may optionally be substituted with one or more halogens; or
(vi) one $R^{1g}$ is a protecting group and the other is —H or linear, branched, or cyclic alkyl of up to 6 carbon atoms.

13. The compound of claim 12, or a pharmaceutically acceptable salt thereof, wherein $R^{1c}$ is methoxy.

14. The compound of claim 12, or a pharmaceutically acceptable salt thereof, wherein:
M is:
(a) heterocyclyl, which is substituted by one or more: (i) linear, branched or cyclic-alkyl of up to 6 carbon atoms, which alkyl is substituted with one or more aryl, which aryl is substituted with one or more —F or —Br, (ii) aryl which is substituted with —F or —Br, or (iii) piperazinyl;
(b) a spiroheterocyclyl comprising at least 1 nitrogen atom in each of the fused rings and up to 5 carbon atoms comprising each of the fused rings, which spiroheterocyclyl may optionally be substituted with: (i) linear, branched or cyclic-alkyl of up to 6 carbon atoms, which may optionally be substituted on one or more carbon atoms thereof with aryl; (ii) aryl; or (iii) ($R^{1f}$)—O—(C=O)—, wherein $R^{1f}$ is -linear-, -branched-, or -cyclic-alkyl of up to 6 carbon atoms;
(c) ($R^{1g}$)$_2$N—, wherein: $R^{1g}$ is independently for each occurrence:
(i) aryl, which is substituted with one or more —F;
(ii) linear, branched or cyclic-alkyl of up to 6 carbon atoms, wherein said alkyl is on one or more carbon atoms thereof with one or more aryl, which aryl is substituted with one or more —F or —Br; or
(iii) one $R^{1g}$ is t-butoxy carbonyl and the other is —H or linear, branched, or cyclic alkyl of up to 6 carbon atoms.

15. The compound of claim 12, or a pharmaceutically acceptable salt thereof, wherein M is a heterospirobicyclo moiety of the formula:

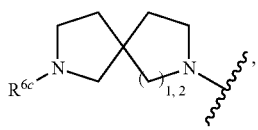

wherein, $R^{6c}$ is: (i) —H; (ii) a linear, branched or cyclic alkyl moiety of up to 6 carbon atoms; (iii) t-butoxycarbonyl; (iv) benzyl; or (v) acetyl.

16. The compound of claim 1 selected from:

7-methoxy-2-(oxazol-5-yl)pyrazolo[1,5-c]quinazolin-5-amine;
7-(2-(4-(2,4-difluorophenyl)piperazin-1-yl)ethoxy)-2-(furan-2-yl)pyrazolo[1,5-c]quinazolin-5-amine;
2-(furan-2-yl)-7-(2-(4-(4-(2-methoxyethoxy)phenyl)piperazin-1-yl)ethoxy)pyrazolo[1,5-c]quinazolin-5-amine;
2-benzyl-7-methoxypyrazolo[1,5-c]quinazolin-5-amine;
2-(4-fluorobenzyl)-7-methoxypyrazolo[1,5-c]quinazolin-5-amine;
2-(2,4-difluorobenzyl)-7-methoxypyrazolo[1,5-c]quinazolin-5-amine;
7-methoxy-2-(naphthalen-1-ylmethyl)pyrazolo[1,5-c]quinazolin-5-amine;
7-methoxy-2-(4-(piperidin-1-yl)benzyl)pyrazolo[1,5-c]quinazolin-5-amine;
7-methoxy-2-(quinolin-8-ylmethyl)pyrazolo[1,5-c]quinazolin-5-amine;
7-methoxy-2-(pyridin-5-ylmethyl)pyrazolo[1,5-c]quinazolin-5-amine;
2-(4-(dimethylamino)benzyl)-7-methoxypyrazolo[1,5-c]quinazolin-5-amine;
7-methoxy-2-(4-(4-methylpiperazin-1-yl)benzyl)pyrazolo[1,5-c]quinazolin-5-amine;
7-methoxy-2-((2-(4-methylpiperazin-1-yl)thiazol-4-yl)methyl)pyrazolo[1,5-c]quinazolin-5-amine;
7-methoxy-2-(quinolin-4-ylmethyl)pyrazolo[1,5-c]quinazolin-5-amine;
7-methoxy-2-(quinolin-5-ylmethyl)pyrazolo[1,5-c]quinazolin-amine;
2-((1H-indazol-5-yl)methyl)-7-methoxypyrazolo[1,5-c]quinazolin-5-amine;
7-methoxy-2-(2-(trifluoromethyl)benzyl)pyrazolo[1,5-c]quinazolin-5-amine;
7-methoxy-2-(2-morpholinobenzyl)pyrazolo[1,5-c]quinazolin-5-amine;
7-methoxy-2-(2-(piperazin-1-yl)benzyl)pyrazolo[1,5-c]quinazolin-5-amine;
7-methoxy-2-((2-morpholinopyridin-3 yl)methyl)pyrazolo[1,5-c]quinazolin-5-amine;
7-methoxy-2-(2-(morpholinomethyl)benzyl)pyrazolo[1,5-c]quinazolin-5-amine;
7-methoxy-2-(4-morpholinobenzyl)pyrazolo[1,5-c]quinazolin-5-amine;
7-methoxy-2-(3-morpholinobenzyl)pyrazolo[1,5-c]quinazolin-5-amine;
tert-butyl 4-(4-((5-amino-7 methoxypyrazolo[1,5-c]quinazolin-2-yl)methyl)phenyl)piperazine-1-carboxylate;
7-methoxy-2-(4-(piperazin-1-yl)benzyl)pyrazolo[1,5-c]quinazolin-5-amine;
2-(2-(4-ethylpiperazin-1-yl)benzyl)-7-methoxypyrazolo[1,5-c]quinazolin-5-amine;
1-(2-((s-no-7-methoxypyrazolo[1,5c]quinazolin-2-yl)methyl)benzyl)-4-methylpiperidin-4-ol;
1-(2-((5-amino-7-methoxypyrazolo[1,5-c]quinazolin-2-yl)methyl)benzyl)azetidin-3-ol;
7-methoxy-2-(2-(pyrolidin-1-ylmethyl)benzyl)pyrazolo[1,5-c]quinazolin-5-amine;
2-(2-fluorobenzyl)-7-methoxypyrazolo[1,5-c]quinazolin-5-amine;
2-(3-fluorobenzyl)-7-methoxypyrazolo[1,5-c]quinazolin-5-amine;
7-methoxy-2-(2-methoxybenzyl)pyrazolo[1,5-c]quinazolin-5-amine;
7-methoxy-2-(4-methoxybenzyl)pyrazolo[1,5-c]quinazolin-5-amine;
7-methoxy-2-(3-methoxybenzyl)pyrazolo[1,5-c]quinazolin-5-amine;
7-methoxy-2-(4-(trifluoromethyl)benzyl)pyrazolo[1,5-c]quinazolin-5-amine;
7-methoxy-2-(3-(trifluoromethyl)benzyl)pyrazolo[1,5-c]quinazolin-5-amine;
7-methoxy-2-((1-methyl-1H-pyrazol-4-yl)methyl)pyrazolo[1,5-c]quinazolin-5-amine;
2-(2-chloro-6-fluorobenzyl)-7-methoxypyrazolo[1,5-c]quinazolin-5-amine;
7-methoxy-2-(2,3,4-trifluorobenzyl)pyrazolo[1,5-c]quinazolin-5-amine;
2-(2,3-difluorobenzyl)-7-methoxypyrazolo[1,5-c]quinazolin-5-amine;
2-((1H indol-4-yl)methyl)-7-methoxypyrazolo[1,5-c]quinazolin-5-amine;
2-(2,6-difluorobenzyl)-7-methoxypyrazolo[1,5-c]quinazolin-5-amine;
2-(2,3-dichlorobenzyl)-7-methoxypyrazolo[1,5-c]quinazolin-5-amine;
2-(isoquinolin-5-ylmethyl)-7-methoxypyrazolo[1,5-c]quinazolin-5-amine;
2-(2-chlorobenzyl)-7-methoxypyrazolo[1,5-c]quinazolin-5-amine;
7-methoxy-2-(2-(trifluoromethoxy)benzyl)pyrazolo[1,5-c]quinazolin-5-amine;
2-(2-(dimethylamino)benzyl)-7-methoxypyrazolo[1,5-c]quinazolin-5-amine;
7-methoxy-2-(3-(methoxymethyl)benzyl)pyrazolo[1,5-c]quinazolin-5-amine;
2-(3-chlorobenzyl)-7-methoxypyrazolo[1,5-c]quinazolin 5-amine;
2-((5-amino-7-methoxypyrazolo[1,5-c]quinazolin 2-yl)methyl)benzonitrile;
2-(2-(benzyloxy)benzyl)-7-methoxypyrazolo[1,5-c]quinazolin-5-amine;
3-((5-amino-7-methoxypyrazolo[1,5-c]quinazolin-2-yl)methyl)benzonitrile;
2-(benzo[b]thiophen-7-ylmethyl)-7-methoxypyrazolo[1,5-c]quinazolin-5-amine;
2-(3-(3,5-dimethyl-1H-pyrazol-1-yl)benzyl)-7-methoxypyrazolo[1,5-c]quinazolin-5-amine;
2-(2-(difluoromethoxy)benzyl)-7-methoxypyrazolo[1,5-c]quinazolin-5-amine;
4-((5-amino-7-methoxypyrazolo[1,5-c]quinazolin 2-yl)methyl)isoindolin-1-one;
7-methoxy-2-((2-methylquinolin-5-yl)methyl)pyrazolo[1,5-c]quinazolin-5-amine;
2-(3-(1 H-pyrazol-1-yl)benzyl)-7-methoxypyrazolo[1,5-c]quinazolin-5-amine;
2-(3-fluoro-2-methylbenzyl)-7-methoxypyrazolo[1,5-c]quinazolin-5-amine;
7-methoxy-2-((2-methylquinolin-8-yl)methy)pyrazolo[1,5-c]quinazolin-5-amine;
3-((5-amino-7-methoxypyrazolo[1,5-c]quinazolin 2-yl)methyl)-2-fluorobenzonitrile;
3-((5-amino-7-methoxypyrazolo[1,5-c]quinazolin-2-yl)methyl)-5-fluorobenzonitrile;
2-(2-(1H pyrazol-1-yl)benzyl)-7-methoxypyrazolo[1,5-c]quinazolin-5-amine;
2-(2,5-difluorobenzyl)-7-methoxypyrazolo[1,5-c]quinazolin-5-amine;

2-(3,5-difluorobenzyl)-7-methoxypyrazolo[1,5-c]quinazolin-5-amine;
7-methoxy-2-((4-phenylpiperazin-1-yl)methyl)pyrazolo[1,5-c]quinazolin-5-amine;
1-((5-amino-7-methoxypyrazolo[1,5-c]quinazolin-2 yl)methyl)azetidin-3-ol;
2-((5-fluoroquinolin-2-yl)methy)-7-methoxypyrazolo[1,5-c]quinazolin-5-amine;
2-((5,7-dihydro-6H-pyrrolo[3,4-b]pyridin-6-yl)methyl)-7-methoxypyrazolo[1,5-c]quinazolin-5-amine;
(5-amino-7-methoxypyrazolo[1,5-c]quinazolin-2-yl)(4-(pyridin-2 yl)piperazin-1-yl)methanone;
(5-amino-7 methoxypyrazolo[1,3-c]quinazolin-2-yl)(4-benzylpiperazin-J -yl)methanone;
(5-amino-7-methoxypyrazolo[1,5-c]quinazolin-2-yl)(piperidin-1-yl)methanone;
(5-amino-7-methoxypyrazolo[1,5-c]quinazolin-2-yl)(4-(4-fluorobenzyl)piperazin-1-yl)methanone;
(5-amino-7-methoxypyrazolo[1,5-c]quinazolin-2-yl)(pyrrolidin-1-yl)methanone;
tert-butyl 4-(5-amino-7-methoxypyrazolo[1,5-c]quinazoline-2-carbonyl)piperazine-1-carboxylate;
(5-amino-7-methoxypyrazolo[1,5-c]quinazolin-2-yl)(piperazin-1-yl)methanone;
5-amino-N-(2,4-difluorobenzyl)-7-methoxypyrazolo[1,5-c]quinazoline-2-carboxamide;
(5-amino-7-methoxypyrazolo[1,3-c]quinazolin-2-yl)(4-(2,4-difluorophenyl)piperazin-1-yl)methanone;
5-amino-N-(4-bromo-2-fluorobenzyl)-7-methoxypyrazolo[1,5-c]quinazolin-2-carboxamide;
5-amino-7-methoxy-N-phenylpyrazolo[1,5-c]quinazoline-2-carboxamide;
5-amino-N-benzyl-7-methoxy-N-methylpyrazolo[1,5-c]quinazoline-2-carboxamide;
5-amino-7-methoxy-N-methyl-N-(quinolin-8-ylmethyl)pyrazolo[1,5-c]quinazoline-2-carboxamide;
tert-butyl 8-(5-amino-7-methoxypyrazolo[1,5-c]quinazoline-2-carbonyl)-2,8-diazaspiro[4.5]decane-2-carboxylate;
(5-amino-7-methoxypyrazolo[1,3-c]quinazolin-2-yl)(2,8-diazaspiro[4.5]decan-8-yl)methanone;
tert-butyl 7-(5-amino-7-methoxypyrazolo[1,5-c]quinazoline-2-carbonyl)-2,7-diazaspiro[4.4]nonane-2-carboxylate;
(5-amino-7-methoxypyrazolo[1,5-c]quinazolin-2-yl)(2,7-diazaspiro[4.4]nonan-2-yl)methanone;
1-(7-(5-amino-7-methoxypyrazolo[1,5-c]quinazoline-2-carbonyl)-2,7-diazaspiro[4.4]nonan-2-yl)ethan-1-one;
methyl 7-(5-amino-7-methoxypyrazolo[1,5-c]quinazoline-2-carbonyl)-2,7-diazaspiro[4.4]nonane 2-carboxylate;
(5-amino-7 methoxypyrazolo[1,5-c]quinazolin-2-yl)(7-ethyl-2,7-diazaspiro[4.4]nonan-2-yl)methanone;
(5-amino-7-methoxypyrazolo[1,5-c]quinazolin-2-yl)(7 benzyl-2,7-diazaspiro[4.4]nonan-2-yl)methanone;
5-amino-7-methoxy-N-(quinolin-8-ylmethyl)pyrazolo[1,5-c]quinazoline-2-carboxamide;
7-methoxy-2-(3-phenyl-1,2,4-oxadiazol-5-yl)pyrazolo[1,5-c]quinazolin-5-amine;
2-(3-benzyl-1,2,4-oxadiazol-5-yl)-7-methoxypyrazolo[1,5-c]quinazolin-5-amine;
2-(quinolin-8-ylmethyl)pyrazolo[1,5-c]quinazolin-5-amine;
2-(quinazolin-4-ylmethyl)pyrazolo[1,5-]quinazolin-5-amine;
2-(2-morpholinobenzyl)pyrazolo[1,5-c]quinazolin-5-amine;
2-(2-(morpholinomethyl)benzyl)pyrazolo[1,5-c]quinazolin-5-amine;
2-(5-(quinolin-8-yl)-1,3,4-oxadiazol-2-yl)pyrazolo[1,5-c]quinazolin-5-amine;
7-methoxy-2-(5-(quinolin-7-ylmethyl)-1,3,4-oxadiazol-2-yl)pyrazolo[1,5-c]quinazolin 5-amine;
7-methoxy-2-(5-(quinolin-8-yl)-1,3,4-oxadiazol-2-yl)pyrazolo[1,5-c]quinazolin-5-amine;
7-methoxy-2-(5-morpholino-1,3,4-oxadiazol-2-yl)pyrazolo[1,5-c]quinazolin 5-amine;
7-methoxy-2-(5-(4-phenylpiperazin-1-yl)-1,3,4-oxadiazol-2-yl)pyrazolo[1,5-c]quinazolin-5-amine;
5-(5-amino-7-methoxypyrazolo[1,5-c]quinazolin-2-yl)-N-(2,4-difluorobenzyl)-1,3,4-oxadiazol-2-amine;
2-benzyl-9-fluoropyrazolo[1,5-c]quinazolin-5-amine;
9-fluoro-2-(quinolin-8-ylmethyl)pyrazolo[1,5-c]quinazolin-5-amine;
9-fluoro-2-(2-morpholinobenzyl)pyrazolo[1,5-c]quinazolin-5-amine;
9-fluoro-2-((2-morpholinopyridin-3-yl)methyl)pyrazolo[1,5-c]quinazolin 5-amine;
2-benzyl-7-fluoropyrazolo[1,5-c]quinazolin-5-amine;
7-fluoro-2-(quinolin-8-ylmethyl)pyrazolo[1,5-c]quinazolin-5-amine;
(5-amino-7-fluoropyrazolo[1,5-c]quinazolin-2 yl)(4-(pyridin-2-yl)piperazin-1-yl)methanone;
(5-amino-7-fluoropyrazolo[1,5-c]quinazolin-2-yl)(4-(2,4-difluorophenyl)piperazin-1-yl)methanone;
(5-amino-9-fluoropyrazolo[1,5-c]quinazolin 2-yl)(4-(2,4-difluorophenyl)piperazin-1-yl)methanone;
(5-amino-9-fluoropyrazolo[1,5-c]quinazolin-2-yl)(4-(pyridin-2-yl)piperazin-1-yl)methanone;
7-fluoro-2-(5-(quinolin-8-yl)-1,3,4-oxadiazol-2-yl)pyrazolo[1,5-c]quinazolin-5-amine; and
7-fluoro-2-(5-(quinolin-7-ylmethyl)-1,3,4-oxadiazol-2-yl)pyrazolo[1,5-c]quinazolin-5-amine;
or a pharmaceutically acceptable salt of any thereof.

17. A pharmaceutical composition comprising at least one compound of claim 1, or a pharmaceutically acceptable salt thereof, and at least one excipient.

18. A method of treating a central nervous system (CNS) disorder comprising administering to a patient in need thereof a therapeutically effective amount of a pharmaceutical composition of claim 17.

19. A pharmaceutical composition comprising at least one compound of claim 16, or a pharmaceutically acceptable salt thereof and at least one excipient.

* * * * *